(12) United States Patent
Thess et al.

(10) Patent No.: US 10,232,024 B2
(45) Date of Patent: *Mar. 19, 2019

(54) NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED ALLERGENIC ANTIGEN OR AN AUTOIMMUNE SELF-ANTIGEN

(71) Applicant: CureVac AG, Tübingen (DE)

(72) Inventors: Andreas Thess, Kusterdingen (DE); Thomas Schlake, Gundelfingen (DE); Jochen Probst, Wolfschlugen (DE)

(73) Assignee: CureVac AG, Tübingen (DE)

( * ) Notice: Subject to any disclaimer, the term of this patent is extended or adjusted under 35 U.S.C. 154(b) by 301 days.

This patent is subject to a terminal disclaimer.

(21) Appl. No.: 14/378,591

(22) PCT Filed: Feb. 15, 2013

(86) PCT No.: PCT/EP2013/000458
§ 371 (c)(1),
(2) Date: Aug. 13, 2014

(87) PCT Pub. No.: WO2013/120626
PCT Pub. Date: Aug. 22, 2013

(65) Prior Publication Data
US 2015/0165006 A1 Jun. 18, 2015

(30) Foreign Application Priority Data

Feb. 15, 2012 (WO) .................. PCT/EP2012/000672

(51) Int. Cl.
| | |
|---|---|
| A61K 39/00 | (2006.01) |
| A61K 39/35 | (2006.01) |
| C12N 15/63 | (2006.01) |
| C12N 15/67 | (2006.01) |
| C12N 15/85 | (2006.01) |
| A61K 48/00 | (2006.01) |

(52) U.S. Cl.
CPC .......... *A61K 39/0008* (2013.01); *A61K 39/35* (2013.01); *A61K 48/005* (2013.01); *C12N 15/63* (2013.01); *C12N 15/67* (2013.01); *C12N 15/85* (2013.01); *A61K 48/00* (2013.01); *A61K 2039/53* (2013.01); *A61K 2039/55516* (2013.01); *A61K 2039/64* (2013.01); *C12N 2830/50* (2013.01)

(58) Field of Classification Search
None
See application file for complete search history.

(56) References Cited

U.S. PATENT DOCUMENTS

| | | |
|---|---|---|
| 5,908,779 A | 6/1999 | Carmichael et al. |
| 8,217,016 B2 | 7/2012 | Hoerr et al. |
| 8,383,340 B2 | 2/2013 | Ketterer et al. |
| 8,703,906 B2 | 4/2014 | Baumhof et al. |
| 8,968,746 B2 | 3/2015 | Baumhof et al. |
| 9,155,788 B2 | 10/2015 | Hoerr et al. |
| 9,234,013 B2 | 1/2016 | Thess et al. |
| 9,447,431 B2 * | 9/2016 | Thess ..................... C12N 15/63 |
| 9,669,089 B2 | 6/2017 | Thess et al. |
| 9,839,697 B2 * | 12/2017 | Thess ..................... C12N 15/67 |
| 2005/0009028 A1 | 1/2005 | Heintz et al. |
| 2005/0032730 A1 | 2/2005 | Von Der Mulbe et al. |
| 2005/0048549 A1 | 3/2005 | Cao et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2007/0111203 A1 | 5/2007 | Cao et al. |

(Continued)

FOREIGN PATENT DOCUMENTS

| | | |
|---|---|---|
| WO | WO 1995/015394 | 6/1995 |
| WO | WO 1998/042856 | 10/1998 |
| WO | WO 2001/012824 | 2/2001 |
| WO | WO 2002/098443 | 12/2002 |
| WO | WO 2005/035771 | 4/2005 |
| WO | WO 2005/040377 | 5/2005 |
| WO | WO 2006/008154 | 1/2006 |
| WO | WO 2006/024518 | 3/2006 |
| WO | WO 2007/024708 | 3/2007 |
| WO | WO 2009/030481 | 3/2009 |
| WO | WO 2009/095226 | 8/2009 |

(Continued)

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

(Continued)

*Primary Examiner* — Zachary S Skelding
(74) *Attorney, Agent, or Firm* — Paker Highlander PLLC

(57) ABSTRACT

The present invention relates to a nucleic acid sequence, comprising or coding for a coding region, encoding at least one peptide or protein comprising an allergenic antigen or an autoimmune self-antigen or a fragment, variant or derivative thereof, at least one histone stem-loop and a poly(A) sequence or a polyadenylation signal. Furthermore the present invention provides the use of the nucleic acid for increasing the expression of said encoded peptide or protein. It also discloses its use for the preparation of a pharmaceutical composition, especially a vaccine, e.g. for use in the treatment of allergies or autoimmune diseases. The present invention further describes a method for increasing the expression of a peptide or protein comprising an allergenic antigen or an autoimmune self-antigen or a fragment, variant or derivative thereof, using the nucleic acid comprising or coding for a histone stem-loop and a poly(A) sequence or a polyadenylation signal.

15 Claims, 23 Drawing Sheets

Figure 20:
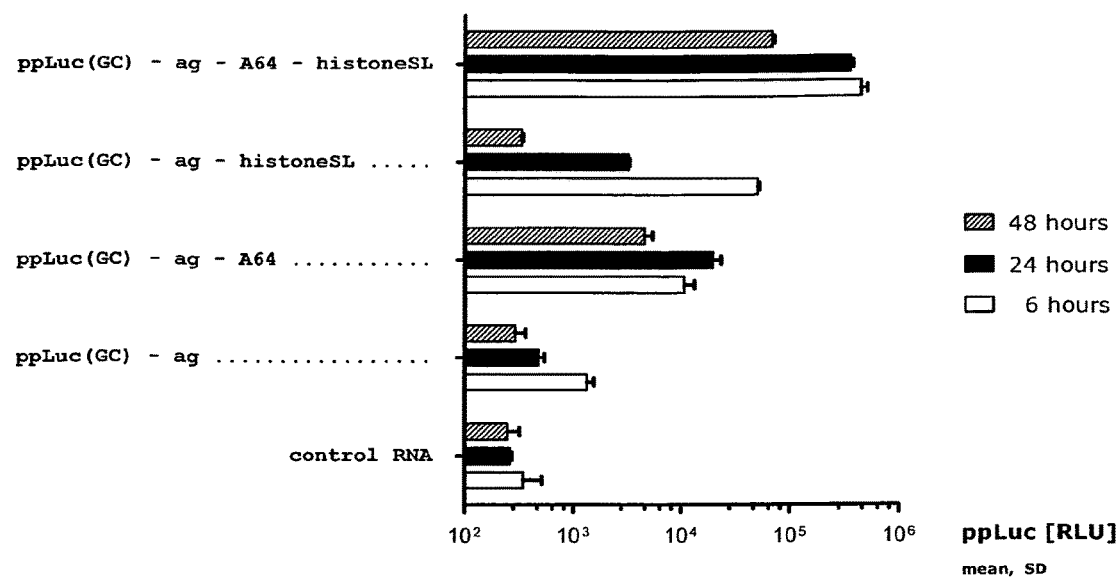

Specification includes a Sequence Listing.

(56) References Cited

U.S. PATENT DOCUMENTS

| | | | |
|---|---|---|---|
| 2007/0172949 | A9 | 7/2007 | Liu et al. |
| 2008/0025944 | A1 | 1/2008 | Hoerr |
| 2008/0267873 | A1 | 10/2008 | Hoerr |
| 2009/0324584 | A1 | 12/2009 | Hoerr et al. |
| 2010/0048883 | A1 | 2/2010 | Ketterer et al. |
| 2010/0120152 | A1 | 5/2010 | Wooddell et al. |
| 2010/0129392 | A1 | 5/2010 | Shi et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mülbe et al. |
| 2010/0291156 | A1 | 11/2010 | Barner et al. |
| 2010/0303851 | A1 | 12/2010 | Hoerr et al. |
| 2010/0305196 | A1 | 12/2010 | Probst et al. |
| 2011/0053829 | A1 | 3/2011 | Baumhof |
| 2011/0077287 | A1 | 3/2011 | Von Der Mülbe et al. |
| 2011/0250225 | A1 | 10/2011 | Fotin-Mleczek |
| 2011/0269950 | A1 | 11/2011 | Von Der Mülbe et al. |
| 2011/0311472 | A1 | 12/2011 | Hoerr et al. |
| 2012/0009221 | A1 | 1/2012 | Hoerr et al. |
| 2012/0021043 | A1 | 1/2012 | Kramps et al. |
| 2012/0213818 | A1 | 8/2012 | Hoerr et al. |
| 2012/0258046 | A1 | 10/2012 | Mutzke |
| 2013/0121988 | A1 | 5/2013 | Hoerr et al. |
| 2013/0129754 | A1 | 5/2013 | Thess et al. |
| 2013/0195867 | A1 | 8/2013 | Hoerr et al. |
| 2013/0202645 | A1 | 8/2013 | Barner et al. |
| 2013/0251742 | A1 | 9/2013 | Probst et al. |
| 2013/0259879 | A1 | 10/2013 | Baumhof et al. |
| 2013/0273001 | A1 | 10/2013 | Hoerr et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2014/0037660 | A1 | 2/2014 | Fotin-Mleczek et al. |
| 2014/0147454 | A1 | 5/2014 | Chakraborty et al. |
| 2014/0294877 | A1 | 10/2014 | Baumhof et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0104476 | A1 | 4/2015 | Von Der Mülbe et al. |
| 2015/0118183 | A1 | 4/2015 | Baumhof |
| 2015/0118264 | A1 | 4/2015 | Baumhof et al. |
| 2015/0141498 | A1 | 5/2015 | Mutzke |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0258214 | A1 | 9/2015 | Baumhof et al. |
| 2015/0306249 | A1 | 10/2015 | Baumhof et al. |
| 2015/0320847 | A1 | 11/2015 | Thess et al. |

FOREIGN PATENT DOCUMENTS

| | | |
|---|---|---|
| WO | WO 2010/023260 | 3/2010 |
| WO | WO 2010/132867 | 11/2010 |
| WO | WO 2011/069529 | 6/2011 |
| WO | WO 2012/013326 | 2/2012 |
| WO | WO 2012/019630 | 2/2012 |
| WO | WO 2012/019780 | 2/2012 |
| WO | WO 2012/116714 | 9/2012 |
| WO | WO 2013/120627 | 8/2013 |
| WO | WO 2013/120628 | 8/2013 |
| WO | WO 2013/120629 | 8/2013 |
| WO | WO 2015/024665 | 2/2015 |
| WO | WO 2015/024668 | 2/2015 |

OTHER PUBLICATIONS

Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473, 2000.*
Blumenthal et al. 'Definition of an Allergen.' Allergens and Allergen Immunotherapy. Ed. R Lockey, S. Bukantz and J. Bousquet. New York: Marcel Decker, 2004.37-50.*

Avni et al., "The 5' terminal oligopyrimidine tract confers translational control on TOP mRNAs in a cell type-and sequence context-dependent manner," *Nucleic Acids Research*, 25(5):995-1001, 1997.
Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.
Caldarola et al., "Translational regulation of terminal oligopyrimidine mRNAs induced by serum and amino acids involves distinct signaling events," *The Journal of Biological Chemistry*, 279(14):13522-135531, 2004.
Cameron et al., "Recent advances in transgenic technology," *Molecular Biotechnology*, 7:253-265, 1997.
Chakrabarti et al., "The mammalian target of rapamycin complex 1 regulates leptin biosynthesis in adipocytes at the level of translation: the role of the 5'-untranslated region in the expression of leptin messenger ribonucleic acid," *Molecular Endocrinology*, 22(10):2260-2267, 2008.
Damgaard and Lykke-Andersen, "Translational coregulation of 5'TOP mRNAs by TIA-1 and TIAR," *Genes Dev.*, 25:2057-2068, 2011.
Database EMBL Accession No. EM_STD:AB063609, "*Homo sapiens* RPL36AL mRNA for ribosomal protein L36a-like, complete cds," 2002.
Database Geneseq Accession No. ATN08647, "Human transcriptional regulatory element SEQ ID No. 6587," 2008.
Davuluri et al., "CART classification of human 5' UTR sequences," *Genome Research*, 10(11):1807-1816, 2000.
Gerwitz et al., "Nucleic acid therapeutics: state of the art and future prospects," *Blood*, 92(3):712-736, 1998.
Ginn et al., "Gene therapy clinical trails worldwide to 2012—an update," *Journal of Gene Medicine*, 15:65-77, 2013.
Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.
Knapinska et al., "Molecular mechanisms regulation mRNA stability: physiological and pathological significance," *Current Genomics*, 6(6):1-16, 2005.
Ledda et al., "Effect of 3'UTR length on the translational regulation of 5'-terminal oligopyrimidine mRNAs," *Gene*, 344:213-220, 2005.
Levy et al., "Oligopyrimidine tract at the 5' end of mammalian ribosomal protein mRNAs is required for their translational control," *Proc. Natl. Acad. Sci. USA*, 88:3319-3323, 1991.
Meyuhas, "Synthesis of the translational apparatus is regulated at the translational level," *Eur. J. Biochem.*, 267:6321-6330, 2000.
Montoliu, "Gene transfer strategies in animal transgenesis," *Cloning and Stem Cells*, 4(1):39-46, 2002.
Niemann, "Transgenic farm animals get off the ground," *Transgenic Research*, 7:73-75, 1998.
Office Action issued in U.S. Appl. No. 13/321,474, dated Apr. 6, 2015.
Office Action issued in U.S. Appl. No. 14/378,538, dated Nov. 12, 2015.
Office Action issued in U.S. Appl. No. 14/378,606, dated May 27, 2015.
Office Action issued in U.S. Appl. No. 14/378,606, dated Nov. 3, 2015.
Office Action issued in U.S. Appl. No. 14/388,226, dated Nov. 6, 2015.
Orom et al., "MicroRNA-10a binds the 5'UTR of ribosomal protein mRNAs and enhances their translation," *Molecular Cell*, 30:460-471, 2008.
PCT International Search Report and Written Opinion issued in International Application No. PCT/EP2013/000938, dated Nov. 13, 2013.
PCT International Search Report and Written Opinion issued in International Application No. PCT/EP2013/000937, dated Aug. 30, 2013.
Prelle et al., "Establishment of pluripotent cell lines from vertebrate species—present status and future prospects," *Cells Tissues Organs*, 165:220-236, 1999.

(56) References Cited

OTHER PUBLICATIONS

Ristevski, "Making better transgenic models," *Molecular Biotechnology*, 29:153-163, 2005.
Shen et al., "Structures required for poly(A) tail-independent translation overlap with, but ar distinct from, cap-independent translation and RNA replication signals at the 3' end of *Tobacco necrosis* virus RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Smith, "Gene transfer in higher animals: theoretical considerations and key concepts," *Journal of Biotechnology*, 99:1-22, 2002.
Thess et al., "Sequence-engineered mRNA without chemical nucleoside modifications enables an effective protein therapy in large animals," *Molecular Therapy*, pp. 1-9 and Supplementary Material, 2015.
Wooddell et al., "Sustained liver-specific transgene expression from the albumin promoter in mice following hydrodynamic plasmid DNA delivery," *The Journal of Gene Medicine*, 10:551-563, 2008.
Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.
Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.
Eckner et al., "Mature mRNA 3' end formation stimulates RNA export from the nucleus," *The EMBO Journal*, 10(11):3513-3522, 1991.
Gorgoni et al., "The stem-loop binding protein stimulates histone translation at an early step in the initiation pathway," *RNA*, 11:1030-1042, 2005.
Office Action issued in U.S. Appl. No. 14/378,538, dated Jun. 21, 2016.
Office Action issued in U.S. Appl. No. 14/378,572, dated Aug. 12, 2016.
Office Action issued in U.S. Appl. No. 14/378,572, dated Mar. 3, 2016.
Office Action issued in U.S. Appl. No. 14/388,224, dated Apr. 21, 2016.
Office Action issued in U.S. Appl. No. 14/388,226, dated Jun. 21, 2016.
Dominski et al., "Stem-loop binding protein facilitates 3'-end formation by stabilizing U7 snRNP binding to histone pre-mRNA," *Mol Cell Biol.*, 19(5):3561-3570, 1999.
U.S. Appl. No. 14/378,538, filed Aug. 13, 2014, Thess et al.
U.S. Appl. No. 14/378,572, filed Aug. 13, 2014, Thess et al.
U.S. Appl. No. 14/378,606, filed Aug. 13, 2014, Thess et al.
Battle and Doudna, "The stem-loop binding protein forms a highly stable and specific complex with the 3' stem-loop of histone mRNAs", *RNA*, 7:123-132, 2001.
Collart et al., "A human histone H2B.1 variant gene, located on chromosome 1, utilizes alternative 3' end processing", *Journal of Cellular Biochemistry*, 50:374-385, 1992.
Gallie et al., "The histone 3'-terminal stem-loop is necessary for translation in Chinese hamster ovary cells", *Nucleic Acids Res.*, 24(10):1954-62, 1996.
Holtkamp et al., "Modification of antigen-encoding RNA increases stability, translational efficacy, and T-cell stimulatory capacity of dendritic cells", *Blood*, 108(13):4009-17, 2006.
Kato et al., "Histone H2B as an antigen recognized by lung cancer-specific human monoclonal antibody HB4C5", *Human Antibodies and Hybridomas*, 2(2):94-101, 1991.
Levy et al., "Sequence and functional characterization of the terminal exon of the human insulin receptor gene", *Biochim Biophys Acta.*, 1263(3):253-7, 1995.
Ling et al., "The histone 3'-terminal stem-loop-binding protein enhances translation through a functional and physical interaction with eukaryotic initiation factor 4G (eIF4G) and eIF3", *Mol Cell Biol.*, 22(22):7853-67, 2002.

Lopez and Samuelsson, "Early evolution of histone mRNA 3' end processing", *Bioinformatics*, 14(1):1-10, 2008.
Nartia et al., "NELF interacts with CDC and participates in 3' end processing of replication-dependent histone mRNAs", *Molecular Cell*, 26(3):349-365, 2007.
Office communication issued in U.S. Appl. No. 13/321,474, dated May 20, 2014.
Pandey et al., "Introns in histone genes alter the distribution of 3' ends", *Nucleic Acids Res.*, 18(11):3161-3170, 1990.
PCT International Search Report and Written Opinion issued in International Application No. PCT/EP2011/004077, dated Nov. 10, 2011.
PCT International Search Report and Written Opinion issued in International Application No. PCT/EP2013/000460, dated Apr. 22, 2013.
PCT International Search Report and Written Opinion issued in International Application No. PCT/EP2013/000459, dated Apr. 23, 2013.
PCT International Search Report and Written Opinion issued in International Application No. PCT/EP2013/000458, dated Apr. 24, 2013.
PCT International Search Report and Written Opinion issued in International Application No. PCT/EP2013/000461, dated Apr. 16, 2013.
Roesler et al "Immunize and disappear—safety-optimized mRNA vaccination with a panel of 29 allergens", *Journal of Allergy and Clinical Immunology*, 124(5):1070-1077, 2009.
Russell et al., "The stability of human beta-globin mRNA is dependent on structural determinants positioned within its 3' untranslated region", Blood, 87:5314-5323, 1996.
Sanchez et al., "Increased levels of polyadenylated histone H2B mRNA accumulate during *Entamoeba invadens* cyst formation", *Molecular and Biochemical Parasitology*, 67(1):137-146, 1994.
Sánchez et al., "The oligo(A) tail on histone mRNA plays an active role in translational silencing of histone mRNA during Xenopus oogenesis", *Mol Cell Biol.*, 24(6):2513-25, 2004.
Stauber et al., "A signal regulating mouse histone H4 mRNA levels in a mammalian cell cycle mutant and sequences controlling RNA 3' processing are both contained within the same 80-bp fragment", EMBO J., 5(12):3297-303, 1986.
Svoboda et al., "Hairpin RNA: a secondary structure of primary importance", Cell Mol Life Sci., 63(7-8):901-8, 2006.
Wagner et al., "A genome-wide RNA interference screen reveals that variant histones are necessary for replication-dependent histone pre-mRNA processing", *Molecular Cell*, 28(4):692-699, 2007.
Weiss et al., "Prophylactic mRNA vaccination against allergy", Current Opinion in Allergy and Clinical Immunology, 10(6):567-574, 2010.
Williams et al., "A simple, highly efficient method for heterologous expression in mammalian primary neurons using cationic lipid-mediated mRNA transfection", *Frontiers in Neuroscience*, 4:1-20, 2010.
Zhong et al., "A double-stranded RNA binding protein required for activation of repressed messages in mammalian germ cells", *Nat Genet.*, 22(2):171-4, 1999.
Cheung et al., "Specific interaction of HeLa cell proteins with coxsackievirus B3 3'UTR: La autoantigen binds the 3' and 5' UTR independently of the poly(A) tail," *Cell Microbiol.*, 9(7):1705-1715, 2007.
Deml et al., "Multiple effects of codon usage optimization on expression and immunogenicity of DNA candidate vaccines encoding the human immunodeficiency virus type 1 Gag protein," Journal of Virology, 75(22):10991-11001, 2001.
Dollé et al., "Nerve growth factor overexpression and autocrine loop in breast cancer cells," *Oncogene*, 22(36):5592-5601, 2003.
Haines et al., "CL22—a novel cationic peptide for efficient transfection of mammalian cells," *Gene Ther.*, 8:99-110, 2001.
Henke et al., "Coxsackievirus B3 vaccines: use as an expression vector for prevention of myocarditis," *Expert Rev. Vaccines*, 7(10):1557-1567, 2008.
Kim et al., "Coxsackievirus B3 used as a gene therapy vector to express functional FGF2," *Gene Ther.*, 19(12):1159-1165, 2012.

(56) References Cited

OTHER PUBLICATIONS

Kim et al., "Systematic analysis of attenuated *Coxsackievirus* expressing a foreign gene as a viral vaccine vector," *Vaccine*, 28(5):1234-1240, 2010.

Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.

Kudla et al., "High guanine and cytosine content increases mRNA levels in mammalian cells," *PLoS Biology*, 4:0933-0942, 2006.

Lorenzi et al., "Intranasal vaccination with messenger RNA as a new approach in gene therapy: use against tuberculosis," *BMC Biotechnology*, 10:77, 2010.

Meier et al., "Fibroblast growth factor-2 but not MEL-CAM and/or β3 integrin promotes progression of melanocytes to melanoma," *Exp. Dermatol.*, 12(3):296-306, 2003.

Office Action issued in U.S. Appl. No. 14/378,538, dated Oct. 11, 2016.

Office Action issued in U.S. Appl. No. 14/378,572, dated Mar. 14, 2017.

Office Action issued in U.S. Appl. No. 14/388,224, dated Oct. 17, 2016.

Office Action issued in U.S. Appl. No. 14/945,349, dated Feb. 6, 2017.

Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.

Palmowski et al., "Intravenous injection of a lentiviral vector encoding NY-ESO-1 induces an effective CTL response," *J. Immunol.*, 172(3):1582-1587, 2004.

Sharma et al., "Functional role of the 5' terminal cloverleaf in Coxsackievirus RNA replication," *Virology*, 393(2):238-249, 2009.

van Ooij et al., "Polyadenylation of genomic RNA and initiation of antigenomic RNA in a positive-strand RNA virus are controlled by the same cis-element," *Nucleic Acids Res.*, 34(10):2953-2965, 2006.

Dhamija et al., "IL-1-induced Post-transcriptional Mechanisms Target Overlapping Translational Silencing and Destabilizing Elements in IKBC mRNA," *J. Biol. Chem.*, 285(38):29165-29178, 2010.

Dugaiczyk et al., "Nucleotide sequence and the encoded amino acids of human serum albumin mRNA," *Proc. Natl. Acad. Sci. USA*, 79:71-75, 1982.

Kübler et al.,"Self-adjuvanted mRNA vaccination in advanced prostate cancer patients: a first-in-man phase I/IIa study," *Journal of ImmunoTherapy of Cancer*, 3:26, 2015.

Office Action issued in U.S. Appl. No. 14/378,572, dated Sep. 21, 2017.

Office Action issued U.S. Appl. No. 14/388,224, dated Jul. 28, 2017.

Office Action issued in U.S. Appl. No. 15/233,933, dated Apr. 6, 2018.

Office Action issued in U.S. Appl. No. 15/233,933, dated Dec. 7, 2017.

Office Action issued in U.S. Appl. No. 15/233,933, dated Jul. 28, 2017.

Office Action issued in U.S. Appl. No. 15/465,322, dated Apr. 2, 2018.

Office Action issued in U.S. Appl. No. 15/465,322, dated Nov. 20, 2017.

Office Action issued in U.S. Appl. No. 15/590,370, dated Apr. 30, 2018.

Office Action issued in U.S. Appl. No. 15/899,326, dated May 23, 2018.

Shen and Higgins, "The 5' untranslated region-mediated enhancement of intracellular listeriolysin O production is required for *Listeria monocytogenes* pathogenicity," *Molecular Microbiology*, 57(5):1460-1473, 2005.

Shuptrine et al., "Monoclonal antibodies for the treatment of cancer," *Seminars in Cancer Biology*, 22:3-13, 2012.

Van Dijk et al., "Identification of RNA sequences and structures involved in site-specific cleavage of IGF-II mRNAs," *RNA*, 1623-1635, 1998.

* cited by examiner

| 90% | 95% | 99% | Cons | #G | #C | #T | #A | |
|---|---|---|---|---|---|---|---|---|
| M* | M* | H* | N* | 25 | 1557 | 172 | 2224 | |
| M* | H* | H* | N* | 16 | 2211 | 188 | 1586 | |
| M | M | H | N | 4 | 875 | 47 | 3075 | |
| M | H | H | N | 6 | 918 | 205 | 2872 | |
| M | M | V | N | 23 | 2675 | 19 | 1284 | |
| S | S | V | N | 3541 | 270 | 6 | 184 | ^ ⎫ |
| G | G | G | G | 4001 | 0 | 0 | 0 | ^ ⎪ |
| V | V | V | N | 25 | 3394 | 569 | 13 | ^ ⎬ Stem 1 |
| V | V | V | N | 27 | 2342 | 1620 | 12 | ^ ⎪ |
| C | V | V | N | 10 | 3783 | 199 | 9 | ^ ⎪ |
| T | T | V | N | 2 | 51 | 3947 | 1 | ^ ⎭ |
| T | T | H | N | 5 | 119 | 3830 | 47 | • ⎫ |
| T | V | H | N | 11 | 227 | 3704 | 59 | • ⎬ Loop |
| T | T | T | T | 0 | 0 | 4001 | 0 | • ⎪ |
| M | M | H | N | 4 | 3140 | 182 | 675 | • ⎭ |
| A | A | R | N | 175 | 7 | 1 | 3818 | v ⎫ |
| G | R | V | N | 3735 | 50 | 21 | 195 | v ⎪ |
| R | R | V | N | 2359 | 31 | 15 | 1596 | v ⎬ Stem 2 |
| R | R | R | N | 3451 | 16 | 11 | 523 | v ⎪ |
| C | C | C | C | 0 | 4001 | 0 | 0 | v ⎪ |
| S | S | B | N | 265 | 3543 | 179 | 14 | v ⎭ |
| A | M | V | N | 112 | 154 | 8 | 3727 | |
| C | C | H | N | 4 | 3870 | 64 | 61 | |
| H* | H* | H* | N* | 37 | 2636 | 557 | 771 | |
| M* | H* | N* | N* | 43 | 1744 | 201 | 2012 | |
| H* | H* | N* | N* | 138 | 674 | 690 | 2499 | |

Figure 1

| #A | #T | #C | #G | Cons | 99% | 95% | 90% | |
|----|----|----|----|------|-----|-----|-----|---|
| 52 | 20 | 45 | 14 | N | N | N | N | |
| 32 | 32 | 59 | 8 | N | N | N | H | |
| 71 | 37 | 20 | 3 | N | N | H | H | |
| 82 | 21 | 25 | 3 | N | N | H | H | |
| 76 | 8 | 38 | 9 | N | N | N | Y | |
| 13 | 3 | 0 | 115 | D | D | R | R | ^ |
| 0 | 0 | 0 | 131 | G | G | G | G | ^ |
| 12 | 21 | 86 | 12 | N | N | N | N | ^ |
| 12 | 85 | 8 | 26 | N | N | N | D | ^ |
| 9 | 58 | 54 | 10 | N | N | N | B | ^ |
| 1 | 86 | 42 | 2 | N | B | Y | Y | ^ |
| 46 | 70 | 13 | 2 | N | N | H | H | • |
| 3 | 65 | 58 | 5 | N | N | B | Y | • |
| 0 | 131 | 0 | 0 | T | T | T | T | • |
| 75 | 28 | 27 | 1 | N | H | H | H | • |
| 82 | 1 | 2 | 46 | N | V | R | R | v |
| 53 | 17 | 6 | 55 | N | N | D | D | v |
| 79 | 13 | 31 | 8 | N | N | N | H | v |
| 20 | 10 | 10 | 91 | N | N | N | N | v |
| 0 | 0 | 131 | 0 | C | C | C | C | v |
| 4 | 15 | 112 | 0 | H | H | Y | Y | v |
| 94 | 7 | 5 | 25 | N | N | D | R | |
| 17 | 31 | 82 | 1 | N | H | H | H | |
| 35 | 32 | 58 | 6 | N | N | N | H | |
| 74 | 20 | 30 | 7 | N | N | N | H | |
| 56 | 28 | 40 | 7 | N | N | N | H | |

Stem 1: rows marked ^
Loop: rows marked •
Stem 2: rows marked v

Figure 2

| #A | #T | #C | #G | Cons | 99% | 95% | 90% | Region |
|---|---|---|---|---|---|---|---|---|
| 2172 | 152 | 1512 | 11 | N* | H* | M* | M* | |
| 1554 | 156 | 2152 | 8 | N* | H* | M* | M* | |
| 3004 | 10 | 855 | 1 | N | M | M | M | |
| 2790 | 184 | 893 | 3 | N | H | M | M | |
| 1208 | 11 | 2637 | 14 | N | M | M | M | |
| 171 | 3 | 270 | 3426 | N | Y | S | S | ^ Stem 1 |
| 0 | 0 | 0 | 3870 | G | G | G | G | ^ |
| 1 | 548 | 3308 | 13 | N | Y | Y | Y | ^ |
| 0 | 1535 | 2334 | 1 | B | Y | Y | Y | ^ |
| 0 | 141 | 3729 | 0 | Y | Y | C | C | ^ |
| 0 | 3861 | 9 | 0 | Y | T | T | T | ^ |
| 1 | 3760 | 106 | 3 | N | Y | T | T | • Loop |
| 56 | 3639 | 169 | 6 | N | H | Y | T | • |
| 0 | 3870 | 0 | 0 | T | T | T | T | • |
| 600 | 154 | 3113 | 3 | N | H | M | M | • |
| 3736 | 0 | 5 | 129 | Y | R | A | A | v Stem 2 |
| 142 | 4 | 44 | 3680 | N | Y | C | C | v |
| 1517 | 2 | 0 | 2351 | D | R | R | R | v |
| 503 | 1 | 6 | 3360 | N | R | R | R | v |
| 0 | 0 | 3870 | 0 | C | C | C | C | v |
| 10 | 164 | 3431 | 265 | N | B | S | S | v |
| 3633 | 1 | 149 | 87 | N | Y | M | A | |
| 44 | 33 | 3788 | 3 | N | M | C | C | |
| 736 | 525 | 2578 | 31 | N* | H* | H* | H* | |
| 1938 | 181 | 1714 | 36 | N* | H* | H* | M* | |
| 2443 | 662 | 634 | 131 | N* | N* | H* | H* | |

Figure 3

| 90% | 95% | 99% | Cons | #G | #C | #T | #A | Structure |
|---|---|---|---|---|---|---|---|---|
| M* | H* | H* | N* | 8 | 601 | 63 | 661 | |
| M* | H* | H* | N* | 4 | 1062 | 121 | 146 | |
| A | A | M | H | 0 | 16 | 2 | 1315 | |
| A | A | A | N | 2 | 6 | 2 | 1323 | |
| M | M | M | N | 4 | 403 | 6 | 920 | |
| C | C | C | N | 1322 | 1 | 2 | 8 | ∧ |
| C | C | C | C | 1333 | 0 | 0 | 0 | ∧ |
| C | C | Y | H | 0 | 1293 | 39 | 1 | ∧ |
| T | Y | Y | Y | 0 | 116 | 1217 | 0 | ∧ |
| C | C | C | Y | 0 | 1331 | 2 | 0 | ∧ |
| T | T | T | Y | 0 | 2 | 1331 | 0 | ∧ |
| T | T | T | D | 3 | 0 | 1329 | 1 | • |
| T | Y | Y | N | 1 | 121 | 1207 | 4 | • |
| T | T | T | T | 0 | 0 | 1333 | 0 | • |
| M | M | H | H | 0 | 862 | 30 | 441 | • |
| A | A | A | A | 0 | 0 | 0 | 1333 | ∨ |
| G | G | G | B | 1330 | 2 | 1 | 0 | ∨ |
| R | R | R | R | 134 | 0 | 0 | 1199 | ∨ |
| G | G | R | D | 1311 | 0 | 1 | 21 | ∨ |
| C | C | C | C | 0 | 1333 | 0 | 0 | ∨ |
| C | C | C | N | 2 | 1328 | 2 | 1 | ∨ |
| M | Y | Y | N | 78 | 128 | 1 | 1126 | |
| C | C | H | N | 1 | 1284 | 22 | 26 | |
| Y* | H* | N* | N* | 18 | 1143 | 91 | 81 | |
| M* | H* | N* | N* | 28 | 834 | 91 | 380 | |
| M* | M* | M* | H* | 0 | 361 | 12 | 960 | |

Stem 1 spans rows marked ∧; Loop spans rows marked •; Stem 2 spans rows marked ∨.

Figure 4

| #A | #T | #C | #C | Cons | 99% | 95% | 90% | |
|---|---|---|---|---|---|---|---|---|
| 10 | 8 | 62 | 4 | N* | N* | H* | H* | |
| 17 | 6 | 61 | 0 | H* | H* | H* | M* | |
| 84 | 0 | 0 | 0 | A | A | A | A | |
| 84 | 0 | 0 | 0 | A | A | A | A | |
| 76 | 2 | 6 | 0 | H | H | M | A | |
| 1 | 2 | 0 | 81 | D | D | G | G | ^ |
| 0 | 0 | 0 | 84 | C | C | C | C | ^ |
| 1 | 1 | 82 | 0 | H | H | C | C | ^ |
| 0 | 67 | 17 | 0 | Y | Y | Y | Y | ^ |
| 0 | 0 | 84 | 0 | C | C | C | C | ^ |
| 0 | 84 | 0 | 0 | T | T | T | T | ^ |
| 1 | 80 | 0 | 3 | D | D | T | T | • |
| 0 | 81 | 3 | 0 | Y | Y | T | T | • |
| 0 | 84 | 0 | 0 | T | T | T | T | • |
| 12 | 5 | 67 | 0 | H | H | H | M | • |
| 84 | 0 | 0 | 0 | A | A | A | A | v |
| 0 | 0 | 1 | 83 | S | S | G | G | v |
| 65 | 0 | 0 | 19 | R | R | R | R | v |
| 3 | 0 | 0 | 81 | R | R | G | G | v |
| 0 | 0 | 84 | 0 | C | C | C | C | v |
| 0 | 0 | 84 | 0 | C | C | C | C | v |
| 69 | 0 | 5 | 10 | V | V | V | R | |
| 5 | 4 | 75 | 0 | H | H | M | M | |
| 0 | 25 | 57 | 2 | B* | B* | Y* | Y* | |
| 10 | 24 | 44 | 6 | N* | N* | N* | H* | |
| 64 | 3 | 17 | 0 | H* | H* | M* | M* | |

Stem 1 brackets rows 6–11; Loop brackets rows 12–15; Stem 2 brackets rows 16–21.

Figure 5 ppLuc(GC) – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagauc-3'

Figure 6 ppLuc(GC) – ag – A64 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAA-3'

Figure 7 ppLuc(GC) – ag – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuCAAAGGCUCUUUUCAGAGCCACCA-3'

Figure 8 ppLuc(GC) – ag – A64 – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
gacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAAugcauCAAAGGCUCUUUUCAGAGCCACCA-3'

Figure 9 ppLuc(GC) – ag – A120 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAA
AAAAAAAAA-3'

Figure 10 ppLuc(GC) – ag – A64 – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCCUGCCCGAUGGGCCUCCCAACGGGCCCUCCUCCCCUCCUUGCACCG3'

Figure 11 ppLuc(GC) – ag – A64 – aCPSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAAAAAAAA
AAAAAugcau*CAAUUCCUACACGUGAGGCGCUGUGAUUCCCUAUCCCCCUUCAUUCCCU*
*AUACAUUAGCACAGCGCCAUUGCAUGUAGGAAUU*-3'

Figure 12 ppLuc(GC) – ag – A64 – PolioCL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAAA
AAAAAugcau*CAAUUCUAAAACAGCUCUGGGGUUGUACCCACCCCAGAGGCCCACGUGG*
*CGGCUAGUACUCCGGUAUUGCGGUACCCUUGUACGCCUGUUUUAGAAUU*-3'

Figure 13 ppLuc(GC) – ag – A64 – G30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAAA
AAAAAAugcau*GGGGGGGGGGGGGGGGGGGGGGGGGGGGGG*-3'

Figure 14 ppLuc(GC) – ag – A64 – U30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAAA
AAAAAAugca*UUUUUUUUUUUUUUUUUUUUUUUUUUUUUU*-3'

Figure 15 ppLuc(GC) – ag – A64 – SL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGCGGCAAGAUCGCCGUGAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*UAUGGCGGCCGUGUCCACCACGGAUAUCACCGUGGUGGACGCGGCC-3'*

Figure 16 ppLuc(GC) – ag – A64 – N32 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCCCCCUCUAGACAAUUGGAAUUCCAUA-3'

Figure 17

MmMOG(wt) – ag – A64 – C30 gggagaaagcuuaccAUGGCCUGUUUGUGGAGCUUCUCUUGGCCCAGCUGCUUCCUCUCC
CUUCUCCUCCUUCUCCUCCAGUUGUCAUGCAGCUAUGCAGGACAAUUCAGAGUGAUAGGA
CCAGGGUAUCCCAUCCGGGCUUUAGUUGGGGAUGAAGCAGAGCUGCCGUGCCGCAUCUCU
CCUGGGAAAAAUGCCACGGGCAUGGAGGUGGGUUGGUACCGUUCUCCCUUCUCAAGAGUG
GUUCACCUCUACCGAAAUGGCAAGGACCAAGAUGCAGAGCAAGCACCUGAAUACCGGGGA
CGCACAGAGCUUCUGAAAGAGACUAUCAGUGAGGGAAAGGUUACCCUUAGGAUUCAGAAC
GUGAGAUUCUCAGAUGAAGGAGGCUACACCUGCUUCUUCAGAGACCACUCUUACCAAGAA
GAGGCAGCAAUGGAGUUGAAAGUGGAAGAUCCCUUCUAUUGGGUCAACCCCGGUGUGCUG
ACUCUCAUCGCACUUGUGCCUACGAUCCUCCUGCAGGUCCCUGUAGGCCUUGUAUUCCUC
UUCCUGCAGCACAGACUGAGAGGAAAACUUCGUGCAGAAGUAGAGAAUCUCCAUCGGACU
UUUGAUCCUCACUUCCUGAGGGUGCCCUGCUGGAAGAUAACACUGUUUGUUAUUGUGCCU
GUUCUUGGACCCCUGGUUGCCUUGAUCAUCUGCUACAACUGGCUGCACCGAAGACUGGCA
GGACAGUUUCUUGAAGAGCUAAGAAACCCCUUUUGAccacuaguuauaagacugacua**GC
CCGAUGGGCCUCCCAACGGGCCUCCUCCCCUCCUUGCACCG**agauuaauAAAAAAAAAA
AAAAAAAAAAAAAAAAAAAAAAAAAAAAAAAAAAAAAAAAAAAAAAAAAAAAAUAUUCC
CCCCCCCCCCCCCCCCCCCCCCCCCCucuagacaauuggaauu

Figure 18

MmMOG(wt) – ag – A64 – C30 - histoneSL gggagaaagcuuaccAUGGCCUGUUUGUGGAGCUUCUCUUGGCCCAGCUGCUUCC
UCUCCCUUCUCCUCCUUCUCCUCCAGUUGUCAUGCAGCUAUGCAGGACAAUUC
AGAGUGAUAGGACCAGGGUAUCCCAUCCGGGCUUUAGUUGGGGAUGAAGCAGA
GCUGCCGUGCCGCAUCUCUCCUGGGAAAAAUGCCACGGGCAUGGAGGUGGGUU
GGUACCGUUCUCCCUUCUCAAGAGUGGUUCACCUCUACCGAAAUGGCAAGGAC
CAAGAUGCAGAGCAAGCACCUGAAUACCGGGGACGCACAGAGCUUCUGAAAGA
GACUAUCAGUGAGGGAAAGGUUACCCUUAGGAUUCAGAACGUGAGAUUCUCAG
AUGAAGGAGGCUACACCUGCUUCUUCAGAGACCACUCUUACCAAGAAGAGGCA
GCAAUGGAGUUGAAAGUGGAAGAUCCCUUCUAUUGGGUCAACCCCGGUGUGCU
GACUCUCAUCGCACUUGUGCCUACGAUCCUCCUGCAGGUCCCUGUAGGCCUUG
UAUUCCUCUUCCUGCAGCACAGACUGAGAGGAAAACUUCGUGCAGAAGUAGAG
AAUCUCCAUCGGACUUUUGAUCCUCACUUCCUGAGGGUGCCCUGCUGGAAGAU
AACACUGUUUGUUAUUGUGCCUGUUCUUGGACCCCUGGUUGCCUUGAUCAUCU
GCUACAACUGGCUGCACCGAAGACUGGCAGGACAGUUUCUUGAAGAGCUAAGA
AACCCCUUUUGAccacuaguuauaagacugacuaGCCCGAUGGGCCUCCCAACG
GGCCCUCCUCCCCUCCUUGCACCGagauuaauAAAAAAAAAAAAAAAAAAAAAAAAAAAA
AAAAAAAAAAAAAAAAAAAAAAAAAAAAAAAAAAAAUGCAUCCCCCCCCCCCCCCCCC
CCCCCCCCCCCAAAGGCUCUUUUCAGAGCCACCAggaauu

Figure 19

SEQUENCE LISTING

```
<160> NUMBER OF SEQ ID NOS: 56

<210> SEQ ID NO 1
<211> LENGTH: 16
<212> TYPE: RNA
<213> ORGANISM: artificial
<220> FEATURE:
<223> OTHER INFORMATION: histone stem-loop sequence according to formula
      (Ic): metazoan and protozoan histone stem-loop consensus sequence
      without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 1
ngnnnnnnun nnnncn                                                    16

<210> SEQ ID NO 2
<211> LENGTH: 26
<212> TYPE: RNA
<213> ORGANISM: artificial
<220> FEATURE:
<223> OTHER INFORMATION: histone stem-loop sequence according to formula
      (IIc): metazoan and protozoan histone stem-loop consensus sequence
      with stem bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
```

```
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 2
nnnnnngnnn nnnunnnnnc nnnnnn                                              26

<210> SEQ ID NO 3
<211> LENGTH: 16
<212> TYPE: RNA
<213> ORGANISM: artificial
<220> FEATURE:
<223> OTHER INFORMATION: histone stem-loop sequence according to formula
      (Id): without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 3
ncnnnnnnun nnnngn                                                         16

<210> SEQ ID NO 4
<211> LENGTH: 26
<212> TYPE: RNA
<213> ORGANISM: artificial
<220> FEATURE:
<223> OTHER INFORMATION: histone stem-loop sequence according to formula
      (IId): with stem bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof
```

```
<400> SEQUENCE: 4
nnnnnncnnn nnnunnnnng nnnnnn                                          26

<210> SEQ ID NO 5
<211> LENGTH: 16
<212> TYPE: RNA
<213> ORGANISM: artificial
<220> FEATURE:
<223> OTHER INFORMATION: histone stem-loop sequence according to formula
      (Ie): protozoan histone stem-loop consensus sequence without stem
      bordering elements
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof

<400> SEQUENCE: 5
dgnnnnnnun nnnnch                                                     16

<210> SEQ ID NO 6
<211> LENGTH: 26
<212> TYPE: RNA
<213> ORGANISM: artificial
<220> FEATURE:
<223> OTHER INFORMATION: histone stem-loop sequence according to formula
      (IIe): protozoan histone stem-loop consensus sequence with stem
      bordering elements
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(26)
<223> OTHER INFORMATION: n is selected from a nucleotide selected from
      A, U, T, G and C, or a nucleotide analogue thereof

<400> SEQUENCE: 6
nnnnndgnnn nnnunnnnnc hnnnnn                                          26

<210> SEQ ID NO 7
<211> LENGTH: 16
<212> TYPE: RNA
<213> ORGANISM: artificial
<220> FEATURE:
<223> OTHER INFORMATION: histone stem-loop sequence according to formula
      (If): metazoan histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(3)
```

```
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(12)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (14)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 7
ngnbyynnun vndncn                                                     16

<210> SEQ ID NO 8
<211> LENGTH: 26
<212> TYPE: RNA
<213> ORGANISM: artificial
<220> FEATURE:
<223> OTHER INFORMATION: histone stem-loop sequence according to formula
      (IIf): metazoan histone stem-loop consensus sequence with stem
      bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(15)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(17)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 8
```
nnnnnngnby ynnunvndnc nnnnnn        26

<210> SEQ ID NO 9
<211> LENGTH: 16
<212> TYPE: RNA
<213> ORGANISM: artificial
<220> FEATURE:
<223> OTHER INFORMATION: histone stem-loop sequence according to formula
      (Ig): vertebrate histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 9
nghyyydnuh abrdcn        16

<210> SEQ ID NO 10
<211> LENGTH: 26
<212> TYPE: RNA
<213> ORGANISM: artificial
<220> FEATURE:
<223> OTHER INFORMATION: histone stem-loop sequence according to formula
      (IIg): vertebrate histone stem-loop consensus sequence with stem
      bordering elements
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (4)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(25)
<223> OTHER INFORMATION: n is selected from a nucleotide selected from
      A, U, T, G and C, or a nucleotide analogue thereof

<400> SEQUENCE: 10
nnhnnnghyy ydnuhabrdc nnnnnh        26

<210> SEQ ID NO 11
<211> LENGTH: 16
<212> TYPE: RNA
<213> ORGANISM: artificial
<220> FEATURE:
<223> OTHER INFORMATION: histone stem-loop sequence according to formula
      (Ih): humane histone stem-loop consensus sequence (Homo sapiens)
      without stem bordering elements

<400> SEQUENCE: 11
dghycudyuh asrrcc        16

```
<210> SEQ ID NO 12
<211> LENGTH: 26
<212> TYPE: RNA
<213> ORGANISM: artificial
<220> FEATURE:
<223> OTHER INFORMATION: histone stem-loop sequence according to formula
      (IIh): human histone stem-loop consensus sequence (Homo sapiens)
      with stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 12
nhaahdghyc udyuhasrrc cvhbnh                                          26

<210> SEQ ID NO 13
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 13
vgyyyyhhth rvvrcb                                                     16

<210> SEQ ID NO 14
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 14
sgyyyttytm arrrcs                                                     16

<210> SEQ ID NO 15
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 15 sgyyctttm agrrcs                                                      16

<210> SEQ ID NO 16
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
```

```
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(14)
<223> OTHER INFORMATION: n is selected from a nucleotide selected from
      A, U, T, G and C, or a nucleotide analogue thereof

<400> SEQUENCE: 16
dgnnnbnnth vnnnch                                                   16

<210> SEQ ID NO 17
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(14)
<223> OTHER INFORMATION: n is selected from a nucleotide selected from
      A, U, T, G and C, or a nucleotide analogue thereof

<400> SEQUENCE: 17
rgnnnyhbth rdnncy                                                   16

<210> SEQ ID NO 18
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(3)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (14)..(14)
<223> OTHER INFORMATION: n is selected from a nucleotide selected from
      A, U, T, G and C, or a nucleotide analogue thereof

<400> SEQUENCE: 18
rgndbyhyth rdhncy                                                   16

<210> SEQ ID NO 19
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 19
vgyyytyhth rvrrcb                                                   16

<210> SEQ ID NO 20
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)
```

```
<400> SEQUENCE: 20
sgyycttytm agrrcs                                                     16

<210> SEQ ID NO 21
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 21
sgyycttttm agrrcs                                                     16

<210> SEQ ID NO 22
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 22
ggyycttyth agrrcc                                                     16

<210> SEQ ID NO 23
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 23
ggcycttytm agrgcc                                                     16

<210> SEQ ID NO 24
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 24
ggctcttttm agrgcc                                                     16

<210> SEQ ID NO 25
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 25
dghyctdyth asrrcc                                                     16

<210> SEQ ID NO 26
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)
```

```
<400> SEQUENCE: 26
ggcyctttth agrgcc                                              16

<210> SEQ ID NO 27
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 27
ggcycttttm agrgcc                                              16

<210> SEQ ID NO 28
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 28
hhhhvvgyyy yhhthrvvrc bvhhnn                                   26

<210> SEQ ID NO 29
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)

<400> SEQUENCE: 29
mhmhmsgyyy ttytmarrrc smchhh                                   26

<210> SEQ ID NO 30
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)

<400> SEQUENCE: 30
mmmmmsgyyc ttttmagrrc sachmh                                   26

<210> SEQ ID NO 31
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
```

```
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(22)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (24)..(26)
<223> OTHER INFORMATION: n is selected from a nucleotide selected from
      A, U, T, G and C, or a nucleotide analogue thereof

<400> SEQUENCE: 31
nnnnndgnnn bnnthvnnnc hnhnnn                                          26

<210> SEQ ID NO 32
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (5)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (18)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 32
nnhhnrgnnn yhbthrdnnc ydhhnn                                          26

<210> SEQ ID NO 33
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
```

```
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof

<400> SEQUENCE: 33
nhhhvrgndb yhythrdhnc yrhhhh                                          26

<210> SEQ ID NO 34
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)
<220> FEATURE:
<221> NAME/KEY: misc_feature
<222> LOCATION: (26)..(26)
<223> OTHER INFORMATION: n is selected from a nucleotide selected from
      A, U, T, G and C, or a nucleotide analogue thereof

<400> SEQUENCE: 34
hhmhmvgyyy tyhthrvrrc bvmhhn                                          26

<210> SEQ ID NO 35
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 35
mmmmmsgyyc ttytmagrrc smchhh                                          26

<210> SEQ ID NO 36
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 36
mmmmmsgyyc ttttmagrrc sachmh                                          26

<210> SEQ ID NO 37
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)
<220> FEATURE:
<221> NAME/KEY: misc_feature
<222> LOCATION: (24)..(25)
<223> OTHER INFORMATION: n is selected from a nucleotide selected from
      A, U, T, G and C, or a nucleotide analogue thereof

<400> SEQUENCE: 37
hhmamggyyc ttythagrrc cvhnnm                                          26

<210> SEQ ID NO 38
<211> LENGTH: 26
<212> TYPE: DNA
<213> ORGANISM: artificial
```

```
<220> FEATURE:
<223> OTHER INFORMATION: histone stem-loop sequence (with stem bordering
      elements) according to formula (IIg)

<400> SEQUENCE: 38
hhaamggcyc ttytmagrgc cvchhm                                              26

<210> SEQ ID NO 39
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)

<400> SEQUENCE: 39
mmaamggctc ttttmagrgc cmcymm                                              26

<210> SEQ ID NO 40
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 40
nhaahdghyc tdythasrrc cvhbnh                                              26

<210> SEQ ID NO 41
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 41
hhaamggcyc tttthagrgc cvmynm                                              26

<210> SEQ ID NO 42
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)

<400> SEQUENCE: 42
hmaaaggcyc ttttmagrgc crmyhm                                              26

<210> SEQ ID NO 43
<211> LENGTH: 1747
<212> TYPE: RNA
```

<213> ORGANISM: artificial
<220> FEATURE:
<223> OTHER INFORMATION: mRNA sequence of ppLuc(GC)-ag

<400> SEQUENCE: 43

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc gugguguccu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu gguguucgug agcaagaagg ccugcagaa     420
gauccugaac gugcagaaga gcugcccau cauccagaag aucaucauca uggacagcaa     480
gaccgacuac cagggcuucc agucgaugua cacguucgug accagccacc ucccgccggg     540
cuucaacgag uacgacuucg ucccggagag cuucgaccgg gacaagacca ucgcccugau     600
caugaacagc agcggcagca ccggccugcc gaagggggug gcccugccgc accggaccgc     660
cugcgugcgc uucucgcacg cccgggaccc caucuucggc aaccagauca ucccggacac     720
cgccauccug agcgugguc cguuccacca cggcuucggc auguucacga cccugggcua     780
ccucaucugc ggcuuccggg uggccugau guaccgguuc gaggaggagc uguuccugcg     840
gagccugcag gacuacaaga uccagagcgc gcugcucgug ccgacccugu cagcuucuu     900
cgccaagagc acccugaucg acaaguacga ccugucgaac cugcacgaga ucgccagcgg     960
gggcgccccg cugagcaagg aggugggcga ggccguggcc aagcgguucc accucccggg    1020
cauccgccag ggcuacggcc ugaccgagac cacgagcgcg auccugauca ccccgagg     1080
ggacgacaag ccgggcgccg ugggcaaggu gguccgguuc uucgaggcca ggugguga    1140
ccuggacacc ggcaagaccc uggggcgugaa ccagcggggc gagcugugcg ucgggggcc    1200
gaugaucaug agcggcuacg ugaacaaccc ggaggccacc aacgcccuca ucgacaagga    1260
cggcuggcug cacagcggcg acaucgccua cuggacgag gacgagcacu ucuucaucgu    1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggccccuccuc cccucuuugc accgagauua   1740
auagauc                                                              1747
```

<210> SEQ ID NO 44
<211> LENGTH: 1806
<212> TYPE: RNA
<213> ORGANISM: artificial
<220> FEATURE:
<223> OTHER INFORMATION: mRNA sequence of ppLuc(GC)-ag-A64

<400> SEQUENCE: 44

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
```

```
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc guggugugcu cggagaacag ccugcaguuc uucaugccgg ugcugggcgc      300
ccucuucauc ggcguggccg ucgccccggc gaacgacauc uacaacgagc gggagcugcu      360
gaacagcaug gggaucagcc agccgaccgu ggucuucgug agcaagaagg gccugcagaa      420
gauccugaac gugcagaaga agcugcccau cauccgaaag aucaucauca uggacagcaa      480
gaccgacuac cagggcuucc agucgaugua cacguucgug accagccacc ucccgccggg      540
cuucaacgag uacgacuucg ucccggagag cuucgaccgg acaagacca ucgcccugau       600 caugaacagc agcggcagca ccggccugcc gaaggggug gcccugccgc accggaccgc       660
cugcgugcgc uucucgcacg cccgggaccc caucuucggc aaccagauca ucccggacac      720
cgccauccug agcguggugc cguuccacca cggcuucggc auguucacga cccugggcua      780
ccucaucugc ggcuuccggg uggccugau guaccgguuc gaggaggagc uguuccugcg       840
gagccugcag gacuacaaga uccagagcgc gcugcucgug ccgacccugu ucagcuucuu      900
cgccaagagc acccugaucg acaaguacga ccugucgaac cugcacgaga ucgccagcgg      960
gggcgccccg cugagcaagg aggugggcga ggccguggcc aagcgguucc accucccggg     1020
cauccgccag ggcuacggcc ugaccgagac cacgagcgcg auccugauca cccccgaggg     1080
ggacgacaag ccgggcgccg ugggcaaggu ggucccguuc uucgaggcca ggguggugga     1140
ccuggacacc ggcaagaccc ugggcgugaa ccagcggggc gagcugugcg ugcgggggcc     1200
gaugaucaug agcggcuacg ugaacaaccc ggaggccacc aacgcccuca ucgacaagga     1260
cggcuggcug cacagcggcg acaucgccua cugggacgag gacgagcacu ucuucaucgu     1320
cgaccggcug aagucgcuga ucaaguacaa gggcuaccag guggcgccgg ccgagcugga     1380
gagcauccug cuccagcacc ccaacaucuu cgacgccggc guggccgggc ugccggacga     1440
cgacgccggc gagcugccgg ccgcggugu ggugcuggag cacggcaaga ccaugacgga      1500
gaaggagauc gucgacuacg uggccagcca ggugaccacc gccaagaagc ugcggggcgg     1560
cguggucuuc guggacgagg ucccgaaggg ccugaccggg aagcucgacg cccggaagau     1620
ccgcgagauc cugaucaagg ccaagaaggg cggcaagauc gccguguaag acuaguuaua     1680
agacugacua gcccgauggg ccucccaacg ggcccuccuc cccuccuugc accgagauua     1740
auaaaaaaaa aaaaaaaaaa aaaaaaaaaa aaaaaaaaaa aaaaaaaaaa aaaaaaaaaa     1800
aaaaaa                                                                1806
```

<210> SEQ ID NO 45
<211> LENGTH: 1772
<212> TYPE: RNA
<213> ORGANISM: artificial
<220> FEATURE:
<223> OTHER INFORMATION: mRNA sequence of ppLuc(GC)-ag-histoneSL

<400> SEQUENCE: 45

```
gggagaaagc uugaggaugg aggacgccaa gaacaucaag aagggcccgg cgcccuucua       60
cccgcuggag gacgggaccg ccggcgagca gcuccacaag gccaugaagc gguacgcccu      120
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc guggugugcu cggagaacag ccugcaguuc uucaugccgg ugcugggcgc      300
```

```
ccucuucauc ggcguggccg ucgccccggc gaacgacauc uacaacgagc gggagcugcu    360
gaacagcaug gggaucagcc agccgaccgu gguguucgug agcaagaagg ccugcagaa     420 gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccugcc gaaggggggug gcccugccgc accgaccgc    660 cugcgugcgc uucucgcacg cccgggaccc cauucucggc aaccagauca ucccggacac    720
cgccauccug agcgugugugc cguuccacca cggcuucggc auguucacga cccugggcua    780
ccucaucugc ggcuuccggg uggccugau guaccgguuc gaggaggagc uguuccugcg     840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu gguccccguuc uucgaggcca aggugguga    1140 ccuggacacc ggcaagaccc uggggcugaa ccagcggggc gagcugugcg ugcggggggcc   1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560 cguggugune guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggccccuccu cccuccuugc accgagauua   1740
auagaucuca aaggcucuuu ucagagccac ca                                 1772
```

<210> SEQ ID NO 46
<211> LENGTH: 1835
<212> TYPE: RNA
<213> ORGANISM: artificial
<220> FEATURE:
<223> OTHER INFORMATION: mRNA sequence of ppLuc(GC)-ag-A64-histoneSL

<400> SEQUENCE: 46

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu gguguucgug agcaagaagg ccugcagaa     420 gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
```

```
caugaacagc agcggcagca ccggccugcc gaaggggug gcccugccgc accggaccgc    660
cugcgugcgc uucucgcacg cccgggaccc caucuucggc aaccagauca ucccggacac    720
cgccauccug agcguggugc cguuccacca cggcuucggc auguucacga cccugggcua    780 ccucaucucug ggcuuccggg uggaccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agguggcgcga ggccguggcc aagcgguucc accucccggg   1020 caucgccag ggcuacggcc ugaccgagac cacgagcgcg auccugauca ccccgaggg    1080 ggacgacaag ccgggcgccg ugggcaaggu ggucccguuc uucgaggcca ggugguggga   1140
ccuggacacc ggcaagaccc uggggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cuggacgag gacgagcacu cuucaucgu    1320 cgaccggcug aagucgcuga ucaaguacaa gggcuaccag gugggcgccgg ccgagcugga   1380 gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcgggggcgg   1560 cguggguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggccccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca ucaaaggcuc uuuucagagc cacca                             1835

<210> SEQ ID NO 47
<211> LENGTH: 1869
<212> TYPE: RNA
<213> ORGANISM: artificial
<220> FEATURE:
<223> OTHER INFORMATION: mRNA sequence of ppLuc(GC)-ag-A120

<400> SEQUENCE: 47
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgcg gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggguuucgu agcaagaagg gccugcagaa    420
gauccugaac gugcagaaga gcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau    600 caugaacagc agcggcagca ccggccugcc gaagggggug gcccugccgc accggaccgc    660
cugcgugcgc uucucgcacg cccgggaccc caucuucggc aaccagauca ucccggacac    720
cgccauccug agcguggugc cguuccacca cggcuucggc auguucacga cccugggcua    780
```

```
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agguggggcga ggccgguggcc aagcgguucc accucccggg  1020
caucgccag ggcuacggcc ugaccgagac cacgagcgcg auccugauca cccccgaggg    1080
ggacgacaag ccgggcgccg ugggcaaggu ggucccguuc uucgaggcca aggugguggaa 1140
ccuggacacc ggcaagaccc ugggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggugulc guggacgagg ucccgaaggg ccugaccggg aagcucgacg cccggaagau   1620
ccgcgagauc cugaucaagg ccaagaaggg cggcaagauc ccguguaag acuaguuaua   1680
agacugacua gcccgauggg ccucccaacg ggccccuccuc cccccuugc accgagauua   1740
auagaucuaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaa                                                           1869
```

<210> SEQ ID NO 48
<211> LENGTH: 1858
<212> TYPE: RNA
<213> ORGANISM: artificial
<220> FEATURE:
<223> OTHER INFORMATION: mRNA sequence of ppLuc(GC)-ag-A64-ag

<400> SEQUENCE: 48

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga   180
guacuucgag augagcgugc gccuggccga ggccaugaag cgguacggcc ugaacaccaa   240
ccaccggauc gugugugcu cggagaacag ccugcaguuc uucaugccgg ugcugggcgc   300
ccucuucauc ggcguggccg ucgccccggc gaacgacauc uacaacgagc gggagcugcu   360
gaacagcaug gggaucagcc agccgaccgu gguguucgug agcaagaagg gccugcagaa   420
gaucccugaac gugcagaaga gcugcccau cauccagaag aucaucauca uggacagcaa   480
gaccgacuac cagggcuucc agucgaugua cacgguucgug accagccacc ucccgccggg   540
cuucaacgag uacgacuucg ucccggagag cuucgaccgg gacaagacca ucgcccugau   600
caugaacagc agcggcagca ccggccugcc gaaggggggug gcccugccgc accggaccgc   660
cugcgugcgc uucucgcacg ccgggaccc caucuucgc aaccgaucca uccggacac     720
cgccauccug agcgugugc guuccacca cggcuucggc auguuucacga cccugggcua   780
ccucaucugc ggcuuccggg ugguccuggau guaccgguuc gaggaggagc uguuccugcg   840
gagccugcag gacuacaaga uccagagcgc gcugcucgug ccgaccucgu ucagcuucuu    900
cgccaagagc acccugaucg acaaguacga ccugucgaac cugcacgaga ucgccagcgg   960
```

```
gggcgccccg cugagcaagg aggugggcga ggccguggcc aagcgguucc accucccggg      1020
cauccgccag ggcuacggcc ugaccgagac cacgagcgcg auccugauca cccccgaggg      1080
ggacgacaag ccgggcgccg ugggcaaggu gguccccguuc uucgaggcca aggugguga      1140 ccuggacacc ggcaagaccc ugggcgugaa ccagcggggc gagcugugcg ugcggggggcc     1200 gaugaucaug agcggcuacg ugaacaaccc ggaggccacc aacgcccuca ucgacaagga      1260
cggcuggcug cacagcggcg acaucgccua cugggacgag gacgagcacu ucuucaucgu      1320
cgaccggcug aagucgcuga ucaaguacaa gggcuaccag guggcgccgg ccgagcugga      1380
gagcauccgc cuccagcacc ccaacaucuu cgacgccggc guggccgggc ugccggacga      1440
cgacgccggc gagcugccgg ccgcgguggu ggugcuggag cacggcaaga ccaugacgga      1500
gaaggagauc gucgacuacg uggccagcca ggugaccacc gccaagaagc ugcggggcgg      1560
cguggucuuc guggacgagg ucccgaaggg ccugaccggg aagcucgacg cccggaagau      1620
ccgcgagauc cugaucaagg ccaagaaggg cggcaagauc gccguguaag acuaguuaua      1680
agacugacua gcccgauggg ccucccaacg ggccccuccu cccuccuugc accgagauua      1740
auaaaaaaaa aaaaaaaaaa aaaaaaaaaa aaaaaaaaaa aaaaaaaaaa aaaaaaaaaa      1800
aaaaaaugca uccugcccga ugggccuccc aacgggcccu ccucccccucc uugcaccg      1858
```

<210> SEQ ID NO 49
<211> LENGTH: 1894
<212> TYPE: RNA
<213> ORGANISM: artificial
<220> FEATURE:
<223> OTHER INFORMATION: mRNA sequence of ppLuc(GC)-ag-A64-aCPSL

<400> SEQUENCE: 49

```
gggagaaagc uugaggaugg aggacgccaa gaacaucaag aagggccccgg cgcccuucua     60 cccgcuggag acgggaccg ccggcgagca gcuccacaag gccaugaagc gguacgcccu       120
ggugccgggc acgaucgccu ucaccgacgc ccacaucgag gucgacauca ccuacgcgga      180
guacuucgag augagcgugc gccuggccga ggccaugaag cgguacgcc ugaacaccaa       240 ccaccggauc guggugugcu cggagaacag ccugcaguuc uucaugccgg ugcugggcgc      300
ccucuucauc ggcguggccg ucgccccggc gaacgacauc uacaacgagc gggagcugcu      360
gaacagcaug gggaucagcc agccgaccgu ggguguucgug agcaagaagg ccugcagaa       420 gauccugaac gugcagaaga gcugcccau cauccagaag aucaucauca uggacagcaa      480
gaccgacuac cagggcuucc agucgaugua cacguucgug accagccacc uccgccgggg     540
cuucaacgag uacgacuucg ucccggagag cuucgaccgg acaagacca ucgcccugau     600 caugaacagc agcggcagca ccggccgcc gaaggggggug gcccugccgc accgaccgc     660 cugcgugcgc uucucgcacg cccgggaccc caucuucggc aaccagauca cccggacac     720 cgccauccug agcguggugc cguuccacca cggcuucggc auguucacga cccugggcua    780
ccucaucugc ggcuuccggg uggccugau gaccgguuc gaggaggagc uguccugcg        840 gagccugcag acuacaaga uccgagcgc gcucucgug ccgacccgu ucagcuucu        900 cgccaagagc accccugaucg acaaguacga ccugucgaac cugcacgaga ucgccagcgg     960
```

```
ccuggacacc ggcaagaccc ugggcgugaa ccagcggggc gagcugugcg ugcggggcc     1200 gaugaucaug agcggcuacg ugaacaaccc ggaggccacc aacgcccuca ucgacaagga    1260
cggcuggcug cacagcggcg acaucgccua cuggacgag gacgagcacu ucuucaucgu     1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggucuuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccugc accgagauua     1740 auaaaaaaaa aaaaaaaaaa aaaaaaaaaa aaaaaaaaaa aaaaaaaaaa aaaaaaaaaa    1800
aaaaaaugca ucaauuccua cacgugaggc gcugugauuc ccuauccccc uucauucccu    1860
auacauuagc acagcgccau ugcauguagg aauu                                1894
```

<210> SEQ ID NO 50
<211> LENGTH: 1909
<212> TYPE: RNA
<213> ORGANISM: artificial
<220> FEATURE:
<223> OTHER INFORMATION: mRNA sequence of ppLuc(GC)-ag-A64-PolioCL

<400> SEQUENCE: 50

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgcc gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu gguguucgug agcaagaagg ccugcagaa     420 gauccugaac gugcagaaga gcugcccau cauccagaag aucaucauca uggacagcaa    480
gaccgacuac cagggcuucc agucgaugua cacguucgug accagccacc ucccgccggg    540
cuucaacgag uacgacuucg uccggagag cuucgaccgg acaagacca ucgcccugau     600 caugaacagc agcggcagca ccggccugcc gaaggggug gccugccgc accgaccgc      660 cugcgugcgc uucucgcacg cccgggaccc caucuucggc aaccagauca ucccggacac    720
cgccauccug agcguggugc cguuccacca cggcuucggc auguuuacga cccugggcua    780
ccucaucugc ggcuuccggg uggccugau guaccgguuc gaggaggagc uguuccugcg    840
gagccugcag gacuacaaga uccagagcgc gcucucgug ccgacccgu ucagcuucuu     900 cgccaagagc acccugaucg acaaguacga ccugucgaac cugcacgaga ugccagcgg    960 gggcgccccg cugagcaagg aggugggcga ggccguggcc aagcgguucc accucccggg    1020
cauccgccag ggcuacggcc ugaccgagac cacgagcgcg auccgaucca ccccgaggg    1080 ggacgacaag ccgggcgccg ugggcaaggu ggucccguuc uucgaggcca aggugguga    1140 ccuggacacc ggcaagaccc ugggcgugaa ccagcggggc gagcugugcg ugcggggcc    1200 gaugaucaug agcggcuacg ugaacaaccc ggaggccacc aacgcccuca ucgacaagga   1260
cggcuggcug cacagcggcg acaucgccua cuggacgag gacgagcacu ucuucaucgu    1320
```

```
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggucuuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggcccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca ucaauucuaa aacagcucug ggguuguacc cacccccagag gcccacgugg   1860 cggcuaguac uccgguauug cgguacccuu guacgccugu uuuagaauu                1909

<210> SEQ ID NO 51
<211> LENGTH: 1841
<212> TYPE: RNA
<213> ORGANISM: artificial
<220> FEATURE:
<223> OTHER INFORMATION: mRNA sequence of ppLuc(GC)-ag-A64-G30

<400> SEQUENCE: 51
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240 ccaccgggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu gguguucgug agcaagaagg gccugcagaa    420
gauccugaac gugcagaaga gcugcccau cauccagaag aucaucauca uggacagcaa    480
gaccgacuac caggggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccugcc gaaggggggu gccucugccgc accggaccgc    660 cugcgugcgc uucucgcacg cccgggaccc caucuucggc aaccgaucag ucccggacac    720
cgccauccug agcguggugc cguuccacca cggcuucggc auguucacga cccugggcua    780
ccucaucugc ggcuucccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca ccccccgaggg   1080 ggacgacaag ccgggcgccg ugggcaaggu ggucccguuc uucgaggcca ggugguggga   1140
ccuggacacc ggcaagaccc ugggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
```

| | |
|---|---:|
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggucuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uggggggggg gggggggggg gggggggggg g | 1841 |

<210> SEQ ID NO 52
<211> LENGTH: 1841
<212> TYPE: RNA
<213> ORGANISM: artificial
<220> FEATURE:
<223> OTHER INFORMATION: mRNA sequence of ppLuc(GC)-ag-A64-U30

<400> SEQUENCE: 52

| | |
|---|---:|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggucuucgug agcaagaagg ccugcagaa | 420 |
| gauccugaac gugcagaaga gcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagaacca ucgcccugau | 600 |
| caugaacagc agcggcagca ccggccugcc gaaggggggug gcccugccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguuacgac cccugggcua | 780 |
| ccucaucugc ggcuuccggg ugguccugau guaccgguuc gaggaggagc uguuccugcg | 840 |
| gagccugcag gacuacaaga uccagagcgc gcucucgug ccgacccgu ucagcuucuu | 900 |
| cgccaagagc acccugaucg acaaguacga ccugucgaac cugcacgaga ucgccagcgg | 960 |
| gggcgccccg cugagcaagg agguggggcga ggccgguggcc aagcgguucc accuccggg | 1020 |
| cauccgcccag ggcuacggcc ugaccgagac cacgagcgcg auccugauca cccccgaggg | 1080 |
| ggacgacaag ccgggcgccg uggggcaaggu ggucccguuc uucgaggcca agguggugga | 1140 |
| ccuggacacc ggcaagaccc ugggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggucuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |

| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uuuuuuuuuu uuuuuuuuuu uuuuuuuuuu u | 1841 |

<210> SEQ ID NO 53
<211> LENGTH: 1857
<212> TYPE: RNA
<213> ORGANISM: artificial
<220> FEATURE:
<223> OTHER INFORMATION: mRNA sequence of ppLuc(GC)-ag-A64-SL

<400> SEQUENCE: 53

| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacgccc ugaacaccaa | 240 |
| ccaccggauc gugguguccu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggugguucgug agcaagaagg ccugcagaa | 420 |
| gauccugaac gugcagaaga gcugcccau cauccgaaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagacca ucgcccugau | 600 |
| caugaacagc agcggcagca ccggccugcc gaaggggggug gccugccgc accggaccgc | 660 |
| cugcgugcgc uucucgcacg cccgggaccc caucuucgc aaccagauca ucccggacac | 720 |
| cgccauccug agcguggugc cguuccacca cggcuucggc auguucacga cccugggcua | 780 |
| ccucaucugc ggcuuccggg uggccucgau guaccggguuc gaggaggagc uguuccugcg | 840 |
| gagccugcag gacuacaaga uccagagcgc gcugcucgug ccgacccugu cagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |
| cauccgccag ggcuacgcc ugaccgagac cacgagcgcg auccugauca ccccccgaggg | 1080 |
| ggacgacaag ccgggcgccg ugggcaaggu ggucccguuc uucgaggcca aggugggga | 1140 |
| ccuggacacc ggcaagaccc uggcgugaa ccagcggggc gagcugugcg ugcggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcuggaa | 1380 |
| gagcauccug cuccagcacc ccaacaucuu cgacgccggc guggccgggc ugccggacga | 1440 |
| cgacgccggc gagcugccgg ccgcggugu ggugcuggag cacggcaaga ccaugacgga | 1500 |
| gaaggagauc gucgacuacg uggccagcca ggugaccacc gccaagaagc ugcggggcgg | 1560 |
| cguggguuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uuauggcggc cguguccacc acggauauca ccgguggga cgcggcc | 1857 |

<210> SEQ ID NO 54
<211> LENGTH: 1838
<212> TYPE: RNA
<213> ORGANISM: artificial
<220> FEATURE:
<223> OTHER INFORMATION: ppLuc(GC)-ag-A64-N32

<400> SEQUENCE: 54

| | | |
|---|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggguuucgug agcaagaagg gccugcagaa | 420 |
| gauccugaac gugcagaaga gcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagaccaa ucgcccugau | 600 |
| caugaacagc agcggcagca ccggccugcc gaaggggggug gcccugccgc accggaccgc | 660 |
| cugcgugcgc uucucgcacg cccgggaccc caucuucggc aaccagauca ucccggacac | 720 |
| cgccauccug agcguggugc cguuccacca cggcuucggc auguuacga cccugggcua | 780 |
| ccucaucugc ggcuuccggg uggucccugau guaccgguuc gaggaggagc uguuccugcg | 840 |
| gagccugcag gacuacaaga uccagagcgc gcugcucgug ccgacccugu ucagcuucuu | 900 |
| cgccaagagc acccugaucg acaaguacga ccugucgaac cugcacgaga ucgccagcgg | 960 |
| gggcgccccg cugagcaagg aggugggcga ggccgguggcc aagcgguucc accucccggg | 1020 |
| cauccgccag ggcuacgggcc ugaccagac cacgagcgcg auccugauca ccccccgaggg | 1080 |
| ggacgacaag ccgggcgccg ugggcaaggu ggucccguuc uucgaggcca aggugguggaa | 1140 |
| ccuggacacc ggcaagaccc uggggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cuggggacgag gacgagcacu ucuuacaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcgggggcgg | 1560 |
| cguggguguuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgaugggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca ucccccucua gacaauugga auuccaua | 1838 |

<210> SEQ ID NO 55
<211> LENGTH: 945
<212> TYPE: RNA
<213> ORGANISM: artificial
<220> FEATURE:
<223> OTHER INFORMATION: mRNA sequence of MmMOG(wt)-ag-A64-C30

<400> SEQUENCE: 55

```
gggagaaagc uuaccauggc cuguuugugg agcuucucuu ggcccagcug cuuccucucc    60
cuucuccucc uucuccucca guugucaugc agcuaugcag gacaauucag agugauagga   120
ccagggauauc ccauccgggc uuuaguuggg gaugaagcag agcugccgug ccgcaucucu  180
ccugggaaaa augccacggg cauggaggug gguugguacc guucucccuu cucaagagug   240
guucaccucu accgaaaugg caaggaccaa gaugcagagc aagcaccuga auaccgggga   300
cgcacagagc uucugaaaga gacuaucagu gagggaaagg uuacccuuag gauucagaac   360
gugagauucu cagaugaagg aggcuacacc ugcuucuuca gagaccacuc uuaccaagaa   420
gaggcagcaa uggaguugaa agugagaagau cccuucuauu gggucaaccc cggugugcug  480
acucucaucg cacuugugcc uacgauccuc cugcaggucc cuguaggccu uguauuccuc   540
uuccugcagc acagacugag aggaaaacuu cgugcagaag uagagaaucu ccaucggacu   600
uuugauccuc acuuccugag ggugcccugc uggaagauaa cacuguuugu auugugccu    660
guucuuggac cccugguugc cuugaucauc ugcuacaacu ggcugcaccg aagacuggca   720
ggacaguuuc uugaagagcu aagaaacccc uuuugaccac uaguuauaag acugacuagc   780
ccgaugggcc ucccaacggg cccuccuccc cuccuugcac cgagauuaau aaaaaaaaaa   840
aaaaaaaaaa aaaaaaaaaa aaaaaaaaaa aaaaaaaaaa aaaaaaaaaa aaaauauucc   900
cccccccccc cccccccccc cccccccccuc uagacaauug gaauu                 945
```

<210> SEQ ID NO 56
<211> LENGTH: 959
<212> TYPE: RNA
<213> ORGANISM: artificial
<220> FEATURE:
<223> OTHER INFORMATION: mRNA sequence of MmMOG(wt)-ag-A64-C30-histoneSL

<400> SEQUENCE: 56

```
gggagaaagc uuaccauggc cuguuugugg agcuucucuu ggcccagcug cuuccucucc    60
cuucuccucc uucuccucca guugucaugc agcuaugcag gacaauucag agugauagga   120
ccagggauauc ccauccgggc uuuaguuggg gaugaagcag agcugccgug ccgcaucucu  180
ccugggaaaa augccacggg cauggaggug gguugguacc guucucccuu cucaagagug   240
guucaccucu accgaaaugg caaggaccaa gaugcagagc aagcaccuga auaccgggga   300
cgcacagagc uucugaaaga gacuaucagu gagggaaagg uuacccuuag gauucagaac   360
gugagauucu cagaugaagg aggcuacacc ugcuucuuca gagaccacuc uuaccaagaa   420
gaggcagcaa uggaguugaa agugagaagau cccuucuauu gggucaaccc cggugugcug  480
acucucaucg cacuugugcc uacgauccuc cugcaggucc cuguaggccu uguauuccuc   540
uuccugcagc acagacugag aggaaaacuu cgugcagaag uagagaaucu ccaucggacu   600
uuugauccuc acuuccugag ggugcccugc uggaagauaa cacuguuugu auugugccu    660
guucuuggac cccugguugc cuugaucauc ugcuacaacu ggcugcaccg aagacuggca   720
ggacaguuuc uugaagagcu aagaaacccc uuuugaccac uaguuauaag acugacuagc   780
ccgaugggcc ucccaacggg cccuccuccc cuccuugcac cgagauuaau aaaaaaaaaa   840
aaaaaaaaaa aaaaaaaaaa aaaaaaaaaa aaaaaaaaaa aaaaaaaaaa aaaaugcauc   900
cccccccccc cccccccccc cccccccccc aaaggcucuu uucagagcca ccaggaauu   959
```

NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED ALLERGENIC ANTIGEN OR AN AUTOIMMUNE SELF-ANTIGEN

The present invention relates to a nucleic acid sequence, comprising or coding for a coding region, encoding at least one peptide or protein comprising an allergenic antigen or an autoimmune self-antigen or a fragment, variant or derivative thereof, at least one histone stem-loop and a poly(A) sequence or a polyadenylation signal. Furthermore, the present invention provides the use of the nucleic acid for increasing the expression of said encoded peptide or protein. It also discloses its use for the preparation of a pharmaceutical composition, especially a vaccine, e.g. for use in the treatment of allergies or autoimmune diseases. The present invention further describes a method for increasing the expression of a peptide or protein comprising an allergenic antigen or an autoimmune self-antigen or a fragment, variant or derivative thereof, using the nucleic acid comprising or coding for a histone stem-loop and a poly(A) sequence or a polyadenylation signal.

An allergy is a hypersensitivity disorder of the immune system. Allergic reactions occur when a person's immune system reacts to normally harmless substances in the environment. A substance that causes a reaction is called an allergen or an allergenic antigen. Allergy is one of four forms of hypersensitivity and is formally called type I (or immediate) hypersensitivity. Allergic reactions are distinctive because of excessive activation of certain white blood cells called mast cells and basophils by Immunoglobulin E (IgE). This reaction results in an inflammatory response which can range from uncomfortable to dangerous. Mild allergies like hay fever are very common in the human population and cause symptoms such as red eyes, itchiness, and runny nose, eczema, hives, hay fever, or an asthma attack. Allergies can play a major role in conditions such as asthma. In some people, severe allergies to environmental or dietary allergens or to medication may result in life-threatening reactions called anaphylaxis. Food allergies and reactions to the venom of stinging insects such as wasps and bees are often associated with these severe reactions. Treatments for allergies include avoiding known allergens, use of medications such as anti-histamines that specifically prevent allergic reactions, steroids that modify the immune system in general, and medications such as decongestants that reduce the symptoms. Newer approaches use immunotherapy to desensitize the body's immune response.

Desensitization or hyposensitization is a treatment in which the patient is gradually vaccinated with progressively larger doses of the allergen in question. This can either reduce the severity or eliminate hypersensitivity altogether. It relies on the progressive skewing of IgG antibody production, to block excessive IgE production seen in atopys. In a sense, the person builds up immunity to increasing amounts of the allergen in question. Studies have demonstrated the long-term efficacy and the preventive effect of immunotherapy in reducing the development of new allergy.

But desensitization with protein allergens is associated with several problems, like e.g. crosslinking of pre-existing immunoglobulin E on mast cells/basophils or induction of de novo synthesis of immunoglobulin E by the protein immunization itself. Genetic immunization offers innovative solutions to these major problems associated with protein immunization. It easily enables the routine production of hypoallergenic vaccines, which do not translate native allergens, thus avoiding potential anaphylactic side effects. Genetic vaccines can also be applied as mixtures of single vaccines, making them interesting candidates for treatment based on component-resolved diagnosis, followed by an individualized therapy with the relevant allergens.

Autoimmune diseases typically arise from an overactive immune response of the body against self-antigens (autoantigens), which are present and produced in the body, i.e., the body attacks its own cells, proteins, or other components of the body. Autoimmune diseases as known today can be classified as hypersensibility reactions according to known subtypes II, III or IV. Hypersensibility reactions of subtype I comprise allergies and asthma. These reactions are directed against exogenous antigens and are therefore not regarded as autoimmune reactions.

In summary, autoimmunity may be recognized as the failure of an organism to discriminate between its own constituent parts (down to the sub-molecular levels) as self-antigens and (exogenous) non-self-antigens, which typically induce an immune response in the body. Furthermore, the components of the immune systems do not appear to be capable to entirely delete the specific self-antigen or fragments thereof, thus resulting in (chronic) inflammatory autoimmune diseases.

Treatment of autoimmune diseases today is mainly restricted to alleviation of the symptoms rather than abolishment of the causes of autoimmune diseases. Present approaches include, e.g., suppression of the body's immune response in order to alleviate the (inflammatory) attack on the own tissue and damage of tissue due to (inflammatory) attacks. Medicaments suitable for such a treatment are typically selected from immunosuppressive medicaments. However, an overall suppression of immune system may lead to severe problems: When abolishing or diminishing the negative activities of the immune system the necessary protective activity of the body's immune system is typically impaired. If an immunosuppressive medicament is capable to efficiently protect attacked organs, the whole organism's capability to combat infections is impaired. Up to now, there are only single attempts, which try to circumvent these general problems.

Therefore, supplementary strategies have been investigated in recent years in addition to such "conventional treatments" to avoid or at least reduce the impact on the immune system by such treatments. One such supplementary treatment in particular includes gene therapeutic approaches or genetic vaccination, which already have been found to be highly promising for treatment or for supporting such conventional therapies.

Gene therapy and genetic vaccination are methods of molecular medicine which already have been proven in the therapy and prevention of diseases and generally exhibit a considerable effect on daily medical practice, in particular on the treatment of diseases as mentioned above. Both methods, gene therapy and genetic vaccination, are based on the introduction of nucleic acids into the patient's cells or tissue and subsequent processing of the information coded for by the nucleic acid that has been introduced into the cells or tissue, that is to say the (protein) expression of the desired polypeptides.

In gene therapy approaches, typically DNA is used even though RNA is also known in recent developments. Importantly, in all these gene therapy approaches mRNA functions as messenger for the sequence information of the encoded protein, irrespectively if DNA, viral RNA or mRNA is used.

In general RNA is considered an unstable molecule: RNases are ubiquitous and notoriously difficult to inactivate. Furthermore, RNA is also chemically more labile than DNA. Thus, it is perhaps surprising that the "default state" of an mRNA in a eukaryotic cell is characterized by a relative stability and specific signals are required to accelerate the decay of individual mRNAs. The main reason for this finding appears to be that mRNA decay within cells is catalyzed almost exclusively by exonucleases. However, the ends of eukaryotic mRNAs are protected against these enzymes by specific terminal structures and their associated proteins: a m7GpppN CAP at the 5' end and typically a poly(A) sequence at the 3' end. Removal of these two terminal modifications is thus considered rate limiting for mRNA decay. Although a stabilizing element has been characterized in the 3' UTR of the alpha-globin mRNA, RNA sequences affecting turnover of eukaryotic mRNAs typically act as a promoter of decay usually by accelerating deadenylation (reviewed in Meyer, S., C. Temme, et al. (2004), Crit Rev Biochem Mol Biol 39(4): 197-216).

As mentioned above, the 5' ends of eukaryotic mRNAs are typically modified posttranscriptionally to carry a methylated CAP structure, e.g. m7GpppN. Aside from roles in RNA splicing, stabilization, and transport, the CAP structure significantly enhances the recruitment of the 40S ribosomal subunit to the 5' end of the mRNA during translation initiation. The latter function requires recognition of the CAP structure by the eukaryotic initiation factor complex eIF4F. The poly(A) sequence additionally stimulates translation via increased 40S subunit recruitment to mRNAs, an effect that requires the intervention of poly(A) binding protein (PABP). PABP, in turn, was recently demonstrated to interact physically with eIF4G, which is part of the CAP-bound eIF4F complex. Thus, a closed loop model of translation initiation on capped, polyadenylated mRNAs was postulated (Michel, Y. M., D. Poncet, et al. (2000), J Biol Chem 275(41): 32268-76).

Nearly all eukaryotic mRNAs end with such a poly(A) sequence that is added to their 3' end by the ubiquitous cleavage/polyadenylation machinery. The presence of a poly (A) sequence at the 3' end is one of the most recognizable features of eukaryotic mRNAs. After cleavage, most pre-mRNAs, with the exception of replication-dependent histone transcripts, acquire a polyadenylated tail. In this context, 3' end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and depends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90).

The only known exception to this rule are the replication-dependent histone mRNAs which end with a histone stem-loop instead of a poly(A) sequence. Exemplary histone stem-loop sequences are described in Lopez et al. (Dávila López, M., & Samuelsson, T. (2008), RNA (New York, N.Y.), 14(1), 1-10. doi:10.1261/rna.782308).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the L17 snRNP through base pairing of the U7 snRNA with the HDE. The 3'-UTR sequence comprising the histone stem-loop structure and the histone downstream element (HDE) (binding site of the U7 snRNP) were usually termed as histone 3'-processing signal (see e.g. Chodchoy, N., N. B. Pandey, et al. (1991). Mol Cell Biol 11(1): 497-509).

Due to the requirement to package newly synthesized DNA into chromatin, histone synthesis is regulated in concert with the cell cycle. Increased synthesis of histone proteins during S phase is achieved by transcriptional activation of histone genes as well as posttranscriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell-cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), *Molecular and Cellular Biology*, 14(3), 1709-1720 and Williams, A. S., & Marzluff, W. F., (1995), *Nucleic Acids Research*, 23(4), 654-662).

Even though histone genes are generally classified as either "replication-dependent", giving rise to mRNA ending in a histone stem-loop, or "replacement-type", giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during *Xenopus oogenesis* using Luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha Globin, taking advantage of the fact that the globin gene contains introns as opposed to the intron-less histone genes. For this purpose constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070; Pandey, N. B., & Marzluff, W. F. (1987). Molecular and Cellular Biology, 7(12), 4557-4559; Pandey, N. B., et al. (1990). Nucleic Acids Research, 18(11), 3161-3170).

In another approach Lüscher et al. investigated the cell-cycle dependent regulation of a recombinant histone H4 gene. Constructs were generated in which the H4 coding sequence was followed by a histone stem-loop signal and a polyadenylation signal, the two processing signals incidentally separated by a galactokinase coding sequence (Lüscher, B. et al, (1985). Proc. Natl. Acad. Sci. USA, 82(13), 4389-4393).

Additionally, Stauber et al. identified the minimal sequence required to confer cell-cycle regulation on histone H4 mRNA levels. For these investigations constructs were used, comprising a coding sequence for the selection marker Xanthine:guanine phosphoribosyl transferase (GPT) preceding a histone stem-loop signal followed by a polyadenylation signal (Stauber, C. et al., (1986). EMBO J, 5(12), 3297-3303).

Examining histone pre-mRNA processing Wagner et al. identified factors required for cleavage of histone pre-mRNAs using a reporter construct placing EGFP between a histone stem-loop signal and a polyadenylation signal, such that EGFP was expressed only in case histone pre-mRNA processing was disrupted (Wagner, E. J. et al., (2007). Mol Cell 28(4), 692-9).

To be noted, translation of polyadenylated mRNA usually requires the 3' poly(A) sequence to be brought into proximity of the 5' CAP. This is mediated through protein-protein interaction between the poly(A) binding protein and eukaryotic initiation factor eIF4G. With respect to replication-dependent histone mRNAs, an analogous mechanism has been uncovered. In this context, Gallie et al. show that the histone stem-loop is functionally similar to a poly(A) sequence in that it enhances translational efficiency and is co-dependent on a 5'-CAP in order to establish an efficient level of translation. They showed that the histone stem-loop is sufficient and necessary to increase the translation of a reporter mRNA in transfected Chinese hamster ovary cells but must be positioned at the 3'-terminus in order to function optimally. Therefore, similar to the poly(A) tail on other mRNAs, the 3' end of these histone mRNAs appears to be essential for translation in vivo and is functionally analogous to a poly(A) tail (Gallie, D. R., Lewis, N. J., & Marzluff, W. F. (1996), Nucleic Acids Research, 24(10), 1954-1962).

Additionally, it could be shown that SLBP is bound to the cytoplasmic histone mRNA and is required for its translation. Even though SLBP does not interact directly with eIF4G, the domain required for translation of histone mRNA interacts with the recently identified protein SLIP1. In a further step, SLIP1 interacts with eIF4G and allows to circularize histone mRNA and to support efficient translation of histone mRNA by a mechanism similar to the translation of polyadenylated mRNAs.

As mentioned above, gene therapy approaches normally use DNA to transfer the coding information into the cell which is then transcribed into mRNA, carrying the naturally occurring elements of an mRNA, particularly the 5'-CAP structure and the 3' poly(A) sequence to ensure expression of the encoded therapeutic or antigenic protein.

However, in many cases expression systems based on the introduction of such nucleic acids into the patient's cells or tissue and the subsequent expression of the desired polypeptides coded for by these nucleic acids do not exhibit the desired, or even the required, level of expression which may allow for an efficient therapy, irrespective as to whether DNA or RNA is used.

In the prior art, different attempts have hitherto been made to increase the yield of the expression of an encoded protein, in particular by use of improved expression systems, both in vitro and/or in vivo. Methods for increasing expression described generally in the prior art are conventionally based on the use of expression vectors or cassettes containing specific promoters and corresponding regulation elements. As these expression vectors or cassettes are typically limited to particular cell systems, these expression systems have to be adapted for use in different cell systems. Such adapted expression vectors or cassettes are then usually transfected into the cells and typically treated in dependence of the specific cell line. Therefore, preference is given primarily to those nucleic acid molecules which are able to express the encoded proteins in a target cell by systems inherent in the cell, independent of promoters and regulation elements which are specific for particular cell types. In this context, there can be distinguished between mRNA stabilizing elements and elements which increase translation efficiency of the mRNA.

mRNAs which are optimized in their coding sequence and which are in general suitable for such a purpose are described in application WO 02/098443 (CureVac GmbH). For example, WO 02/098443 describes mRNAs that are stabilised in general form and optimised for translation in their coding regions. WO 02/098443 further discloses a method for determining sequence modifications. WO 02/098443 additionally describes possibilities for substituting adenine and uracil nucleotides in mRNA sequences in order to increase the guanine/cytosine (G/C) content of the sequences. According to WO 02/098443, such substitutions and adaptations for increasing the G/C content can be used for gene therapeutic applications but also genetic vaccines in the treatment of cancer or infectious diseases. In this context, WO 02/098443 generally mentions sequences as a base sequence for such modifications, in which the modified mRNA codes for at least one biologically active peptide or polypeptide, which is translated in the patient to be treated, for example, either not at all or inadequately or with faults. Alternatively, WO 02/098443 proposes mRNAs coding for antigens e.g. allergenic antigens or auto-immune self-antigens or viral antigens as a base sequence for such modifications.

In a further approach to increase the expression of an encoded protein the application WO 2007/036366 describes the positive effect of long poly(A) sequences (particularly longer than 120 bp) and the combination of at least two 3' untranslated regions of the beta globin gene on mRNA stability and translational activity.

However, even though all these latter prior art documents already try to provide quite efficient tools for gene therapy approaches and additionally improved mRNA stability and translational activity, there still remains the problem of a generally lower stability of RNA-based applications versus DNA vaccines and DNA based gene therapeutic approaches. Accordingly, there still exists a need in the art to provide improved tools for gene therapy approaches and genetic vaccination or as a supplementary therapy for conventional treatments as discussed above, which allow for better provision of encoded proteins in vivo, e.g. via a further improved mRNA stability and/or translational activity, preferably for gene therapy and genetic vaccination.

Furthermore despite of all progress in the art, efficient expression of an encoded peptide or protein in cell-free systems, cells or organisms (recombinant expression) is still a challenging problem.

The object underlying the present invention is, therefore, to provide additional and/or alternative methods to increase expression of an encoded protein, preferably via further stabilization of the mRNA and/or an increase of the translational efficiency of such an mRNA with respect to such nucleic acids known from the prior art for the use in genetic vaccination in the therapeutic or prophylactic treatment of allergies or autoimmune diseases.

This object is solved by the subject matter of the attached claims. Particularly, the object underlying the present invention is solved according to a first aspect by an inventive nucleic acid sequence comprising or coding for a) a coding region, encoding at least one peptide or protein which comprises an allergenic antigen or an autoimmune self-antigen or a fragment, variant or derivative thereof;
b) at least one histone stem-loop, and
c) a poly(A) sequence or a polyadenylation signal, preferably for increasing the expression of said encoded peptide or protein.

Alternatively, any appropriate stem loop sequence other than a histone stem loop sequence (derived from histone genes, in particular from histone genes of the families H1, H2A, H2B, H3 and H4) may be employed by the present invention in all of its aspects and embodiments.

In this context it is particularly preferred that the inventive nucleic acid according to the first aspect of the present invention is produced at least partially by DNA or RNA synthesis, preferably as described herein or is an isolated nucleic acid.

The present invention is based on the surprising finding of the present inventors, that the combination of a poly(A) sequence or polyadenylation signal and at least one histone stem-loop, even though both representing alternative mechanisms in nature, acts synergistically as this combination increases the protein expression manifold above the level observed with either of the individual elements. The synergistic effect of the combination of poly(A) and at least one histone stem-loop is seen irrespective of the order of poly(A) and histone stem-loop and irrespective of the length of the poly(A) sequence.

Therefore it is particularly preferred that the inventive nucleic acid sequence comprises or codes for a) a coding region, encoding at least one peptide or protein which comprises an allergenic antigen or an autoimmune self-antigen or a fragment, variant or derivative thereof; b) at least one histone stem-loop, and c) a poly(A) sequence or polyadenylation sequence; preferably for increasing the expression level of said encoded peptide or protein. In some preferred embodiments, it may be preferred if the encoded protein is not a histone protein, in particular no histone protein of the H4, H3, H2A and/or H2B histone family or a fragment, derivative or variant thereof retaining histone(-like) function), namely forming a nucleosome. Also, the encoded protein typically does not correspond to a histone linker protein of the H1 histone family. The inventive nucleic acid molecule does typically not contain any regulatory signals (5' and/or, particularly, 3') of a mouse histone gene, in particular not of a mouse histone gene H2A and, further, most preferably not of the mouse histone gene H2A614. In particular, it does not contain a histone stem loop and/or a histone stem loop processing signal from a mouse histone gene, in particular not of mouse histone gene H2A und, most preferably not of mouse histone gene H2A614.

Also, the inventive nucleic acid typically does not provide a reporter protein (e.g. Luciferase, GFP, EGFP, β-Galactosidase, particularly EGFP), galactokinase (galK) and/or marker or selection protein (e.g. alpha-Globin, Galactokinase and Xanthine:Guanine phosphoribosyl transferase (GPT)) or a bacterial reporter protein, e.g. chloramphenicol acetyl transferase (CAT) or other bacterial antibiotics resistance proteins, e.g. derived from the bacterial neo gene in its element (a).

A reporter, marker or selection protein is typically understood not to be a protein acting as an allergic antigen or autoimmune self-antigen according to the invention. A reporter, marker or selection protein or its underlying gene is commonly used as a research tool in bacteria, cell culture, animals or plants. They confer on organisms (preferably heterologously) expressing them an easily identifiable property, which may be measured or which allows for selection. Specifically, marker or selection proteins exhibit a selectable function. Typically, such selection, marker or reporter proteins do not naturally occur in humans or other mammals, but are derived from other organisms, in particular from bacteria or plants. Accordingly, proteins with selection, marker or reporter function originating from species other than mammals, in particular other than humans, are preferably excluded from being understood as "an allergic antigen or autoimmune self-antigen" according to the present invention. In particular, a selection, marker or reporter protein allows to identify transformed cells by in vitro assays based e.g. on fluorescence or other spectroscopic techniques and resistance towards antibiotics. Selection, reporter or marker genes awarding such properties to transformed cells are therefore typically not understood to be an allergic antigen or autoimmune self-antigen according to the invention.

In any case, reporter, marker or selection proteins do usually not exert any therapeutic effect by acting as an allergic antigen or autoimmune self-antigen. If any single reporter, marker or selection protein should nevertheless do so (in addition to its reporter, selection or marker function), such a reporter, marker or selection protein is preferably not understood to be a "an allergic antigen or autoimmune self-antigen" within the meaning of the present invention.

In contrast, an allergic antigen or autoimmune self-antigen (including its fragments, variants and derivatives), in particular excluding histone genes of the families H1, H2A, H2B, H3 and H4, according to the present invention does typically not exhibit a selection, marker or reporter function. If any single "an allergic antigen or autoimmune self-antigen" nevertheless should do so (in addition to its therapeutic, allergic function), such a protein is preferably not understood to be a "selection, marker or reporter protein" within the meaning of the present invention.

It is most preferably understood that a an autoimmune self-antigen according to the invention is derived from mammals, in particular humans, and does not qualify as selection, marker or reporter protein, while an allergic antigen is typically derived from plants or lower organisms, dogs, cats and does also not qualify as selection, marker or reporter protein.

Accordingly, it is preferred that the coding region (a) encoding at least one peptide or protein is heterologous to at least (b) the at least one histone stem loop, or more broadly, to any appropriate stem loop. In other words, "heterologous" in the context of the present invention means that the at least one stem loop sequence does not naturally occur as a (regulatory) sequence (e.g. at the 3'UTR) of the specific gene, which encodes the (allergic or autoimmune self-antigen) protein or peptide of element (a) of the inventive nucleic acid. Accordingly, the (histone) stem loop of the inventive nucleic acid is derived preferably from the 3' UTR of a gene other than the one comprising the coding region of element (a) of the inventive nucleic acid. E.g., the coding region of element (a) will not encode a histone protein or a fragment, variant or derivative thereof (retaining the function of a histone protein), if the inventive nucleic is heterologous, but will encode any other peptide or sequence (of the same or another species) which exerts a biological function, preferably therapeutic function (as a vaccine against these allergens and autoimmune self-antigens) other than a histone(-like) function, e.g. will encode an therapeutic protein (by exerting a therapeutic function, e.g. in terms vaccination of e.g. mammalian, in particular human, against allergic reactions triggered by exogenous allergens, e.g. plant allergens (e.g. birch etc.) or by autoimmune self-antigens.

In this context it is particularly preferred that the inventive nucleic acid comprises or codes for in 5'- to 3'-direction:
  a) a coding region, encoding at least one peptide or protein which comprises an allergenic antigen or an autoimmune self-antigen or a fragment, variant or derivative thereof;
  b) at least one histone stem-loop, optionally without a histone downstream element (HDE) 3' to the histone stem-loop
  c) a poly(A) sequence or a polyadenylation signal.

The term "histone downstream element (HDE) refers to a purine-rich polynucleotide stretch of about 15 to 20 nucleotides 3' of naturally occurring histone stem-loops, which represents the binding site for the U7 snRNA involved in processing of histone pre-mRNA into mature histone mRNA. For example in sea urchins the HDE is CAAGAAAGA (Dominski, Z. and W. F. Marzluff (2007), Gene 396(2): 373-90).

Furthermore it is preferable that the inventive nucleic acid according to the first aspect of the present invention does not comprise an intron.

In another particular preferred embodiment, the inventive nucleic acid sequence according to the first aspect of the present invention comprises or codes for from 5' to 3':
  a) a coding region, preferably encoding at least one peptide or protein which comprises an allergenic antigen or an autoimmune self-antigen or a fragment, variant or derivative thereof;
  c) a poly(A) sequence; and
  b) at least one histone stem-loop.

The inventive nucleic acid sequence according to the first embodiment of the present invention comprise any suitable nucleic acid, selected e.g. from any (single-stranded or double-stranded) DNA, preferably, without being limited thereto, e.g. genomic DNA, plasmid DNA, single-stranded DNA molecules, double-stranded DNA molecules, or may be selected e.g. from any PNA (peptide nucleic acid) or may be selected e.g. from any (single-stranded or double-stranded) RNA, preferably a messenger RNA (mRNA); etc. The inventive nucleic acid sequence may also comprise a viral RNA (vRNA). However, the inventive nucleic acid sequence may not be a viral RNA or may not contain a viral RNA. More specifically, the inventive nucleic acid sequence may not contain viral sequence elements, e.g. viral enhancers or viral promoters (e.g. no inactivated viral promoter or sequence elements, more specifically not inactivated by replacement strategies), or other viral sequence elements, or viral or retroviral nucleic acid sequences. More specifically, the inventive nucleic acid sequence may not be a retroviral or viral vector or a modified retroviral or viral vector.

In any case, the inventive nucleic acid sequence may or may not contain an enhancer and/or promoter sequence, which may be modified or not or which may be activated or not. The enhancer and or promoter may be plant expressible or not expressible, and/or in eukaryotes expressible or not expressible and/or in prokaryotes expressible or not expressible. The inventive nucleic acid sequence may contain a sequence encoding a (self-splicing) ribozyme or not.

In specific embodiments the inventive nucleic acid sequence may be or may comprise a self-replicating RNA (replicon).

Preferably, the inventive nucleic acid sequence is a plasmid DNA, or an RNA, particularly an mRNA.

In particular embodiments of the first aspect of the present invention, the inventive nucleic acid is a nucleic acid sequence comprised in a nucleic acid suitable for in vitro transcription, particularly in an appropriate in vitro transcription vector (e.g. a plasmid or a linear nucleic acid sequence comprising specific promoters for in vitro transcription such as T3, T7 or Sp6 promoters).

In further particular preferred embodiments of the first aspect of the present invention, the inventive nucleic acid is comprised in a nucleic acid suitable for transcription and/or translation in an expression system (e.g. in an expression vector or plasmid), particularly a prokaryotic (e.g. bacteria like *E. coli*) or eukaryotic (e.g. mammalian cells like CHO cells, yeast cells or insect cells or whole organisms like plants or animals) expression system.

The term "expression system" means a system (cell culture or whole organisms) which is suitable for production of peptides, proteins or RNA particularly mRNA (recombinant expression).

The inventive nucleic acid sequence according to the first aspect of the present invention comprises or codes for at least one histone stem-loop. In the context of the present invention, such a histone stem-loop is typically derived from histone genes and comprises an intramolecular base pairing of two neighbored entirely or partially reverse complementary sequences, thereby forming a stem-loop. A stem-loop can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem loop elements stem1 and stem2. The stem loop is formed when these two neighbored entirely or partially reverse complementary sequences, e.g. stem loop elements stem1 and stem2, form base-pairs with each other, leading to a double stranded nucleic acid sequence comprising an unpaired loop at its terminal ending formed by the short sequence located between stem loop elements stem1 and stem2 on the consecutive sequence. The unpaired loop thereby typically represents a region of the nucleic acid which is not capable of base pairing with either of these stem loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem loop elements is determined by the length, the number of mismatches or bulges it contains (a small number of mismatches is typically tolerable, especially for a longer double stranded stretch), and the base composition of the paired region. In the context of the present invention, a loop length of 3 to 15 bases is conceivable, while a more preferred optimal loop length is 3-10 bases, more preferably 3 to 8, 3 to 7, 3 to 6 or even more preferably 4 to 5 bases, and most preferably 4 bases. The stem sequence forming the double stranded structure typically has a length of between 5 to 10 bases, more preferably, between 5 to 8 bases In the context of the present invention, a histone stem-loop is typically derived from histone genes (e.g. genes from the histone families H1, H2A, H2B, H3, H4) and comprises an intramolecular base pairing of two neighbored entirely or partially reverse complementary sequences, thereby forming a stem-loop. Typically, a histone 3' UTR stem-loop is an RNA element involved in nucleocytoplasmic transport of the histone mRNAs, and in the regulation of stability and of translation efficiency in the cytoplasm. The mRNAs of metazoan histone genes lack polyadenylation and a poly-A tail, instead 3' end processing occurs at a site between this highly conserved stem-loop and a purine rich region around 20 nucleotides downstream (the histone downstream element, or HDE). The histone stem-loop is bound by a 31 kDa stem-loop binding protein (SLBP—also termed the histone hairpin binding protein, or HBP). Such histone stem-loop structures are preferably employed by the present invention in combination with other sequence elements and structures, which do not occur naturally (which means in untransformed living organisms/cells) in histone genes, but are combined—according to the invention—to provide an artificial, heterologous nucleic acid. Accordingly, the present invention is particularly based on the finding that an artificial (non-native) combination of a histone stem-loop structure with other heterologous sequence elements, which do not occur in histone genes or metazoan histone genes and are isolated from operational and/or regulatory sequence regions (influencing transcription and/or translation) of genes coding for proteins other than histones, provide advantageous effects. Accordingly, one aspect of the invention provides the combination of a histone stem-loop structure with a poly(A) sequence or a sequence representing a polyadenylation signal (3'-terminal of a coding region), which does not occur in metazoan histone genes.

According to another preferred aspect of the invention, a combination of a histone stem-loop structure with a coding region coding for a protein (acting as an allergen or acting as an autoimmune self-antigen), which does, preferably not occur in metazoan histone genes, is provided herewith (coding region and histone stem loop sequence are heterologous). It is preferred, if an autuimmine self-antigen occurs as a protein naturally in mammalians, preferably humans. In a still further preferred embodiment, all the elements (a), (b) and (c) of the inventive nucleic acid are heterologous to each other and are combined artificially from three different sources, e.g. (a) the autoimmune self-antigen coding region from a human gene or the allergen from another source, in particular a non-human organism (e.g. a plant, a pet etc.) (b) the histone stem loop from an untranslated region of a metazoan, e.g. mammalian, non-human or human, histone gene and (c) the poly(A) sequence or the polyadenylation signal from e.g. an untranslated region of a gene other than a histone gene and other than the gene coding for the allergen or the autoimmune self-antigen according to element (a) of such an inventive nucleic acid.

A histone stem loop is, therefore, a stem-loop structure as described herein, which, if preferably functionally defined, exhibits/retains the property of binding to its natural binding partner, the stem-loop binding protein (SLBP—also termed the histone hairpin binding protein, or HBP).

According to the present invention the histone stem loop sequence according to component (b) of claim 1 may not derived from a mouse histone protein. More specifically, the histone stem loop sequence may not be derived from mouse histone gene H2A614. Also, the nucleic acid of the invention may neither contain a mouse histone stem loop sequence nor contain mouse histone gene H2A614. Further, the inventive nucleic acid sequence may not contain a stem-loop processing signal, more specifically, a mouse histone processing signal and, most specifically, may not contain mouse stem loop processing signal H2kA614, even if the inventive nucleic acid sequence may contain at least one mammalian histone gene. However, the at least one mammalian histone gene may not be Seq. ID No. 7 of WO 01/12824.

According to one preferred embodiment of the first inventive aspect, the inventive nucleic acid sequence comprises or codes for at least one histone stem-loop sequence, preferably according to at least one of the following formulae (I) or (II):

Formula (I) (Stem-Loop Sequence without Stem Bordering Elements):

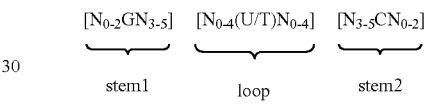

Formula (II) (Stem-Loop Sequence with Stem Bordering Elements):

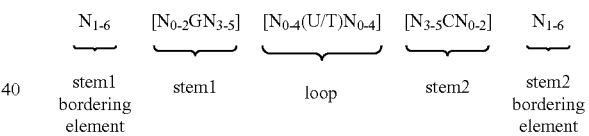

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence [N$_{0-4}$(U/T)N$_{0-4}$] is located between elements stem1 and stem2, and is a consecutive sequence of 3 to 5 nucleotides, more preferably of 4 nucleotides;

wherein each N$_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 [N$_{3-5}$CN$_{0-2}$] is reverse complementary or partially reverse complementary with element stem1, and is a consecutive sequence between of 5 to 7 nucleotides;

wherein N$_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein N$_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleotide guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

In the above context, a wobble base pairing is typically a non-Watson-Crick base pairing between two nucleotides. The four main wobble base pairs in the present context, which may be used, are guanosine-uridine, inosine-uridine, inosine-adenosine, inosine-cytidine (G-U/T, I-U/T, I-A and I-C) and adenosine-cytidine (A-C).

Accordingly, in the context of the present invention, a wobble base is a base, which forms a wobble base pair with a further base as described above. Therefore non-Watson-Crick base pairing, e.g. wobble base pairing, may occur in the stem of the histone stem-loop structure according to the present invention.

In the above context a partially reverse complementary sequence comprises maximally 2, preferably only one mismatch in the stem-structure of the stem-loop sequence formed by base pairing of stem1 and stem2. In other words, stem1 and stem2 are preferably capable of (full) base pairing with each other throughout the entire sequence of stem1 and stem2 (100% of possible correct Watson-Crick or non-Watson-Crick base pairings), thereby forming a reverse complementary sequence, wherein each base has its correct Watson-Crick or non-Watson-Crick base pendant as a complementary binding partner. Alternatively, stem1 and stem2 are preferably capable of partial base pairing with each other throughout the entire sequence of stem1 and stem2, wherein at least about 70%, 75%, 80%, 85%, 90%, or 95% of the 100% possible correct Watson-Crick or non-Watson-Crick base pairings are occupied with the correct Watson-Crick or non-Watson-Crick base pairings and at most about 30%, 25%, 20%, 15%, 10%, or 5% of the remaining bases are unpaired.

According to a preferred embodiment of the first inventive aspect, the at least one histone stem-loop sequence (with stem bordering elements) of the inventive nucleic acid sequence as defined herein comprises a length of about 15 to about 45 nucleotides, preferably a length of about 15 to about 40 nucleotides, preferably a length of about 15 to about 35 nucleotides, preferably a length of about 15 to about 30 nucleotides and even more preferably a length of about 20 to about 30 and most preferably a length of about 24 to about 28 nucleotides.

According to a further preferred embodiment of the first inventive aspect, the at least one histone stem-loop sequence (without stem bordering elements) of the inventive nucleic acid sequence as defined herein comprises a length of about 10 to about 30 nucleotides, preferably a length of about 10 to about 20 nucleotides, preferably a length of about 12 to about 20 nucleotides, preferably a length of about 14 to about 20 nucleotides and even more preferably a length of about 16 to about 17 and most preferably a length of about 16 nucleotides.

According to a further preferred embodiment of the first inventive aspect, the inventive nucleic acid sequence according to the first aspect of the present invention may comprise or code for at least one histone stem-loop sequence according to at least one of the following specific formulae (Ia) or (IIa):

Formula (Ia) (Stem-Loop Sequence without Stem Bordering Elements):

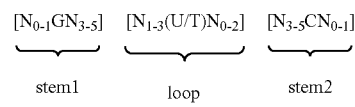

Formula (IIa) (Stem-Loop Sequence with Stem Bordering Elements):

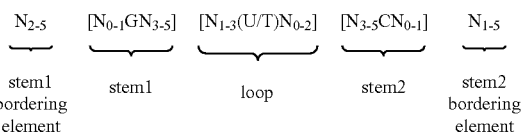

wherein:
N, C, G, T and U are as defined above.

According to a further more particularly preferred embodiment of the first aspect, the inventive nucleic acid sequence may comprise or code for at least one histone stem-loop sequence according to at least one of the following specific formulae (Ib) or (IIb):

Formula (Ib) (Stem-Loop Sequence without Stem Bordering Elements):

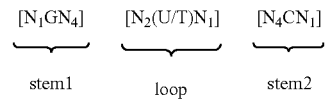

Formula (IIb) (Stem-Loop Sequence with Stem Bordering Elements):

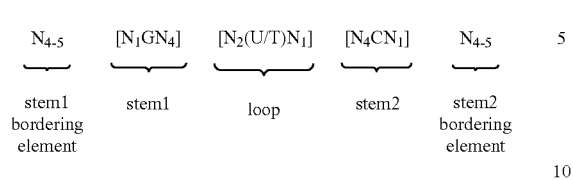

wherein:
N, C, G, T and U are as defined above.

According to an even more preferred embodiment of the first inventive aspect, the inventive nucleic acid sequence according to the first aspect of the present invention may comprise or code for at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1:

Formula (Ic): (Metazoan and Protozoan Histone Stem-Loop Consensus Sequence without Stem Bordering Elements):

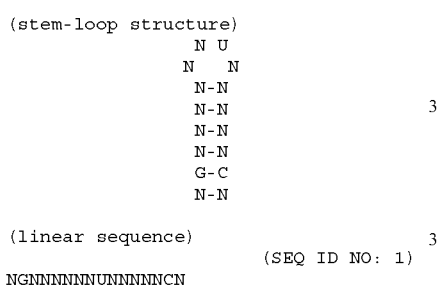

Formula (IIc): (Metazoan and Protozoan Histone Stem-Loop Consensus Sequence with Stem Bordering Elements):

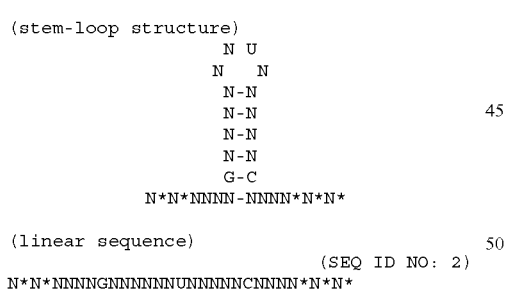

Formula (Id): (without Stem Bordering Elements)

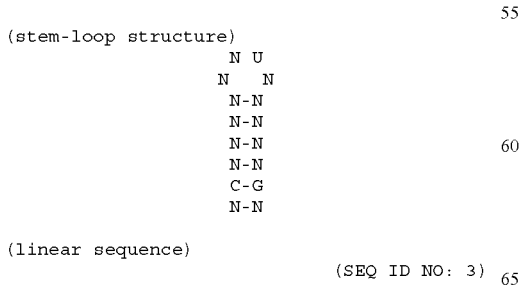

Formula (IId): (with Stem Bordering Elements)

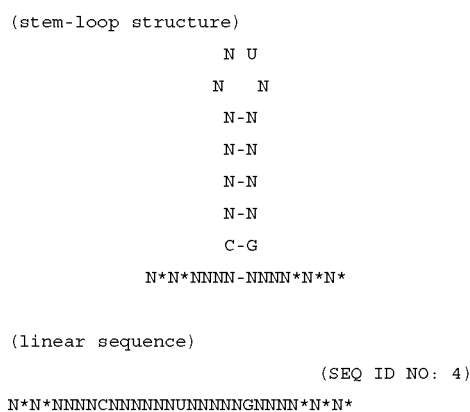

Formula (Ie): (Protozoan Histone Stem-Loop Consensus Sequence without Stem Bordering Elements)

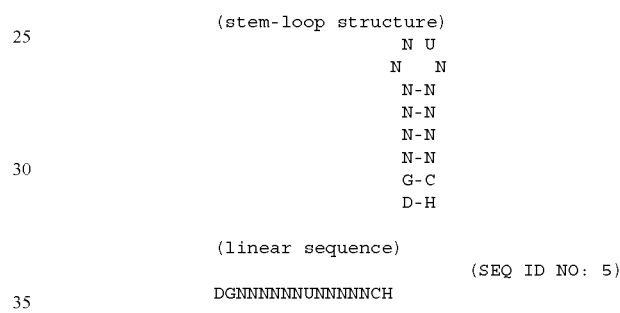

Formula (IIe): (Protozoan Histone Stem-Loop Consensus Sequence with Stem Bordering Elements)

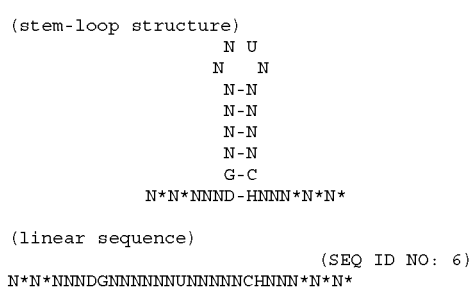

Formula (If): (Metazoan Histone Stem-Loop Consensus Sequence without Stem Bordering Elements)

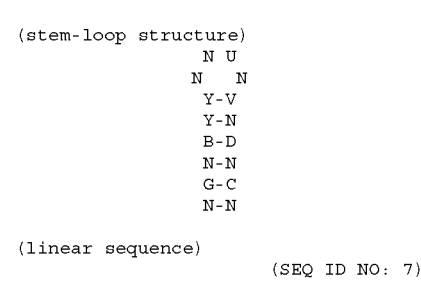

Formula (IIf): (Metazoan Histone Stem-Loop Consensus Sequence with Stem Bordering Elements)

```
(stem-loop structure)
              N U
             N   N
             Y - V
             Y - N
             B - D
             N - N
             G - C
       N*N*NNNN-NNNN*N*N*

(linear sequence)
                         (SEQ ID NO: 8)
       N*N*NNNNGNBYYNNUNVNDNCNNNN*N*N*
```

Formula (Ig): (Vertebrate Histone Stem-Loop Consensus Sequence without Stem Bordering Elements)

```
(stem-loop structure)
              N U
              D H
             Y - A
             Y - B
             Y - R
             H - D
             G - C
             N - N (linear sequence)
                         (SEQ ID NO: 9)
       NGHYYYDNUHABRDCN
```

Formula (IIg): (Vertebrate Histone Stem-Loop Consensus Sequence with Stem Bordering Elements)

```
(stem-loop structure)
              N U
              D H
             Y - A
             Y - B
             Y - R
             H - D
             G - C
       N*N*HNNN-NNNN*N*H*

(linear sequence)
                        (SEQ ID NO: 10)
       N*N*HNNNGHYYYDNUHABRDCNNNN*N*H*
```

Formula (Ih): (Human Histone Stem-Loop Consensus Sequence (*Homo sapiens*) without Stem Bordering Elements)

```
(stem-loop structure)
              Y U
              D H
             U - A
             C - S
             Y - R
             H - R
             G - C
             D - C (linear sequence)
                        (SEQ ID NO: 11)
       DGHYCUDYUHASRRCC
```

Formula (IIh): (Human Histone Stem-Loop Consensus Sequence (*Homo sapiens*) with Stem Bordering Elements)

```
(stem loop structure)
              Y U
              D H
             U - A
             C - S
             Y - R
             H - R
             G - C
       N*H*AAHD-CVHB*N*H*

(linear sequence)
                        (SEQ ID NO: 12)
       N*H*AAHDGHYCUDYUHASRRCCVHB*N*H*
``` wherein in each of above formulae (Ic) to (Ih) or (IIc) to (IIh):
N, C, G, A, T and U are as defined above;
each U may be replaced by T;
each (highly) conserved G or C in the stem elements 1 and 2 may be replaced by its complementary nucleotide base C or G, provided that its complementary nucleotide in the corresponding stem is replaced by its complementary nucleotide in parallel; and/or
G, A, T, U, C, R, Y, M, K, S, W, H, B, V, D, and N are nucleotide bases as defined in the following Table:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context it is particularly preferred that the histone stem-loop sequence according to at least one of the formulae (I) or (Ia) to (Ih) or (II) or (IIa) to (IIh) of the present invention is selected from a naturally occurring histone stem loop sequence, more particularly preferred from protozoan or metazoan histone stem-loop sequences, and even more particularly preferred from vertebrate and mostly preferred from mammalian histone stem-loop sequences especially from human histone stem-loop sequences.

According to a particularly preferred embodiment of the first aspect, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa (FIG. 1), protozoa (FIG. 2), metazoa (FIG. 3), vertebrates (FIG. 4) and humans (FIG. 5) as shown in FIG. 1-5. In this context it is particularly preferred that at least 80%, preferably at least 85%, or most preferably at least 90% of all nucleotides correspond to the most frequently occurring nucleotide of naturally occurring histone stem-loop sequences.

In a further particular embodiment of the first aspect, the histone stem-loop sequence according to at least one of the specific formulae (I) or (Ia) to (Ih) of the present invention is selected from following histone stem-loop sequences (without stem-bordering elements) representing histone stem-loop sequences as generated according to Example 1:

```
(SEQ ID NO: 13 according to formula (Ic))
VGYYYYHHTHRVVRCB (SEQ ID NO: 14 according to formula (Ic))
SGYYYTTYTMARRRCS (SEQ ID NO: 15 according to formula (Ic))
SGYYCTTTTMAGRRCS (SEQ ID NO: 16 according to formula (Ie))
DGNNNBNNTHVNNNCH (SEQ ID NO: 17 according to formula (Ie))
RGNNNYHBTHRDNNCY (SEQ ID NO: 18 according to formula (Ie))
RGNDBYHYTHRDHNCY (SEQ ID NO: 19 according to formula (If))
VGYYYTYHTHRVRRCB (SEQ ID NO: 20 according to formula (If))
SGYYCTTYTMAGRRCS (SEQ ID NO: 21 according to formula (If))
SGYYCTTTTMAGRRCS (SEQ ID NO: 22 according to formula (Ig))
GGYYCTTYTHAGRRCC (SEQ ID NO: 23 according to formula (Ig))
GGCYCTTYTMAGRGCC (SEQ ID NO: 24 according to formula (Ig))
GGCTCTTTTMAGRGCC (SEQ ID NO: 25 according to formula (Ih))
DGHYCTDYTHASRRCC (SEQ ID NO: 26 according to formula (Ih))
GGCYCTTTTHAGRGCC (SEQ ID NO: 27 according to formula (Ih))
GGCYCTTTTMAGRGCC
```

Furthermore in this context following histone stem-loop sequences (with stem bordering elements) as generated according to Example 1 according to one of specific formulae (II) or (IIa) to (IIh) are particularly preferred:

```
(SEQ ID NO: 28 according to formula (IIc))
H*H*HHVVGYYYYHHTHRVVRCBVHH*N*N*

(SEQ ID NO: 29 according to formula (IIc))
M*H*MHMSGYYYTTYTMARRRCSMCH*H*H*

(SEQ ID NO: 30 according to formula (IIc))
M*M*MMMSGYYCTTTTMAGRRCSACH*M*H*

(SEQ ID NO: 31 according to formula (IIe))
N*N*NNNDGNNNBNNTHVNNNCHNHN*N*N*

(SEQ ID NO: 32 according to formula (IIe))
N*N*HHNRGNNNYHBTHRDNNCYDHH*N*N*

(SEQ ID NO: 33 according to formula (IIe))
N*H*HHVRGNDBYHYTHRDHNCYRHH*H*H*

(SEQ ID NO: 34 according to formula (IIf))
H*H*MHMVGYYYTYHTHRVRRCBVMH*H*N*

(SEQ ID NO: 35 according to formula (IIf))
M*M*MMMSGYYCTTYTMAGRRCSMCH*H*H*

(SEQ ID NO: 36 according to formula (IIf))
M*M*MMMSGYYCTTTTMAGRRCSACH*M*H*

(SEQ ID NO: 37 according to formula (IIg))
H*H*MAMGGYYCTTYTHAGRRCCVHN*N*M*

(SEQ ID NO: 38 according to formula (IIg))
H*H*AAMGGCYCTTYTMAGRGCCVCH*H*M*

(SEQ ID NO: 39 according to formula (IIg))
M*M*AAMGGCTCTTTTMAGRGCCMCY*M*M*

(SEQ ID NO: 40 according to formula (IIh))
N*H*AAHDGHYCTDYTHASRRCCVHB*N*H*

(SEQ ID NO: 41 according to formula (IIh))
H*H*AAMGGCYCTTTTHAGRGCCVMY*N*M*

(SEQ ID NO: 42 according to formula (IIh))
H*M*AAAGGCYCTTTTMAGRGCCRMY*H*M*
```

According to a further preferred embodiment of the first inventive aspect, the inventive nucleic acid sequence comprises or codes for at least one histone stem-loop sequence showing at least about 80%, preferably at least about 85%, more preferably at least about 90%, or even more preferably at least about 95%, sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

In a preferred embodiment, the histone stem loop sequence does not contain the loop sequence 5'-UUUC-3'. More specifically, the histone stem loop does not contain the stem1 sequence 5'-GGCUCU-3' and/or the stem2 sequence 5'-AGAGCC-3', respectively. In another preferred embodiment, the stem loop sequence does not contain the loop sequence 5'-CCUGCCC-3' or the loop sequence 5'-UGAAU-3'. More specifically, the stem loop does not contain the stem1 sequence 5'-CCUGAGC-3' or does not contain the stem1 sequence 5'-ACCUUUCUCCA-3' and/or the stem2 sequence 5'-GCUCAGG-3' or 5'-UGGA-GAAAGGU-3', respectively. Also, as far as the invention is not limited to histone stem loop sequences specifically, stem loop sequences are preferably not derived from a mammalian insulin receptor 3'-untranslated region. Also, preferably, the inventive nucleic acid may not contain histone stem loop processing signals, in particular not those derived from mouse histone gene H2A614 gene (H2kA614).

The inventive nucleic acid sequence according to the first aspect of the present invention may optionally comprise or code for a poly(A) sequence. When present, such a poly(A) sequence comprises a sequence of about 25 to about 400 adenosine nucleotides, preferably a sequence of about 30 or, more preferably, of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to. Accordingly, the poly(A) sequence contains at least 25 or more than 25, more preferably, at least 30, more preferably at least 50 adenosine nucleotides. Therefore, such a poly (A) sequence does typically not contain less than 20 adenosine nucleotides. More particularly, it does not contain 10 and/or less than 10 adenosine nucleotides.

Preferably, the nucleic acid according of the present invention does not contain one or two or at least one or all but one or all of the components of the group consisting of: a sequence encoding a ribozyme (preferably a self-splicing ribozyme), a viral nucleic acid sequence, a histone stem-loop processing signal, in particular a histone-stem loop processing sequence derived from mouse histone H2A614 gene, a Neo gene, an inactivated promoter sequence and an inactivated enhancer sequence. Even more preferably, the nucleic acid according to the invention does not contain a ribozyme, preferably a self-splicing ribozyme, and one of the group consisting of: a Neo gene, an inactivated promoter sequence, an inactivated enhancer sequence, a histone stem-loop processing signal, in particular a histone-stem loop processing sequence derived from mouse histone H2A614 gene. Accordingly, the nucleic acid may in a preferred mode neither contain a ribozyme, preferably a self-splicing ribozyme, nor a Neo gene or, alternatively, neither a ribozyme, preferably a self-splicing ribozyme, nor any resistance gene (e.g. usually applied for selection). In another preferred mode, the nucleic acid of the invention may neither contain a ribozyme, preferably a self-splicing ribozyme nor a histone stem-loop processing signal, in particular a histone-stem loop processing sequence derived from mouse histone H2A614 gene.

Alternatively, according to the first aspect of the present invention, the inventive nucleic sequence optionally comprises a polyadenylation signal which is defined herein as a signal which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context a consensus polyadenylation signal is preferred comprising the NN(U/T)ANA consensus sequence. In a particular preferred aspect the polyadenylation signal comprises one of the following sequences: AA(U/T)AAA or A(U/T)(UIT)AAA (wherein uridine is usually present in RNA and thymidine is usually present in DNA). In some embodiments, the polyadenylation signal used in the inventive nucleic acid does not correspond to the U3 snRNA, U5, the polyadenylation processing signal from human gene G-CSF, or the SV40 polyadenylation signal sequences. In particular, the above polyadenylation signals are not combined with any antibiotics resistance gene (or any other reporter, marker or selection gene), in particular not with the resistance neo gene (neomycin phosphotransferase) (as the gene of the coding region according to element (a) of the inventive nucleic acid. And, any of the above polyadenylation signals are preferably not combined with the histone stem loop or the histone stem loop processing signal from mouse histone gene H2A614 in an inventive nucleic acid.

The inventive nucleic acid sequence according to the first aspect of the present invention furthermore encodes a protein or a peptide, which comprises an allergenic antigen or an autoimmune self-antigen or a fragment, variant or derivative thereof.

Such allergenic antigens may be selected from antigens derived from different sources, e.g. from animals, plants, fungi, bacteria, etc. Sources of allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are protein or peptide antigens and their fragments or epitopes, or nucleic acids and their fragments, particularly nucleic acids and their fragments, encoding such protein or peptide antigens and their fragments or epitopes.

Antigens associated with allergy or allergic disease (allergens or allergenic antigens) are preferably derived from a source selected from the list consisting of:
*Acarus* spp (Aca s 1, Aca s 10, Aca s 10.0101, Aca s 13, Aca s 13.0101, Aca s 2, Aca s 3, Aca s 7, Aca s 8), *Acanthocybium* spp (Aca so 1), *Acanthocheilonema* spp (Aca v 3, Aca v 3.0101), *Acetes* spp (Ace ja 1), *Actinidia* spp (Act a 1, Act c 1, Act c 10, Act c 10.0101, Act c 2, Act c 4, Act c 5, Act c 5.0101, Act c 8, Act c 8.0101, Act c Chitinase, Act d 1, Act d 1.0101, Act d 10, Act d 10.0101, Act d 10.0201, Act d 11, Act d 11.0101, Act d 2, Act d 2.0101, Act d 3, Act d 3.0101, Act d 3.02, Act d 4, Act d 4.0101, Act d 5, Act d 5.0101, Act d 6, Act d 6.0101, Act d 7, Act d 7.0101, Act d 8, Act d 8.0101, Act d 9, Act d 9.0101, Act d Chitinase, Act e 1, Act e 5), *Acyrthosiphon* spp (Acy pi 7, Acy pi 7.0101, Acy pi 7.0102), *Adenia* spp (Ade v RIP), *Aedes* spp (Aed a 1, Aed a 1.0101, Aed a 2, Aed a 2.0101, Aed a 3, Aed a 3.0101, Aed a 4, Aed a 7, Aed a 7.0101, Aed a 7.0102, Aed a 7.0103, Aed a 7.0104, Aed a 7.0105, Aed a 7.0106, Aed a 7.0107, Aed a 7.0108, Aed a 7.0109, Aed a 7.0110, Aed a 7.0111, Aed al 1, Aed al 3, Aed al 37kD, Aed v 37kD, Aed v 63kD), *Aegilops* spp (Aeg ta 28, Aeg ta alpha_Gliadin, Aeg um 28, Aeg un 28), *Aethaloperca* spp (Aet ro 1), *Agropyron* spp (Agr c 7), *Agrostis* spp (Agr ca 1, Agr ca 5, Agr g 1, Agr g 4, Agr s 5), *Agrobacterium* spp (Agr sp CP4 EPSPS), *Ailuropoda* spp (Ail me Phosvitin, Ail me TCTP), *Aix* spp (Aix ga 1, Aix sp 1), *Aleuroglyphus* spp (Ale o 1, Ale o 10, Ale o 10.0101, Ale o 10.0102, Ale o 13, Ale o 14, Ale o 2, Ale o 20, Ale o 3, Ale o 5, Ale o 7, Ale o 8, Ale o 9), *Allium* spp (All a 3, All a Alliin lyase, All c 3, All c 30kD, All c 4, All c Alliin lyase, All p Alliin lyase, All s Alliin lyase), *Alnus* spp (Aln g 1, Aln g 1.0101, Aln g 1/Bet v 1/Cor a 1 TPC7, Aln g 1/Bet v 1/Cor a 1 TPC9, Aln g 2, Aln g 4, Aln g 4.0101), Alopochen spp (Alo ae 1), *Alopecurus* spp (Alo p 1, Alo p 5), *Alternaria* spp (Alt a 1, Alt a 1.0101, Alt a 1.0102, Alt a 10, Alt a 10.0101, Alt a 12, Alt a 12.0101, Alt a 13, Alt a 13.0101, Alt a 2, Alt a 3, Alt a 3.0101, Alt a 4, Alt a 4.0101, Alt a 5, Alt a 5.0101, Alt a 6, Alt a 6.0101, Alt a 7, Alt a 7.0101, Alt a 70kD, Alt a 8, Alt a 8.0101, Alt a 9, Alt a MnSOD, Alt a NTF2, Alt a TCTP, Alt ar 1, Alt arg 1, Alt b 1, Alt bl 1, Alt br 1, Alt c 1, Alt ca 1, Alt ce 1, Alt ch 1, Alt ci 1, Alt co 1, Alt cr 1, Alt ct 1, Alt cu 1, Alt cy 1, Alt d 1, Alt du 1, Alt e 1, Alt et 1, Alt eu 1, Alt ga 1, Alt gr 1, Alt j 1, Alt 11, Alt lo 1, Alt m 1, Alt me 1, Alt mi 1, Alt mo 1, Alt o 1, Alt p 1, Alt ph 1, Alt po 1, Alt ps 1, Alt r 1, Alt s 1, Alt se 1, Alt sm 1, Alt so 1, Alt su 1, Alt t 1, Alt to 1, Alt to 1), *Amaranthus* spp (Ama r 2, Ama r 2.0101, Ama v 2, Ama v 2.0101, Ama v 2.0201), *Ambrosia* spp (Amb a 1, Amb a 1.0101, Amb a 1.0201, Amb a 1.0202, Amb a 1.0301, Amb a 1.0302, Amb a 1.0303, Amb a 1.0304, Amb a 1.0305, Amb a 1.0401, Amb a 1.0402, Amb a 1.0501, Amb a 1.0502, Amb a 10, Amb a 10.0101, Amb a 3, Amb a 3.0101, Amb a 4, Amb a 4.0101, Amb a 5, Amb a 5.0101, Amb a 6, Amb a 6.0101, Amb a 7, Amb a 7.0101, Amb a 8, Amb a 8.0101, Amb a 8.0102, Amb a 9, Amb a 9.0101, Amb a 9.0102, Amb a CPI, Amb p 1, Amb p 5, Amb p 5.0101, Amb p 5.0201, Amb t 5, Amb t 5.0101, Amb t 8), *Ammothea* spp (Amm h 7, Amm h 7.0101), *Anadara* spp (Ana br 1), *Ananas* spp (Ana c 1, Ana c 1.0101, Ana c 2, Ana c 2.0101, Ana c 2.0101 (MUXF3)), *Anas* spp (Ana ca 1), *Anarhichas* spp (Ana l 1),

*Anacardium* spp (Ana o 1, Ana o 1.0101, Ana o 1.0102, Ana o 2, Ana o 2.0101, Ana o 3, Ana o 3.0101), *Anas* spp (Ana p 1, Ana p 2, Ana p 3), *Anguilla* spp (Ang a 1, Ang j 1), *Anisakis* spp (Ani s 1, Ani s 1.0101, Ani s 10, Ani s 10.0101, Ani s 11, Ani s 11.0101, Ani s 12, Ani s 12.0101, Ani s2, Ani s 2.0101, Ani s 24kD, Ani s 3, Ani s 3.0101, Ani s 4, Ani s 4.0101, Ani s 5, Ani s 5.0101, Ani s 6, Ani s 6.0101, Ani s 7, Ani s 7.0101, Ani s 8, Ani s 8.0101, Ani s 9, Ani s 9.0101, Ani s CCOS3, Ani s Cytochrome B, Ani s FBPP, Ani s NADHDS4L, Ani s NARaS, Ani s PEPB, Ani s Troponin), *Annona* spp (Ann c Chitinase), *Anopheles* spp (Ano da 17, Ano da 17.0101, Ano da 27, Ano da 27.0101, Ano da 7, Ano da 7.0101, Ano g 7, Ano g 7.0101), Anser spp (Ans a 1, Ans a 2, Ans a 3, Ans in 1), *Anthoxanthum* spp (Ant o 1, Ant o 1.0101, Ant o 12, Ant o 13, Ant o 2, Ant o 4, Ant o 5, Ant o 6, Ant o 7), Apis spp (Api c 1, Api c 1.0101, Api c 10, Api c 2, Api c 4, Api d 1, Api d 1.0101, Api d 4, Api fl 4), *Apium* spp (Api g 1, Api g 1.0101, Api g 1.0201, Api g 2, Api g 2.0101, Api g 3, Api g 3.0101, Api g 4, Api g 4.0101, Api g 5, Api g 5.0101, Api g 6, Api g 6.0101), Apis spp (Api m 1, Api m 1.0101, Api m 10, Api m 10.0101, Api m 11, Api m 11.0101, Api m 11.0201, Api m 13kD, Api m 2, Api m 2.0101, Api m 3, Api m 3.0101, Api m 4, Api m 4.0101, Api m 5, Api m 5.0101, Api m 6, Api m 6.0101, Api m 7, Api m 7.0101, Api m 8, Api m 8.0101, Api m 9, Api m 9.0101, Api m A1-A2, Api m A1-A2-A3, Api m Apalbumin 1, Api m Apalbumin 2, Api me 1, Api me 4), *Arachis* spp (Ara d 2, Ara d 6, Ara f 3, Ara f 4, Ara h 1, Ara h 1.0101, Ara h 10, Ara h 10.0101, Ara h 10.0102, Ara h 11, Ara h 11.0101, Ara h 2, Ara h 2.0101, Ara h 2.0102, Ara h 2.0201, Ara h 2.0202, Ara h 3, Ara h 3.0101, Ara h 4, Ara h 4.0101, Ara h 5, Ara h 5.0101, Ara h 6, Ara h 6.0101, Ara h 7, Ara h 7.0101, Ara h 7.0201, Ara h 7.0202, Ara h 8, Ara h 8.0101, Ara h 8.0201, Ara h 9, Ara h 9.0101, Ara h 9.0201, Ara h Agglutinin, Ara h Oleosin 18kD, Ara i 2, Ara i 6), *Arabidopsis* spp (Ara t 3, Ara t 8, Ara t GLP), *Archosargus* spp (Arc pr 1), *Archaeopotamobius* spp (Arc s 8, Arc s 8.0101), *Aequipecten* spp (Arg i 1), *Argas* spp (Arg r 1, Arg r 1.0101), *Ariopsis* spp (Ari fe 1), *Armoracia* spp (Arm r HRP), *Arrhenatherum* spp (Arr e 1, Arr e 5), *Artemisia* spp (Art a 1, Art ap 1), *Artemia* spp (Art fr 1, Art fr 1.0101, Art fr 5, Art fr 5.0101), *Arthrobacter* spp (Art gl CO), *Achorion* spp (Art gy 7), *Artocarpus* spp (Art h 17kD, Art h 4), *Arthrospira* spp (Art pl beta_Phycocyanin), *Artemisia* spp (Art v 1, Art v 1.0101, Art v 1.0102, Art v 1.0103, Art v 1.0104, Art v 1.0105, Art v 1.0106, Art v 1.0107, Art v 2, Art v 2.0101, Art v 3, Art v 3.0101, Art v 3.0201, Art v 3.0202, Art v 3.0301, Art v 4, Art v 4.0101, Art v 4.0201, Art v 47kD, Art v 5, Art v 5.0101, Art v 6, Art v 6.0101, Art v 60kD), *Arthroderma* spp (Art va 4), *Ascaris* spp (Asc I 3, Asc I 3.0101, Asc I 3.0102, Asc I 34kD, Asc s 1, Asc s 1.0101, Asc s 3, Asc s 3.0101, Asc s GST), *Aspergillus* spp (Asp aw Glucoamylase, Asp c 22, Asp f 1, Asp f 1.0101, Asp f 10, Asp f 10.0101, Asp f 11, Asp f 11.0101, Asp f 12, Asp f 12.0101, Asp f 13, Asp f 13.0101, Asp f 15, Asp f 15.0101, Asp f 16, Asp f 16.0101, Asp f 17, Asp f 17.0101, Asp f 18, Asp f 18.0101, Asp f 2, Asp f 2.0101, Asp f 22, Asp f 22.0101, Asp f 23, Asp f 23.0101, Asp f 27, Asp f 27.0101, Asp f 28, Asp f 28.0101, Asp f 29, Asp f 29.0101, Asp f 3, Asp f 3.0101, Asp f 34, Asp f 34.0101, Asp f 4, Asp f 4.0101, Asp f 5, Asp f 5.0101, Asp f 56kD, Asp f 6, Asp f 6.0101, Asp f 7, Asp f 7.0101, Asp f 8, Asp f 8.0101, Asp f 9, Asp f 9.0101, Asp f AfCalAp, Asp f AT_V, Asp f Catalase, Asp f Chitosanase, Asp f CP, Asp f DPPV, Asp f FDH, Asp f gamma_Actin, Asp f Glucosidase, Asp f GPI, Asp f GST, Asp f GT, Asp f IAO, Asp f IPMI, Asp f LPL1, Asp f LPL3, Asp f Mannosidase, Asp f MDH, Asp f PL, Asp f PUP, Asp f RPS3, Asp f SXR, Asp fl 13, Asp fl 13.0101, Asp fl 18, Asp fl 2, Asp fl 21, Asp fl 3, Asp fl 4, Asp fl 7, Asp fl 8, Asp fl 9, Asp me Seaprose, Asp n 14, Asp n 14.0101, Asp n 18, Asp n 18.0101, Asp n 25, Asp n 25.0101, Asp n 30, Asp n Glucoamylase, Asp n Hemicellulase, Asp n Pectinase, Asp o 13, Asp o 13.0101, Asp o 21, Asp o 21.0101, Asp o 3, Asp o 4, Asp o 7, Asp o 8, Asp o Lactase, Asp o Lipase, Asp oc 13, Asp r 1, Asp sa AP, Asp sp Glucoamylase, Asp sp Glucoseoxidase, Asp sp PL, Asp sp PME, Asp sy 13, Asp v 13, Asp v 13.0101, Asp v Catalase A, Asp v *Enolase*, Asp v GAPDH, Asp v MDH, Asp v SXR), *Asparagus* spp (Aspa o 1, Aspa o 1.01, Aspa o 1.02, Aspa o 17kD, Aspa o 4), *Aspergillus* spp (Aspe ni 2, Aspe ni 3, Aspe ni 4, Aspe ni 7, Aspe ni 8, Aspe ni 9), *Avena* spp (Ave s 1, Ave s 12, Ave s 13, Ave s 2, Ave s 4, Ave s 5, Ave s 7), *Babylonia* spp (Bab ja 1), *Bacillus* spp (Bac at Subtilisin, Bac cl Subtilisin, Bac l Subtilisin, Bac li aA, Bac li Subtilisin), *Bactrocera* spp (Bac of 27, Bac of 27.0101), *Bacillus* spp (Bac sp aA1, Bac sp aA3, Bac sp Decarboxylase, Bac st amyM, Bac su Subtilisin, Bac t Cryl Ab, Bac t Cryl Fa, Bac t Cry3Bbl, Bac t Cry9c), *Bagre* spp (Bag ma 1), *Balistes* spp (Bal ca 1), *Balanus* spp (Bal r 1, Bal r 1.0101), *Beauveria* spp (Bea b Ald, Bea b Enol, Bea b f2, Bea b Hex), *Bertholletia* spp (Ber e 1, Ber e 1.0101, Ber e 2, Ber e 2.0101), *Beryx* spp (Ber sp 1), *Betula* spp (Bet ab 1, Bet al 1, Bet ch 1, Bet co 1, Bet da 1, Bet gr 1, Bet hu 1, Bet le 1, Bet me 1, Bet n 1, Bet p 1, Bet pa 1, Bet po 1, Bet pu 1, Bet pu 2, Bet pu 4, Bet pu 6, Bet pu 7, Bet sc 1, Bet ut 1, Bet v 1, Bet v 1B1-B1-B1, Bet v 1 fv Mal 4x, Bet v 1.0101, Bet v 1.0102, Bet v 1.0103, Bet v 1.0201, Bet v 1.0301, Bet v 1.0401, Bet v 1.0402, Bet v 1.0501, Bet v 1.0601, Bet v 1.0602, Bet v 1.0701, Bet v 1.0801, Bet v 1.0901, Bet v 1.1001, Bet v 1.1101, Bet v 1.1201, Bet v 1.1301, Bet v 1.1401, Bet v 1.1402, Bet v 1.1501, Bet v 1.1502, Bet v 1.1601, Bet v 1.1701, Bet v 1.1801, Bet v 1.1901, Bet v 1.2001, Bet v 1.2101, Bet v 1.2201, Bet v 1.2301, Bet v 1.2401, Bet v 1.2501, Bet v 1.2601, Bet v 1.2701, Bet v 1.2801, Bet v 1.2901, Bet v 1.3001, Bet v 1.3101, Bet v 2, Bet v 2.0101, Bet v 3, Bet v 3.0101, Bet v 4, Bet v 4.0101, Bet v 6, Bet v 6.0101, Bet v 6.0102, Bet v 7, Bet v 7.0101, Bet v 8, Bet v Glucanase), *Beta* spp (Beta v 1, Beta v 1.0101, Beta v 2, Beta v 2.0101), *Blattella* spp (Bla g 1, Bla g 1.0101, Bla g 1.0102, Bla g 1.0103, Bla g 1.0201, Bla g 1.0202, Bla g 2, Bla g 2.0101, Bla g 2.0201, Bla g 36kD, Bla g 4, Bla g 4.0101, Bla g 4.0201, Bla g 5, Bla g 5.0101, Bla g 5.0201, Bla g 6, Bla g 6.0101, Bla g 6.0201, Bla g 6.0301, Bla g 7, Bla g 7.0101, Bla g 8, Bla g 8.0101, Bla g 9, Bla g *Enolase*, Bla g GSTD1, Bla g RACK1, Bla g TPI, Bla g Trypsin, Bla g Vitellogenin), *Blatta* spp (Bla o 1, Bla o 7), *Blomia* spp (Blo t 1, Blo t 1.0101, Blo t 1.0201, Blo t 10, Blo t 10.0101, Blo t 10.0102, Blo t 11, Blo t 11.0101, Blo t 12, Blo t 12.0101, Blo t 12.0102, Blo t 13, Blo t 13.0101, Blo t 14, Blo t 15, Blo t 18, Blo t 19, Blo t 19.0101, Blo t 2, Blo t 2.0101, Blo t 2.0102, Blo t 2.0103, Blo t 20, Blo t 21, Blo t 21.0101, Blo t 3, Blo t 3.0101, Blo t 4, Blo t 4.0101, Blo t 5, Blo t 5.0101, Blo t 6, Blo t 6.0101, Blo t 7, Blo t 8, Blo t 9, Blo t HSP70), *Bombus* spp (Bom ar 4, Bom by 4, Bom p 1, Bom p 1.0101, Bom p 2, Bom p 3, Bom p 4, Bom p 4.0101, Bom t 1, Bom t 1.0101, Bom t 4, Bom t 4.0101), *Bombyx* spp (Bomb m 1, Bomb m 1.0101, Bomb m 7, Bomb m 7.0101, Bomb m 7.0102, Bomb m 7.0103, Bomb m 7.0104, Bomb m 7.0105, Bomb m 7.0106), *Boophilus* spp (Boo m 1, Boo m 7, Boo m 7.0101), Bos spp (Bos d 2, Bos d 2.0101, Bos d 2.0102, Bos d 2.0103, Bos d 3, Bos d 3.0101, Bos d 4, Bos d 4.0101, Bos d 5, Bos d 5.0101, Bos d 5.0102, Bos d 6, Bos d 6 (MDA), Bos d 6.0101, Bos d 7, Bos d 7.0101, Bos d 8, Bos d 8 alphaS1, Bos d 8 alphaS2, Bos d 8 beta, Bos d 8 kappa, Bos d alpha2l, Bos d alpha2l.0101, Bos d Chymosin, Bos d Fibrin, Bos d Gelatin, Bos d HG, Bos d Insulin, Bos d Lactoferrin, Bos d Lactoperoxidase, Bos d Myoglobin, Bos d OBP, Bos d OSCP, Bos d Phosvitin, Bos d PLA2, Bos d PRVB, Bos d Thrombin, Bos d TI, Bos gr ALA, Bos gr Myoglobin), *Bothrops* spp (Bot as 1, Bot at 1), *Bouteloua* spp (Bou g 1), *Biting* spp (Boy ov 1), *Brama* spp (Bra du 1), *Brassica* spp (Bra j 1, Bra j 1.0101, Bra n 1, Bra n 1.0101, Bra n 4, Bra n 7, Bra n 8, Bra n PG, Bra ni 8, Bra o 3, Bra o 3.0101, Bra r 1, Bra r 1.0101, Bra r 2, Bra r 2.0101, Bra r 3, Bra r 4, Bra r 7), *Bromus* spp (Bro a 1, Bro a 4), Brosme spp (Bro br 1), *Bromus* spp (Bro i 1, Bro i 5, Bro i 7), *Brugia* spp (Bru m 3, Bru m 3.0101, Bru m Bm33), *Bubalus* spp (Bub b ALA, Bub b BLG, Bub b Casein, Bub b Casein alphaS1, Bub b Casein alphaS2, Bub b Casein beta, Bub b Casein kappa), *Caenorhabditis* spp (Cae b 3, Cae b 3.0101, Cae br 3, Cae br 3.0101, Cae e 3, Cae e 3.0101, Cae e 3.0102, Cae re 13, Cae re 13.0101), *Cajanus* spp (Caj c 1), *Caligus* spp (Cal cl 1, Cal cl 1.0101, Cal cl 1.0102), *Calamus* spp (Cal le 1), *Callinectes* spp (Cal s 2), *Camelus* spp (Cam d ALA, Cam d Casein, Cam d Casein alphaS1, Cam d Casein alphaS2, Cam d Casein beta, Cam d Casein kappa), *Camponotus* spp (Cam fl 7, Cam fl 7.0101), *Canis* spp (Can f 1, Can f 1.0101, Can f 2, Can f 2.0101, Can f 3, Can f 3.0101, Can f 4, Can f 4.0101, Can f 5, Can f 5.0101, Can f 6, Can f 6.0101, Can f Feld1-like, Can f Homs2-like, Can f Phosvitin, Can f TCTP), *Canthidermis* spp (Can ma 1), *Cancer* spp (Can mg 2, Can p 1), *Cannabis* spp (Can s 3), *Candida* spp (Cand a 1, Cand a 1.0101, Cand a 3, Cand a 3.0101, Cand a CAAP, Cand a CyP, Cand a *Enolase*, Cand a FPA, Cand a MnSOD, Cand a PGK, Cand b 2, Cand b 2.0101, Cand b FDH, Cand r Lipase), *Capsicum* spp (Cap a 1, Cap a 1.0101, Cap a 17kD, Cap a 2, Cap a 2.0101, Cap a 30kD, Cap a Glucanase, Cap ch 17kD), *Caprella* spp (Cap e 1), *Capra* spp (Cap h ALA, Cap h BLG, Cap h Casein, Cap h Casein alphaS1, Cap h Casein alphaS2, Cap h Casein beta, Cap h Casein kappa, Cap h GSA), *Capitulum* spp (Cap m 1), *Carassius* spp (Car au 1), *Carpinus* spp (Car b 1, Car b 1.0101, Car b 1.0102, Car b 1.0103, Car b 1.0104, Car b 1.0105, Car b 1.0106, Car b 1.0107, Car b 1.0108, Car b 1.0109, Car b 1.0110, Car b 1.0111, Car b 1.0112, Car b 1.0113, Car b 1.0201, Car b 1.0301, Car b 1.0302, Car b 2, Car b 4), *Caranx* spp (Car cr 1), *Carya* spp (Car i 1, Car i 1.0101, Car i 2, Car i 4, Car i 4.0101), *Carcinus* spp (Car ma 2), *Caryota* spp (Car mi 2), *Carica* spp (Car p 1, Car p Chitinase, Car p Chymopapain, Car p Endoproteinase), *Castanea* spp (Cas c 24kD, Cas s 1, Cas s 1.0101, Cas s 1.0102, Cas s 1.0103, Cas s 2, Cas s 5, Cas s 5.0101, Cas s 8, Cas s 8.0101, Cas s 9, Cas s 9.0101), *Catharanthus* spp (Cat r 1, Cat r 1.0101, Cat r 17kD, Cat r 2), *Caulolatilus* spp (Cau ch 1), *Cavia* spp (Cav p 1, Cav p 1.0101, Cav p 2, Cav p 2.0101, Cav p 3, Cav p 3.0101, Cav p Gelatin, Cav p GSA), *Centropristis* spp (Cen s 1), *Cephalopholis* spp (Cep so 1), *Charybdis* spp (Cha f 1, Cha f 1.0101), Chaetodipterus spp (Cha fa 1), *Chamaecyparis* spp (Cha o 1, Cha o 1.0101, Cha o 2, Cha o 2.0101), *Chenopodium* spp (Che a 1, Che a 1.0101, Che a 2, Che a 2.0101, Che a 3, Che a 3.0101), *Chironomus* spp (Chi k 1, Chi k 10, Chi k 10.0101), *Chinchilla* spp (Chi 121kD_a, Chi 121kD_b), *Chionoecetes* spp (Chi o 1, Chi o 1.0101, Chi o 2, Chi o 4, Chi o 6, Chi o alpha_Actin, Chi o SERCA), *Chironomus* spp (Chi t 1, Chi t 1.0101, Chi t 1.0201, Chi t 2, Chi t 2.0101, Chi t 2.0102, Chi t 3, Chi t 3.0101, Chi t 4, Chi t 4.0101, Chi t 5, Chi t 5.0101, Chi t 6, Chi t 6.0101, Chi t 6.0201, Chi t 7, Chi t 7.0101, Chi t 8, Chi t 8.0101, Chi t 9, Chi t 9.0101), *Chlamys* spp (Chl n 1), *Chloephaga* spp (Chl pi 1), *Chortoglyphus* spp (Cho a 10), *Chrysomela* spp (Chr tr 7, Chr tr 7.0101), *Cicer* spp (Cic a 2S Albumin, Cic a Albumin), *Cichorium* spp (Cic i 1), *Cimex* spp (Cim I Nitrophorin), Citrus spp (Cit I 1, Cit I 3, Cit I 3.0101), *Citrullus* spp (Cit la 2, Cit la MDH, Cit la TPI), Citrus spp (Cit r 3, Cit r 3.0101, Cit s 1, Cit s 1.0101, Cit s 2, Cit s 2.0101, Cit s 3, Cit s 3.0101, Cit s 3.0102, Cit s IFR), *Cladosporium* spp (Cla c 14, Cla c 14.0101, Cla c 9, Cla c 9.0101, Cla h 1, Cla h 10, Cla h 10.0101, Cla h 12, Cla h 12.0101, Cla h 2, Cla h 2.0101, Cla h 42kD, Cla h 5, Cla h 5.0101, Cla h 6, Cla h 6.0101, Cla h 7, Cla h 7.0101, Cla h 8, Cla h 8 CSP, Cla h 8.0101, Cla h 9, Cla h 9.0101, Cla h abH, Cla h GST, Cla h HCh1, Cla h HSP70, Cla h NTF2, Cla h TCTP), *Clostridium* spp (Clo hi Collagenase, Clo t Toxoid), *Clupea* spp (Clu h 1, Clu h 1.0101, Clu h 1.0201, Clu h 1.0301), *Cocos* spp (Coc n 2, Coc n 4, Coc n 5), *Coccidioides* spp (Coc po 8), *Coffea* spp (Cof a 1, Cof a 1.0101), *Columba* spp (Col l PSA), *Coprinus* spp (Cop c 1, Cop c 1.0101, Cop c 2, Cop c 2.0101, Cop c 3, Cop c 3.0101, Cop c 4, Cop c 5, Cop c 5.0101, Cop c 6, Cop c 7, Cop c 7.0101), *Corylus* spp (Cor a 1, Cor a 1.0101, Cor a 1.0102, Cor a 1.0103, Cor a 1.0104, Cor a 1.0201, Cor a 1.0301, Cor a 1.0401, Cor a 1.0402, Cor a 1.0403, Cor a 1.0404, Cor a 10, Cor a 10.0101, Cor a 11, Cor a 11.0101, Cor a 12, Cor a 12.0101, Cor a 13, Cor a 13.0101, Cor a 14, Cor a 14.0101, Cor a 2, Cor a 2.0101, Cor a 2.0102, Cor a 8, Cor a 8.0101, Cor a 9, Cor a 9.0101), *Corynebacterium* spp (Cor d Toxoid), *Corylus* spp (Cor he 1), *Coryphaena* spp (Cor hi 1), *Coriandrum* spp (Cor s 1, Cor s 11 kD, Cor s 2), *Cotoneaster* spp (Cot l 3), *Crangon* spp (Cra c 1, Cra c 1.0101, Cra c 2, Cra c 2.0101, Cra c 4, Cra c 4.0101, Cra c 5, Cra c 5.0101, Cra c 6, Cra c 6.0101, Cra c 8, Cra c 8.0101), *Crassostrea* spp (Cra g 1), *Cricetus* spp (Cri c HSA), *Crivellia* spp (Cri pa 1), *Crocus* spp (Cro s 1, Cro s 1.0101, Cro s 2, Cro s 2.0101, Cro s 3, Cro s 3.01, Cro s 3.02), *Cryptomeria* spp (Cry j 1, Cry j 1.0101, Cry j 1.0102, Cry j 1.0103, Cry j 2, Cry j 2.0101, Cry j 2.0102, Cry j 3, Cry j 3.1, Cry j 3.2, Cry j 3.3, Cry j 3.4, Cry j 3.5, Cry j 3.6, Cry j 3.7, Cry j 3.8, Cry j 4, Cry j AP, Cry j Chitinase, Cry j CPA9, Cry j IFR, Cry j LTP, Cry j P1-P2), *Cryphonectria* spp (Cry p AP), *Ctenocephalides* spp (Cte f 1, Cte f 1.0101, Cte f 2, Cte f 2.0101, Cte f 3, Cte f 3.0101), *Ctenopharyngodon* spp (Cte id 1), *Cucumis* spp (Cuc m 1, Cuc m 1.0101, Cuc m 2, Cuc m 2.0101, Cuc m 3, Cuc m 3.0101, Cuc m Lec17, Cuc m MDH), *Cucurbita* spp (Cuc ma 18kD, Cuc ma 2, Cuc p 2, Cuc p AscO), *Cucumis* spp (Cuc s 2), *Culicoides* spp (Cul n 1, Cul n 10, Cul n 11, Cul n 2, Cul n 3, Cul n 4, Cul n 5, Cul n 6, Cul n 7, Cul n 8, Cul n 9, Cul n HSP70), *Culex* spp (Cul q 28kD, Cul q 35kD, Cul q 7, Cul q 7.0101, Cul q 7.0102), *Culicoides* spp (Cul so 1), *Cuminum* spp (Cum c 1, Cum c 2), *Cupressus* spp (Cup a 1, Cup a 1.0101, Cup a 1.02, Cup a 2, Cup a 3, Cup a 4, Cup a 4.0101, Cup s 1, Cup s 1.0101, Cup s 1.0102, Cup s 1.0103, Cup s 1.0104, Cup s 1.0105, Cup s 3, Cup s 3.0101, Cup s 3.0102, Cup s 3.0103, Cup s 8), *Cochliobolus* spp (Cur 11, Cur l 1.0101, Cur 12, Cur l 2.0101, Cur 13, Cur l 3.0101, Cur l 4, Cur l 4.0101, Cur l ADH, Cur l GST, Cur l MnSOD, Cur l Oryzin, Cur l Trx, Cur l ZPS1), *Cyanochen* spp (Cya cy 1), *Cynoscion* spp (Cyn ar 1), *Cynosurus* spp (Cyn cr 1, Cyn cr 5), *Cynodon* spp (Cyn d 1, Cyn d 1.0101, Cyn d 1.0102, Cyn d 1.0103, Cyn d 1.0104, Cyn d 1.0105, Cyn d 1.0106, Cyn d 1.0107, Cyn d 1.0201, Cyn d 1.0202, Cyn d 1.0203, Cyn d 1.0204, Cyn d 10, Cyn d 11, Cyn d 12, Cyn d 12.0101, Cyn d 13, Cyn d 15, Cyn d 15.0101, Cyn d 2, Cyn d 22, Cyn d 22.0101, Cyn d 23, Cyn d 23.0101, Cyn d 24, Cyn d 24.0101, Cyn d 4, Cyn d 5, Cyn d 6, Cyn d 7, Cyn d 7.0101), *Cynoscion* spp (Cyn ne 1), *Cynomys* spp (Cyn sp Lipocalin), *Cyprinus* spp (Cyp c 1, Cyp c 1.01, Cyp c 1.02), Daboia spp (Dab ru 1), *Dactylis* spp (Dac g 1, Dac g 1.01, Dac g 1.0101, Dac g 1.02, Dac g 12, Dac g 13, Dac g 2, Dac g 2.0101, Dac g 3, Dac g 3.0101, Dac g 4, Dac g 4.0101, Dac g 5, Dac g 5.0101, Dac g 7), *Dama* spp (Dam d CSA), *Danio* spp (Dan re 1, Dan re 2, Dan re alpha2I, Dan re CK), *Dasyatis* spp (Das ak 1, Das am 1, Das sa 1), *Daucus* spp (Dau c 1, Dau c 1.0101, Dau c 1.0102, Dau c 1.0103, Dau c 1.0104, Dau c 1.0105, Dau c 1.0201, Dau c 1.0301, Dau c 3, Dau c 4, Dau c 4.0101, Dau c CyP), *Decapterus* spp (Dec ru 1), *Dendronephthya* spp (Den n 1, Den n 1.0101), *Dermatophagoides* spp (Der f 1, Der f 1.0101, Der f 1.0102, Der f 1.0103, Der f 1.0104, Der f 1.0105, Der f 1.0106, Der f 1.0107, Der f 1.0108, Der f 1.0109, Der f 1.0110, Der f 10, Der f 10.0101, Der f 10.0102, Der f 11, Der f 11.0101, Der f 13, Der f 13.0101, Der f 14, Der f 14.0101, Der f 15, Der f 15.0101, Der f 16, Der f 16.0101, Der f 17, Der f 17.0101, Der f 18, Der f 18.0101, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 21, Der f 22, Der f 22.0101, Der f 3, Der f 3.0101, Der f 4, Der f 5, Der f 6, Der f 6.0101, Der f 7, Der f 7.0101, Der f 8, Der f 9, Der f HSP70), *Dermanyssus* spp (Der g 10, Der g 10.0101), *Dermatophagoides* spp (Der m 1, Der m 1.0101, Der p 1, Der p 1.0101, Der p 1.0102, Der p 1.0103, Der p 1.0104, Der p 1.0105, Der p 1.0106, Der p 1.0107, Der p 1.0108, Der p 1.0109, Der p 1.0110, Der p 1.0111, Der p 1.0112, Der p 1.0113, Der p 1.0114, Der p 1.0115, Der p 1.0116, Der p 1.0117, Der p 1.0118, Der p 1.0119, Der p 1.0120, Der p 1.0121, Der p 1.0122, Der p 1.0123, Der p 1.0124, Der p 10, Der p 10.0101, Der p 10.0102, Der p 10.0103, Der p 11, Der p 11.0101, Der p 13, Der p 14, Der p 14.0101, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p 2.0110, Der p 2.0111, Der p 2.0112, Der p 2.0113, Der p 2.0114, Der p 2.0115, Der p 20, Der p 20.0101, Der p 21, Der p 21.0101, Der p 23, Der p 23.0101, Der p 3, Der p 3.0101, Der p 4, Der p 4.0101, Der p 5, Der p 5.0101, Der p 5.0102, Der p 6, Der p 6.0101, Der p 7, Der p 7.0101, Der p 8, Der p 8.0101, Der p 9, Der p 9.0101, Der p 9.0102, Der p P1-P2, Der p P2-P1, Der s 1, Der s 2, Der s 3), *Dianthus* spp (Dia c RIP), *Dicranopteris* spp (Dic l 2S Albumin), *Diospyros* spp (Dio k 17kD, Dio k 4, Dio k IFR), *Dioscorea* spp (Dio p TSP), *Diplodus* spp (Dip ho 1), *Distichlis* spp (Dis s 1, Dis s 7), *Ditrema* spp (Dit to 1), *Dolichovespula* spp (Dol a 1, Dol a 2, Dol a 5, Dol a 5.0101), *Dolichos* spp (Dol b Agglutinin), *Dolichovespula* spp (Dol m 1, Dol m 1.0101, Dol m 1.02, Dol m 2, Dol m 2.0101, Dol m 5, Dol m 5.0101, Dol m 5.02), *Drosophila* spp (Dro an 7, Dro an 7.0101, Dro er 7, Dro er 7.0101, Dro er 7.0102, Dro gr 7, Dro gr 7.0101, Dro gr 7.0102, Dro m 7, Dro m 7.0101, Dro m 7.0102, Dro m 7.0103, Dro m 7.0104, Dro m 7.0105, Dro m 7.0106, Dro m 7.0107, Dro m 7.0108, Dro m 7.0109, Dro m 7.0110, Dro m 7.0111, Dro m 7.0112, Dro m 7.0113, Dro m 9, Dro m MnSOD, Dro mo 7, Dro mo 7.0101, Dro pp 7, Dro pp 7.0101, Dro se 7, Dro se 7.0101, Dro si 7, Dro si 7.0101, Dro si 7.0102, Dro vi 7, Dro vi 7.0101, Dro wi 7, Dro wi 7.0101, Dro y 7, Dro y 7.0101, Dro y 7.0102, Dro y 7.0103), *Echium* spp (Ech p Cytochrome C), *Elaeis* spp (Ela g 2, Ela g Bd31kD), *Elops* spp (Elo sa 1), *Embellisia* spp (Emb a 1, Emb i 1, Emb nz 1, Emb t 1), *Engraulis* spp (Eng e 1), *Enteroctopus* spp (Ent d 1), *Epinephelus* spp (Epi bl 1, Epi co 1, Epi fl 1, Epi mc 1, Epi mo 1), *Epicoccum* spp (Epi p 1, Epi p 1.0101, Epi p 12kD, Epi p GST), *Epinephelus* spp (Epi po 1, Epi un 1), *Equisetum* spp (Equ a 17kD), *Equus* spp (Equ as 4, Equ as DSA, Equ bu 4, Equ c 1, Equ c 1.0101, Equ c 2, Equ c 2.0101, Equ c 2.0102, Equ c 3, Equ c 3.0101, Equ c 4, Equ c 4.0101, Equ c 5, Equ c 5.0101, Equ c ALA, Equ c BLG, Equ c Casein, Equ c Casein beta, Equ c Casein kappa, Equ c PRVB, Equ he 4, Equ z ZSA), *Erimacrus* spp (Eri i 1, Eri i 1.0101, Eri i 1.0102), *Eriocheir* spp (Eri s 1, Eri s 1.0101, Eri s 2), *Erwinia* spp (Erw ch Asparaginase), *Escherichia* spp (Esc c Asparaginase, Esc c beta GAL), *Esox* spp (Eso l 1), *Euphausia* spp (Eup p 1, Eup p 1.0101), *Euphasia* spp (Eup s 1, Eup s 1.0101), *Euroglyphus* spp (Eur m 1, Eur m 1.0101, Eur m 1.0102, Eur m 1.0103, Eur m 10, Eur m 14, Eur m 14.0101, Eur m 2, Eur m 2.0101, Eur m 2.0102, Eur m 3, Eur m 3.0101, Eur m 4, Eur m 4.0101), *Evynnis* spp (Evy j 1), *Fagopyrum* spp (Fag e 1, Fag e 1.0101, Fag e 10kD, Fag e 19kD, Fag e 2, Fag e 2.0101, Fag e TI), *Fagus* spp (Fag s 1, Fag s 1.0101, Fag s 2, Fag s 4), *Fagopyrum* spp (Fag t 1, Fag t 10kD, Fag t 2, Fag t 2.0101), *Felis* spp (Fel d 1, Fel d 1.0101, Fel d 2, Fel d 2.0101, Fel d 3, Fel d 3.0101, Fel d 4, Fel d 4.0101, Fel d 5, Fel d 5.0101, Fel d 6, Fel d 6.0101, Fel d 7, Fel d 7.0101, Fel d 8, Fel d 8.0101, Fel d IgG), *Fenneropenaeus* spp (Fen c 1, Fen c 2, Fen me 1, Fen me 1.0101), *Festuca* spp (Fes e 1, Fes e 13, Fes e 4, Fes e 5, Fes e 7, Fes p 1, Fes p 13, Fes p 4, Fes p 4.0101, Fes p 5, Fes r 1, Fes r 5), *Ficus* spp (Fic c 17kD, Fic c 4, Fic c Ficin), *Foeniculum* spp (Foe v 1, Foe v 2), *Forsythia* spp (For s 1), *Forcipomyia* spp (For t 1, For t 1.0101, For t 2, For t 2.0101, For t 7, For t FPA, For t Myosin, For t TPI), *Fragaria* spp (Fra a 1, Fra a 1.0101, Fra a 3, Fra a 3.0101, Fra a 3.0102, Fra a 3.0201, Fra a 3.0202, Fra a 3.0203, Fra a 3.0204, Fra a 3.0301, Fra a 4, Fra a 4.0101, Fra c 1), *Fraxinus* spp (Fra e 1, Fra e 1.0101, Fra e 1.0102, Fra e 1.0201, Fra e 12, Fra e 2, Fra e 3, Fra e 9), *Fragaria* spp (Fra v 1), *Fusarium* spp (Fus c 1, Fus c 1.0101, Fus c 2, Fus c 2.0101, Fus c 3, Fus s 1, Fus s 45kD, Fus sp Lipase), *Gadus* spp (Gad c 1, Gad c 1.0101, Gad c APDH, Gad m 1, Gad m 1.0101, Gad m 1.0102, Gad m 1.0201, Gad m 1.0202, Gad m 45kD, Gad m Gelatin, Gad ma 1), *Gallus* spp (Gal d 1, Gal d 1.0101, Gal d 2, Gal d 2.0101, Gal d 3, Gal d 3.0101, Gal d 4, Gal d 4.0101, Gal d 5, Gal d 5.0101, Gal d 6, Gal d 6.0101, Gal d Apo I, Gal d Apo VI, Gal d GPI, Gal d HG, Gal d IgY, Gal d L-PGDS, Gal d Ovomucin, Gal d Phosvitin, Gal d PRVB, Gal la 4), *Galleria* spp (Gal m 18kD, Gal m 24kD), *Gallus* spp (Gal so 4), *Gammarus* spp (Gam s TM), *Gelonium* spp (Gel m RIP), *Geothelphusa* spp (Geo de 1), *Glossina* spp (Glo m 5, Glo m 5.0101, Glo m 7, Glo m 7.0101, Glo m 7.0102, Glo m 7.0103), *Glycine* spp (Gly a Bd30K, Gly ar Bd30K, Gly ca Bd30K, Gly cl Bd30K, Gly cu Bd30K, Gly cy Bd30K), *Glycyphagus* spp (Gly d 10, Gly d 10.0101, Gly d 13, Gly d 2, Gly d 2.0101, Gly d 2.0201, Gly d 2.03, Gly d 2/Lep d 2 L1, Gly d 2/Lep d 2 L2, Gly d 2/Lep d 2 L3, Gly d 2/Lep d 2 L4, Gly d 2/Lep d 2 R1, Gly d 2/Lep d 2 R2, Gly d 2/Lep d 2 R3, Gly d 2/Lep d 2 R4, Gly d 2/Lep d 2 R5, Gly d 20, Gly d 3, Gly d 5, Gly d 5.01, Gly d 5.02, Gly d 7, Gly d 8), *Glycine* spp (Gly f Bd30K, Gly l Bd30K, Gly m 1, Gly m 1.0101, Gly m 1.0102, Gly m 2, Gly m 2.0101, Gly m 2S Albumin, Gly m 3, Gly m 3.0101, Gly m 3.0102, Gly m 39kD, Gly m 4, Gly m 4.0101, Gly m 5, Gly m 5.0101, Gly m 5.0201, Gly m 5.0301, Gly m 5.0302, Gly m 50kD, Gly m 6, Gly m 6.0101, Gly m 6.0201, Gly m 6.0301, Gly m 6.0401, Gly m 6.0501, Gly m 68kD, Gly m Agglutinin, Gly m Bd28K, Gly m Bd30K, Gly m Bd60K, Gly m CPI, Gly m EAP, Gly m TI, Gly mi Bd30K, Gly s Bd30K, Gly t Bd30K, Gly to Bd30K), *Gossypium* spp (Gos h Vicilin), *Haemophilus* spp (Hae in P6), *Haemaphysalis* spp (Hae l 7, Hae l 7.0101, Hae q 7, Hae q 7.0101), *Haliotis* spp (Hal a 1, Hal d 1, Hal di 1, Hal di PM, Hal m 1, Hal m 1.0101, Hal r 1, Hal r 49kD, Hal ru 1), *Harmonia* spp (Har a 1, Har a 1.0101, Har a 2, Har a 2.0101), *Harpegnathos* spp (Har sa 7, Har sa 7.0101, Har sa 7.0102), *Helianthus* spp (Hel a 1, Hel a 1.0101, Hel a 2, Hel a 2.0101, Hel a 2S Albumin, Hel a 3, Hel a 3.0101, Hel a 4), *Helix* spp (Hel ap 1, Hel as 1, Hel as 1.0101), *Heligmosomoides* spp (Hel p 3, Hel p 3.0101), *Helianthus* spp (Hel to 1), Hemanthias spp (Hem le 1), *Hemifusus* spp (Hem t 1), *Heterodera* spp (Het g 3, Het g 3.0101), Hevea spp (Hev b 1, Hev b 1.0101, Hev b 10, Hev b 10.0101, Hev b 10.0102, Hev b 10.0103, Hev b 11, Hev b 11.0101, Hev b 11.0102, Hev b 12, Hev b 12.0101, Hev b 13, Hev b 13.0101, Hev b 14, Hev b 14.0101, Hev b 2, Hev b 2.0101, Hev b 3, Hev b 3.0101, Hev b 4, Hev b 4.0101, Hev b 5, Hev b 5.0101, Hev b 6, Hev b 6.01, Hev b 6.02, Hev b 6.0202, Hev b 6.03, Hev b 7, Hev b 7.01, Hev b 7.02, Hev b 7.D2, Hev b 7.S2, Hev b 8, Hev b 8.0101, Hev b 8.0102, Hev b 8.0201, Hev b 8.0202, Hev b 8.0203, Hev b 8.0204, Hev b 9, Hev b 9.0101, Hev b Citrate binding Protein, Hev b GAPDH, Hev b HSP80, Hev b IFR, Hev b Proteasome subunit, Hev b Rotamase, Hev b SPI, Hev b Trx, Hev b UDPGP), Hexagrammos spp (Hex of 1), *Hippoglossus* spp (Hip h 1), *Hippoglossoides* spp (Hip pl 1), *Hippoglossus* spp (Hip st 1), *Hirudo* spp (Hir me Hirudin), *Holcus* spp (Hol l 1, Hol l 1.0101, Hol l 1.0102, Hol l 2, Hol l 4, Hol l 5, Hol l 5.0101, Hol l 5.0201), *Holocnemus* spp (Hol pl 9, Hol pl Hemocyanin), *Homarus* spp (Horn a 1, Horn a 1.0101, Horn a 1.0102, Horn a 1.0103, Horn a 3, Horn a 3.0101, Horn a 4, Horn a 6, Horn a 6.0101, Horn g 1, Hom g 2), *Homo* spp (Hom s 1, Hom s 1.0101, Hom s 2, Hom s 2.0101, Hom s 3, Hom s 3.0101, Hom s 4, Hom s 4.0101, Hom s 5, Hom s 5.0101, Hom s AAT, Hom s ACTH, Hom s Adalimumab, Hom s ALA, Hom s alpha_Actin, Hom s alpha-Galactosidase, Hom s APDH, Hom s Arylsulfatase B, Hom s Casein, Hom s CyP A, Hom s CyP B, Hom s CyP C, Hom s DSF70, Hom s DSG3, Hom s eIF6, Hom s Etanercept, Hom s Factor IX, Hom s Factor VII, Hom s Factor VIII, Hom s G-CSF, Hom s Glucocerebrosidase, Hom s Glucosidase, Hom s HLA-DR-alpha, Hom s HSA, Hom s Iduronidase, Hom s Idursulfase, Hom s IgA, Hom s Insulin, Hom s Lactoferrin, Hom s Laminin gamma_2, Hom s MnSOD, Hom s Oxytocin, Hom s P2, Hom s Phosvitin, Hom s Profilin, Hom s PSA, Hom s RP1, Hom s TCTP, Hom s TL, Hom s TPA, Hom s TPO, Hom s Transaldolase, Hom s Trx, Hom s Tubulin-alpha, Hom s/Mus m Basiliximab, Hom s/Mus m Cetuximab, Hom s/Mus m Cetuximab (Gal-Gal), Hom s/Mus m Infliximab, Hom s/Mus m Natalizumab, Hom s/Mus m Omalizumab, Hom s/Mus m Palivizumab, Hom s/Mus m Rituximab, Hom s/Mus m Tocilizumab, Hom s/Mus m Trastuzumab), *Hoplostethus* spp (Hop a 1), *Hordeum* spp (Hor v 1, Hor v 12, Hor v 12.0101, Hor v 13, Hor v 14, Hor v 15, Hor v 15.0101, Hor v 16, Hor v 16.0101, Hor v 17, Hor v 17.0101, Hor v 18kD, Hor v 2, Hor v 21, Hor v 21.0101, Hor v 28, Hor v 33, Hor v 4, Hor v 5, Hor v 5.0101, Hor v BDAI, Hor v BTI), *Humicola* spp (Hum in Cellulase), *Humulus* spp (Hum j 1, Hum j 1.0101, Hum j 10kD, Hum j 2), *Huso* spp (Hus h 1), *Hylocereus* spp (Hyl un LTP), *Hymenocephalus* spp (Hym st 1), *Hyperoglyphe* spp (Hyp by 1), *Hypophthalmichthys* spp (Hyp mo 1), *Hypophthalmichthy* spp (Hyp no 1), Ictalurus spp (Ict fu 1, Ict p 1), *Imperata* spp (Imp c 4, Imp c 5, Imp c Mel), *Ixodes* spp (Ixo r 2, Ixo sc 7, Ixo sc 7.0101), *Jasus* spp (Jas Ia 1, Jas Ia 1.0101, Jas Ia 1.0102), *Juglans* spp (Jug ca 1, Jug ca 2, Jug ci 1, Jug ci 2, Jug n 1, Jug n 1.0101, Jug n 2, Jug n 2.0101, Jug r 1, Jug r 1.0101, Jug r 2, Jug r 2.0101, Jug r 3, Jug r 3.0101, Jug r 4, Jug r 4.0101, Jug r 5), *Juniperus* spp (Jun a 1, Jun a 1.0101, Jun a 1.0102, Jun a 2, Jun a 2.0101, Jun a 3, Jun a 3.0101, Jun c 1, Jun o 1, Jun o 4, Jun o 4.0101, Jun r 3, Jun r 3.1, Jun r 3.2, Jun v 1, Jun v 1.0101, Jun v 1.0102, Jun v 3, Jun v 3.0101, Jun v 3.0102, Jun v 4), *Katsuwonus* spp (Kat p 1), *Kyphosus* spp (Kyp se 1), *Lachnolaimus* spp (Lac ma 1), *Lachesis* spp (Lac mu 1), *Lactuca* spp (Lac s 1, Lac s 1.0101), *Lagocephalus* spp (Lag la 1), *Larus* spp (Lar a 1, Lar a 2, Lar a 3), *Larimichthys* spp (Lar po 1), *Lates* spp (Lat c 1), *Lateolabrax* spp (Lat ja 1), *Lathyrus* spp (Lat oc Agglutinin), *Leiostomus* spp (Lei xa 1), *Lens* spp (Len c 1, Len c 1.0101, Len c 1.0102, Len c 1.0103, Len c 2, Len c 2.0101, Len c 3, Len c 3.0101, Len c Agglutinin), *Leopardus* spp (Leo p 1), *Lepidoglyphus* spp (Lep d 10, Lep d 10.0101, Lep d 12, Lep d 13, Lep d 13.0101, Lep d 2, Lep d 2.0101, Lep d 2.0102, Lep d 2.0201, Lep d 2.0202, Lep d 3, Lep d 39kD, Lep d 5, Lep d 5.0101, Lep d 5.0102, Lep d 5.0103, Lep d 7, Lep d 7.0101, Lep d 8, Lep d alpha Tubulin), *Lepomis* spp (Lep gi 1), *Leptomelanosoma* spp (Lep i 1), *Lepomis* spp (Lep ma 1), *Lepisma* spp (Lep s 1, Lep s 1.0101, Lep s 1.0102), *Lepeophtheirus* spp (Lep sa 1, Lep sa 1.0101, Lep sa 1.0102, Lep sa 1.0103), *Leptailurus* spp (Lep se 1), *Lepidorhombus* spp (Lep w 1, Lep w 1.0101), *Lethocerus* spp (Let in 7, Let in 7.0101, Let in 7.0102), Leuciscus spp (Leu ce 1), *Lewia* spp (Lew in 1), *Ligustrum* spp (Lig v 1, Lig v 1.0101, Lig v 1.0102, Lig v 2), *Lilium* spp (Lil l 2, Lil l PG), *Limanda* spp (Lim fe 1), *Limnonectes* spp (Lim m 1), *Limulus* spp (Lim p 1, Lim p 1.0101, Lim p 2, Lim p LPA), *Liposcelis* spp (Lip b 1, Lip b 1.0101), *Litchi* spp (Lit c 1, Lit c 1.0101, Lit c IFR, Lit c TPI), *Lithobates* spp (Lit ca 1), Litopenaeus spp (Lit se 1, Lit v 1, Lit v 1.0101, Lit v 2, Lit v 2.0101, Lit v 3, Lit v 3.0101, Lit v 4, Lit v 4.0101), *Filiaria* spp (*Loa* lo 3, *Loa* lo 3.0101), *Lobotes* spp (Lob su 1), *Locusta* spp (Loc m 7, Loc m 7.0101), *Loligo* spp (Lol b 1, Lol e 1), *Lolium* spp (Lol m 2, Lol m 5, Lol p 1, Lot p 1.0101, Lol p 1.0102, Lol p 1.0103, Lol p 10, Lol p 11, Lol p 11.0101, Lol p 12, Lol p 13, Lol p 2, Lol p 2.0101, Lot p 3, Lol p 3.0101, Lol p 4, Lol p 4.0101, Lot p 5, Lot p 5.0101, Lol p 5.0102, Lol p 7, Lol p CyP, Lol p FT, Lol p Legumin), *Lonomia* spp (Lon o 7, Lon o 7.0101), *Lophodytes* spp (Lop cu 1), *Lophonetta* spp (Lop sp 1), *Lupinus* spp (Lup a 1, Lup a atpha_Congtutin, Lup a delta_Conglutin, Lup a gamma_Congtutin, Lup an 1, Lup an 1.0101, Lup an alpha_Conglutin, Lup an delta_Conglutin, Lup an gamma_Congtutin, Lup l 17kD), *Lutjanus* spp (Lut a 1, Lut c 1, Lut cy 1, Lut gr 1, Lut gu 1, Lut jo 1), *Lutraria* spp (Lut p 1), *Lutjanus* spp (Lut pu 1, Lut sy 1), *Lycopersicon* spp (Lyc e 1, Lyc e 1.0101, Lyc e 11S Globulin, Lyc e 2, Lyc e 2.0101, Lyc e 2.0102, Lyc e 3, Lyc e 3.0101, Lyc e 4, Lyc e 4.0101, Lyc e ARP60S, Lyc e Chitinase, Lyc e Glucanase, Lyc e Peroxidase, Lyc e PG, Lyc e PME, Lyc e PR23, Lyc e Vicilin), *Maconellicoccus* spp (Mac h 7, Mac h 7.0101), Macruronus spp (Mac ma 1, Mac n 1), *Maclura* spp (Mac po 17kD), Macrobrachium spp (Mac ro 1, Mac ro 1.0101, Mac ro Hemocyanin), *Macropus* spp (Macy s Gelatin), *Malus* spp (Mal d 1, Mal d 1.0101, Mal d 1.0102, Mal d 1.0103, Mal d 1.0104, Mal d 1.0105, Mal d 1.0106, Mal d 1.0107, Mal d 1.0108, Mal d 1.0109, Mal d 1.0201, Mal d 1.0202, Mal d 1.0203, Mal d 1.0204, Mal d 1.0205, Mal d 1.0206, Mal d 1.0207, Mal d 1.0208, Mal d 1.0301, Mal d 1.0302, Mal d 1.0303, Mal d 1.0304, Mal d 1.0401, Mal d 1.0402, Mal d 1.0403, Mal d 2, Mal d 2.0101, Mal d 3, Mal d 3.0101, Mal d 3.0102, Mal d 3.0201, Mal d 3.0202, Mal d 3.0203, Mal d 4, Mal d 4.0101, Mal d 4.0102, Mal d 4.0201, Mal d 4.0202, Mal d 4.0301, Mal d 4.0302), *Malpighia* spp (Mal g 4, Mal g Hevein), *Malus* spp (Mal p 1), *Malassezia* spp (*Mala* f 2, *Mala* f 2.0101, *Mala* f 3, *Mala* f 3.0101, *Mala* f 4, *Mala* f 4.0101, *Mala* g 10, *Mala* s 1, *Mala* s 1.0101, *Mala* s 10, *Mala* s 10.0101, *Mala* s 11, *Mala* s 11.0101, *Mala* s 12, *Mala* s 12.0101, *Mala* s 13, *Mala* s 13.0101, *Mala* s 5, *Mala* s 5.0101, *Mala* s 6, *Mala* s 6.0101, *Mala* s 7, *Mala* s 7.0101, *Mala* s 8, *Mala* s 8.0101, *Mala* s 9, *Mala* s 9.0101), *Manihot* spp (Man e 5, Man e 5.0101, Man e FPA, Man e GAPDH), *Mangifera* spp (Man i 1, Man i 14kD, Man i 2, Man i 3, Man i 3.01, Man i 3.02, Man i Chitinase), Marsupenaeus spp (Mar j 1, Mar j 1.0101, Mar j 2, Mar j 4), *Matricaria* spp (Mat c 17kD), *Mecopoda* spp (Mec e 7), *Megalobrama* spp (Meg am 2, Meg am CK), *Megathura* spp (Meg c Hemocyanin), *Megalops* spp (Meg sp 1), *Melanogrammus* spp (Mel a 1), *Meleagris* spp (Mel g 1, Mel g 2, Mel g 3, Mel g PRVB, Mel g TSA), *Melicertus* spp (Mel 11), *Menticirrhus* spp (Men am 1), *Mercurialis* spp (Mer a 1, Mer a 1.0101), *Merluccius* spp (Mer ap 1, Mer au 1, Mer bi 1, Mer ca 1, Mer ga 1, Mer hu 1), *Merlangius* spp (Mer me 1), *Merluccius* spp (Mer mr 1, Mer pa 1, Mer po 1, Mer pr 1, Mer se 1), *Meriones* spp (Mer un 23kD), *Metarhizium* spp (Met a 30), *Metapenaeopsis* spp (Met ba 1), *Metapenaeus* spp (Met e 1, Met e 1.0101, Met e 2), *Metasequoia* spp (Met gl 2), *Metapenaeus* spp (Met j 1, Met j 2), *Metanephrops* spp (Met ja 1), *Metapenaeopsis* spp (Met la 1), *Metanephrops* spp (Met t 2), *Micromesistius* spp (Mic po 1), *Micropogonias* spp (Mic un 1), *Mimachlamys* spp (Mim n 1), *Momordica* spp (Mom c RIP), *Morus* spp (Mor a 17kD, Mor a 4), *Morone* spp (Mor am 1), *Morus* spp (Mor n 3, Mor n 3.0101), *Morone* spp (Mor sa 1, Mor sc 1), *Mugil* spp (Mug c 1), *Muraenolepis* spp (Mur mi 1), *Musa* spp (Mus a 1, Mus a 1.0101, Mus a 2, Mus a 2.0101, Mus a 3, Mus a 3.0101, Mus a 4, Mus a 4.0101, Mus a 5, Mus a 5.0101, Mus a 5.0102), *Mus* spp (Mus m 1, Mus m 1.0101, Mus m 1.0102, Mus m 2, Mus m Gelatin, Mus m IgG, Mus m MSA, Mus m Muromonab, Mus m Phosvitin), *Mustela* spp (Mus p 17kD), *Musa* spp (Mus xp 1, Mus xp 2, Mus xp 5), *Mycteroperca* spp (Myc bo 1, Myc mi 1, Myc ph 1), *Myceliophthora* spp (Myc sp Laccase), *Myrmecia* spp (Myr p 1, Myr p 1.0101, Myr p 2, Myr p 2.0101, Myr p 2.0102, Myr p 3, Myr p 3.0101), *Mytilus* spp (Myt e 1, Myt g 1, Myt g PM), *Myzus* spp (Myz p 7, Myz p 7.0101), *Nemorhedus* spp (Nae go Hya), *Necator* spp (Nec a Calreticulin), *Nemipterus* spp (Nem vi 1), *Neosartorya* spp (Neo fi 1, Neo fi 22), *Neochen* spp (Neo ju 1), Neoscona spp (Neo n 7, Neo n 7.0101), *Nephelium* spp (Nep I GAPDH), Nephrops spp (Nep n 1, Nep n DF9), *Neptunea* spp (Nep po 1, Nep po 1.0101), *Nicotiana* spp (Nic t 8, Nic t Osmotin, Nic t Villin), *Nimbya* spp (Nim c 1, Nim s 1), *Nippostrongylus* spp (Nip b Ag1), *Nycticebus* spp (Nyc c 1), *Octopus* spp (Oct f 1, Oct l 1, Oct v 1, Oct v 1.0101, Oct v PM), *Ocyurus* spp (Ocy ch 1), *Olea* spp (Ole e 1, Ole e 1.0101, Ole e 1.0102, Ole e 1.0103, Ole e 1.0104, Ole e 1.0105, Ole e 1.0106, Ole e 1.0107, Ole e 10, Ole e 10.0101, Ole e 11, Ole e 11.0101, Ole e 11.0102, Ole e 12, Ole e 13, Ole e 2, Ole e 2.0101, Ole e 3, Ole e 3.0101, Ole e 36kD, Ole e 4, Ole e 4.0101, Ole e 5, Ole e 5.0101, Ole e 6, Ole e 6.0101, Ole e 7, Ole e 7.0101, Ole e 8, Ole e 8.0101, Ole e 9, Ole e 9.0101), *Ommastrephes* spp (Omm b 1, Omm b 1.0101), *Oncorhynchus* spp (Onc ke 1, Onc ke 18 kD, Onc ke alpha2l, Onc ke Vitellogenin, Onc m 1, Onc m 1.0101, Onc m 1.0201, Onc m alpha2l, Onc m Protamine, Onc m Vitellogenin, Onc ma 1, Onc ma FPA, Onc ma FSA, Onc ma TPI, Onc n 1), *Onchocerca* spp (Onc o 3, Onc o 3.0101), *Oncorhynchus* spp (Onc is 1), *Onchocerca* spp (Onc v 3, Onc v 3.0101), *Oratosquilla* spp (Ora o 1, Ora o 1.0101), *Oreochromis* spp (Ore a 1, Ore mo 1, Ore mo 2, Ore mo FPA, Ore mo SCAF7145, Ore ni 1, Ore ni 18kD, Ore ni 45kD), *Ornithonyssus* spp (Orn sy 10, Orn sy 10.0101, Orn sy 10.0102), *Oryctolagus* spp (Ory c 1, Ory c 1.0101, Ory c 2, Ory c Casein, Ory c Phosvitin, Ory c RSA), *Oryza* spp (Ory s 1, Ory s 1.0101, Ory s 11, Ory s 12, Ory s 12.0101, Ory s 13, Ory s 14, Ory s 17kD, Ory s 19kD, Ory s 2, Ory s 23, Ory s 3, Ory s 7, Ory s aA_TI, Ory s GLP52, Ory s GLP63, Ory s Glyoxalase I, Ory s NRA), *Ostrya* spp (Ost c 1, Ost c 1.0101), *Ovis* spp (Ovi a ALA, Ovi a BLG, Ovi a Casein, Ovi a Casein alphaS1, Ovi a Casein alphaS2, Ovi a Casein beta, Ovi a Casein kappa, Ovi a Phosvitin, Ovi a SSA), Pachycondyla spp (Pac c 3), *Pagrus* spp (Pag m 1, Pag pa 1), *Pampus* spp (Pam ar 1, Pam c 1), *Pandalus* spp (Pan b 1, Pan b 1.0101), *Pangasius* spp (Pan bo 1), *Pandalus* spp (Pan e 1, Pan e 1.0101, Pan e 4), *Panulirus* spp (Pan h 1, Pan hy 1), *Pangasius* spp (Pan hy 18kD, Pan hy 45kD), *Panulirus* spp (Pan j 1), *Panthera* spp (Pan 11, Pan o 1, Pan p 1), *Panulirus* spp (Pan s 1, Pan s 1.0101), *Panthera* spp (Pan t 1), *Pan* spp (Pan tr TCTP), *Papaver* spp (Pap s 17kD, Pap s 2, Pap s 34kD), *Papilio* spp (Pap xu 7, Pap xu 7.0101, Pap xu 7.0102), *Paralichthys* spp (Par a 1), *Parasilurus* spp (Par as 1, Par c 1), *Paralithodes* spp (Par c 1.0101, Par c 1.0102, Par f 1), *Parthenium* spp (Par h 1), *Parietaria* spp (Par j 1, Par j 1.0101, Par j 1.0102, Par j 1.0103, Par j 1.0201, Par j 2, Par j 2.0101, Par j 2.0102, Par j 3, Par j 3.0101, Par j 3.0102, Par j 4, Par j 4.0101, Par j J1-J2), *Paralichthys* spp (Par le 1), *Parietaria* spp (Par m 1, Par o 1, Par o 1.0101), *Paralichthys* spp (Par of 1, Par of alpha21), *Parahucho* spp (Par pe Vitellogenin), *Passiflora* spp (Pas e Chitinase, Pas e Hevein), *Paspalum* spp (Pas n 1, Pas n 1.0101, Pas n 13), *Patinopecten* spp (Pat y 1), *Pediculus* spp (Ped h 7, Ped h 7.0101), *Penaeus* spp (Pen a 1, Pen a 1.0101, Pen a 1.0102, Pen a 1.0102 (103-117), Pen a 1.0102 (109-123), Pen a 1.0102 (1-15), Pen a 1.0102 (115-129), Pen a 1.0102 (121-135), Pen a 1.0102 (127-141), Pen a 1.0102 (13-27), Pen a 1.0102 (133-147), Pen a 1.0102 (139-153), Pen a 1.0102 (145-159)), *Farfantepenaeus* spp (Pen a 1.0102 (151-165)), *Penaeus* spp (Pen a 1.0102 (157-171), Pen a 1.0102 (163-177), Pen a 1.0102 (169-183), Pen a 1.0102 (175-189), Pen a 1.0102 (181-195), Pen a 1.0102 (187-201), Pen a 1.0102 (193-207), Pen a 1.0102 (19-33), Pen a 1.0102 (199-213), Pen a 1.0102 (205-219), Pen a 1.0102 (211-225), Pen a 1.0102 (217-231), Pen a 1.0102 (223-237), Pen a 1.0102 (229-243)), *Farfantepenaeus* spp (Pen a 1.0102 (235-249)), *Penaeus* spp (Pen a 1.0102 (241-255), Pen a 1.0102 (247-261), Pen a 1.0102 (253-267), Pen a 1.0102 (25-39), Pen a 1.0102 (259-273), Pen a 1.0102 (265-279), Pen a 1.0102 (270-284), Pen a 1.0102 (31-45), Pen a 1.0102 (37-51), Pen a 1.0102 (43-57), Pen a 1.0102 (49-63)), *Farfantepenaeus* spp (Pen a 1.0102 (55-69)), *Penaeus* spp (Pen a 1.0102 (61-75), Pen a 1.0102 (67-81), Pen a 1.0102 (7-21), Pen a 1.0102 (73-87), Pen a 1.0102 (79-93), Pen a 1.0102 (85-99), Pen a 1.0102 (91-105), Pen a 1.0102 (97-111), Pen a 1.0103), *Penicillium* spp (Pen b 13, Pen b 13.0101, Pen b 26, Pen b 26.0101, Pen c 1, Pen c 13, Pen c 13.0101, Pen c 18, Pen c 19, Pen c 19.0101, Pen c 2, Pen c 22, Pen c 22.0101, Pen c 24, Pen c 24.0101, Pen c 3, Pen c 3.0101, Pen c 30, Pen c 30.0101, Pen c 32, Pen c 32.0101, Pen c MnSOD, Pen ch 13, Pen ch 13.0101, Pen ch 18, Pen ch 18.0101, Pen ch 20, Pen ch 20.0101, Pen ch 31, Pen ch 31.0101, Pen ch 33, Pen ch 33.0101, Pen ch 35, Pen ch 35.0101, Pen ch MnSOD), *Penaeus* spp (Pen i 1, Pen i 1.0101, Pen m 1, Pen m 1.0101, Pen m 1.0102, Pen m 2, Pen m 2.0101, Pen m 3, Pen m 3.0101, Pen m 4, Pen m 4.0101, Pen m 6, Pen m 6.0101), *Penicillium* spp (Pen o 18, Pen o 18.0101), *Penaeus* spp (Pena o 1, Pena o 1.0101), *Periplaneta* spp (Per a 1, Per a 1.0101, Per a 1.0102, Per a 1.0103, Per a 1.0104, Per a 1.0105, Per a 1.0201, Per a 10, Per a 10.0101, Per a 2, Per a 3, Per a 3.0101, Per a 3.0201, Per a 3.0202, Per a 3.0203, Per a 4, Per a 5, Per a 6, Per a 6.0101, Per a 7, Per a 7.0101, Per a 7.0102, Per a 7.0103, Per a 9, Per a 9.0101, Per a Cathepsin, Per a FABP, Per a Trypsin, Per f 1, Per f 7, Per f 7.0101), *Perna* spp (Per v 1), *Persea* spp (Pers a 1, Pers a 1.0101, Pers a 4), *Petroselinum* spp (Pet c 1, Pet c 2, Pet c 3), *Phalaris* spp (Pha a 1, Pha a 1.0101, Pha a 5, Pha a 5.0101, Pha a 5.02, Pha a 5.03, Pha a 5.04), *Phaseolus* spp (Pha v 3, Pha v 3.0101, Pha v 3.0201, Pha v aAI, Pha v aAI.0101, Pha v Chitinase, Pha v PHA, Pha v Phaseolin), *Phleum* spp (Phl p 1, Phl p 1.0101, Phl p 1.0102, Phl p 11, Phl p 11.0101, Phl p 12, Phl p 12.0101, Phl p 12.0102, Phl p 12.0103, Phl p 13, Phi p 13.0101, Phi p 2, Phi p 2.0101, Phi p 3, Phi p 3.0101, Phi p 3.0102, Phl p 4, Phl p 4.0101, Phl p 4.0102, Phl p 4.0201, Phl p 4.0202, Phl p 4.0203, Phl p 4.0204, Phl p 5, Phl p 5.0101, Phl p 5.0102, Phl p 5.0103, Phl p 5.0104, Phl p 5.0105, Phl p 5.0106, Phl p 5.0107, Phl p 5.0108, Phl p 5.0109, Phl p 5.0201, Phl p 5.0202, Phl p 5.0203, Phl p 5.0204, Phl p 5.0205, Phl p 5.0206, Phl p 5.0207, Phl p 6, Phl p 6.0101, Phl p 6.0102, Phl p 7, Phl p 7.0101, Phl p P1-P2-P5-P6, Phl p P2-P6, Phl p P5-P1, Phl p P6-P2), Phoenix spp (Pho d 2, Pho d 2.0101, Pho d 40kD, Pho d 90kD), *Phodopus* spp (Pho s 21kD), *Phoma* spp (Pho t 1), *Phragmites* spp (Phr a 1, Phr a 12, Phr a 13, Phr a 4, Phr a 5), *Phytolacca* spp (Phy a RIP), *Pimpinella* spp (Pim a 1, Pim a 2), *Pinna* spp (Pin a 1), Piper spp (Pip n 14kD, Pip n 28kD), *Pisum* spp (Pis s 1, Pis s 1.0101, Pis s 1.0102, Pis s 2, Pis s 2.0101, Pis s 5, Pis s Agglutinin, Pis s Albumin), *Pistacia* spp (Pis v 1, Pis v 1.0101, Pis v 2, Pis v 2.0101, Pis v 2.0201, Pis v 3, Pis v 3.0101, Pis v 4, Pis v 4.0101, Pis v 5, Pis v 5.0101), *Platanus* spp (Pla a 1, Pla a 1.0101, Pla a 2, Pla a 2.0101, Pla a 3, Pla a 3.0101, Pla a 8), Platichthys spp (Pla f 1), *Plantago* spp (Pla l 1, Pla l 1.0101, Pla l 1.0102, Pla l 1.0103, Pla l Cytochrome C), *Platanus* spp (Pla oc 1, Pla or 1, Pla or 1.0101, Pla or 2, Pla or 2.0101, Pla or 3, Pla or 3.0101, Pla or 4, Pla or CyP, Pla r 1), *Plectropomus* spp (Ple ar 1), Pleospora spp (Ple h 1), *Plectropomus* spp (Ple le 1), *Plodia* spp (Plo i 1, Plo i 1.0101, Plo i 2, Plo i 2.0101), *Poa* spp (Poa p 1, *Poa p 1.0101*, Poa p 10, *Poa p 12*, *Poa p 13*, *Poa p 2*, *Poa p 4*, *Poa p 5*, *Poa p 5.0101*, *Poa p 6*, *Poa p 7*), *Polistes* spp (Pol a 1, Pol a 1.0101, Pol a 2, Pol a 2.0101, Pol a 5, Pot a 5.0101, Pol d 1, Pot d 1.0101, Pot d 1.0102, Pot d 1.0103, Pot d 1.0104, Pol d 4, Pol d 4.0101, Pol d 5, Pol d 5.0101, Pol e 1, Pol e 1.0101, Pol e 2, Pol e 4, Pol e 4.0101, Pol e 5, Pol e 5.0101, Pol f 5, Pol f 5.0101, Pol g 1, Pol g 1.0101, Pol g 2, Pol g 4, Pol g 5, Pol g 5.0101, Pol he MLT, Pol m 5, Pol m 5.0101), *Polypedilum* spp (Pol n 1), *Pollicipes* spp (Pol po 1), *Pollachius* spp (Pol vi 1), *Polybia* spp (Poly p 1, Poly p 1.0101, Poly p 2, Poly p 5, Poly s 5, Poly s 5.0101), *Pomatomus* spp (Porn sa 1), *Pongo* spp (Pon ab HSA), *Pontastacus* spp (Pon I 4, Pon I 4.0101, Pon 17, Pon I 7.0101), *Portunus* spp (Por s 1, Por s 1.0101, Por s 1.0102, Por tr 1, Por tr 1.0101), *Protortonia* spp (Pro ca 38kD), Procumbarus spp (Pro cl 1, Pro cl 1.0101, Pro cl 21kD), *Prosopis* spp (Pro j 20kD), *Prunus* spp (Pru ar 1, Pru ar 1.0101, Pru ar 3, Pru ar 3.0101, Pru av 1, Pru av 1.0101, Pru av 1.0201, Pru av 1.0202, Pru av 1.0203, Pru av 2, Pru av 2.0101, Pru av 3, Pru av 3.0101, Pru av 4, Pru av 4.0101, Pru c 1, Pru d 1, Pru d 2, Pru d 3, Pru d 3.0101, Pru d 4, Pru du 1, Pru du 2, Pru du 2S Albumin, Pru du 3, Pru du 3.0101, Pru du 4, Pru du 4.0101, Pru du 4.0102, Pru du 5, Pru du 5.0101, Pru du 6, Pru du 6.0101, Pru du 6.0201, Pru du Conglutin, Pru p 1, Pru p 1.0101, Pru p 2, Pru p 2.0101, Pru p 2.0201, Pru p 2.0301, Pru p 3, Pru p 3.0101, Pru p 3.0102, Pru p 4, Pru p 4.0101, Pru p 4.0201, Pru sa 3), Psilocybe spp (Psi c 1, Psi c 1.0101, Psi c 2, Psi c 2.0101), *Psoroptes* spp (Pso o 1, Pso o 10, Pso o 10.0101, Pso o 11, Pso o 13, Pso o 14, Pso o 2, Pso o 21, Pso o 3, Pso o 5, Pso o 7), Puma spp (Pum c 1), *Punica* spp (Pun g 3), *Pyrus* spp (Pyr c 1, Pyr c 1.0101, Pyr c 3, Pyr c 3.0101, Pyr c 4, Pyr c 4.0101, Pyr c 5, Pyr c 5.0101, Pyr py 2), *Quercus* spp (Que a 1, Que a 1.0101, Que a 1.0201, Que a 1.0301, Que a 1.0401, Que a 2, Que a 4), *Rachycentron* spp (Rac ca 1), *Rana* spp (Ran e 1, Ran e 1.0101, Ran e 2, Ran e 2.0101), *Ranina* spp (Ran ra 1), *Rangifer* spp (Ran t BLG), *Rattus* spp (Rat n 1, Rat n 1.0101, Rat n Casein, Rat n Gelatin, Rat n IgG, Rat n Phosvitin, Rat n RSA, Rat n Transferrin), *Rhizomucor* spp (Rhi m AP), *Rhizopus* spp (Rhi nv Lipase, Rhi o Lipase), *Rhomboplites* spp (Rho au 1), *Rhodotorula* spp (Rho m 1, Rho m 1.0101, Rho m 2, Rho m 2.0101), *Ricinus* spp (Ric c 1, Ric c 1.0101, Ric c 2, Ric c 3, Ric c 8, Ric c RIP), *Rivulus* spp (Riv ma 1), *Robinia* spp (Rob p 2, Rob p 4, Rob p Glucanase), *Rosa* spp (Ros r 3), *Roystonea* spp (Roy e 2), *Rubus* spp (Rub i 1, Rub i 1.0101, Rub i 3, Rub i 3.0101, Rub i Chitinase, Rub i CyP), *Saccharomyces* spp (Sac c Carboxypeptidase Y, Sac c CyP, Sac c *Enolase*, Sac c Glucosidase, Sac c Invertase, Sac c MnSOD, Sac c P2, Sac c Profilin), *Salvelinus* spp (Sal f 1), *Salsola* spp (Sal k 1, Sal k 1.0101, Sal k 1.0201, Sal k 1.0301, Sal k 1.0302, Sal k 2, Sal k 2.0101, Sal k 3, Sal k 3.0101, Sal k 4, Sal k 4.0101, Sal k 4.0201, Sal k 5, Sal k 5.0101), *Salvelinus* spp (Sal le Vitellogenin), Salmo spp (Sal s 1, Sal s 1.0101, Sal s 1.0201, Sal s 2, Sal s 2.0101, Sal s Gelatin), *Sambucus* spp (Sam n 1), *Sander* spp (San lu 1), *Saponaria* spp (Sap o RIP), *Sardinops* spp (Sar m 1), *Sarkidiornis* spp (Sar ml 1), *Sardina* spp (Sar p 1), *Sarcoptes* spp (Sar s 1, Sar s 14, Sar s 3, Sar s GST, Sar s PM), *Sardinops* spp (Sar sa 1, Sar sa 1.0101), *Schistosoma* spp (Sch j GST, Sch j PM, Sch j Sj22, Sch j Sj67, Sch ma Sm20, Sch ma Sm21, Sch ma Sm22, Sch ma Sm31), *Sciaenops* spp (Sci oc 1), *Scomber* spp (Sco a 1), *Scombermorus* spp (Sco ca 1), *Scomberomorus* spp (Sco g 1), *Scomber* spp (Sco j 1, Sco ma 1, Sco s 1), *Scolopendra* spp (Sco y 7, Sco y 7.0101), *Scylla* spp (Scy o 1, Scy o 1.0101, Scy o 2, Scy pa 1, Scy pa 2, Scy s 1, Scy s 1.0101, Scy s 2), *Sebastes* spp (Seb fa 1, Seb in 1, Seb m 1, Seb m 1.0101, Seb m 1.0201), *Secale* spp (Sec c 1, Sec c 12, Sec c 13, Sec c 2, Sec c 20, Sec c 20.0101, Sec c 20.0201, Sec c 28, Sec c 3, Sec c 4, Sec c 4.0101, Sec c 4.0201, Sec c 5, Sec c 5.0101, Sec c aA_TI, Sec c aA_TI.0101), *Senecio* spp (Sen j MDH, Sen j PL), *Sepia* spp (Sep e 1, Sep e 1.0101), *Sepioteuthis* spp (Sep l 1, Sep l 1.0101), *Sepia* spp (Sep m 1), *Seriola* spp (Ser d 1, Ser la 1), *Sergestes* spp (Ser lu 1), *Seriola* spp (Ser q 1, Ser ri 1), *Sesamum* spp (Ses i 1, Ses i 1.0101, Ses i 2, Ses i 2.0101, Ses i 3, Ses i 3.0101, Ses i 4, Ses i 4.0101, Ses i 5, Ses i 5.0101, Ses i 6, Ses i 6.0101, Ses i 7, Ses i 7.0101, Ses i 8), *Shigella* spp (Shi bo GST, Shi dy GST), *Simulia* spp (Sim vi 1, Sim vi 2, Sim vi 3, Sim vi 4, Sim vi 70kD), *Sinapis* spp (Sin a 1, Sin a 1.0101, Sin a 1.0104, Sin a 1.0105, Sin a 1.0106, Sin a 1.0107, Sin a 1.0108, Sin a 2, Sin a 2.0101, Sin a 3, Sin a 3.0101, Sin a 4, Sin a 4.0101), *Sinonovacula* spp (Sin c 1, Sin c 1.0101), *Solenopsis* spp (Sol g 2, Sol g 2.0101, Sol g 3, Sol g 3.0101, Sol g 4, Sol g 4.0101, Sol g 4.0201, Sol i 1, Sol i 1.0101, Sol i 2, Sol i 2.0101, Sol i 3, Sol i 3.0101, Sol i 4, Sol i 4.0101), *Solenocera* spp (Sol me 1), *Solenopsis* spp (Sol r 1, Sol r 2, Sol r 2.0101, Sol r 3, Sol r 3.0101, Sol s 2, Sol s 2.0101, Sol s 3, Sol s 3.0101, Sol s 4), *Solea* spp (Sol so 1, Sol so TPI), *Solanum* spp (Sola t 1, Sola t 1.0101, Sola t 2, Sola t 2.0101, Sola t 3, Sola t 3.0101, Sola t 3.0102, Sola t 4, Sola t 4.0101, Sola t 8, Sola t Glucanase), *Sorghum* spp (Sor b 1, Sor h 1, Sor h 1.0101, Sor h 12, Sor h 7), *Sparus* spp (Spa a 1), *Sphyrna* spp (Sph ti 1), Spirulina spp (Spi mx beta_Phycocyanin), *Spinacia* spp (Spi o 2, Spi o RuBisCO), *Squilla* spp (Squ ac 1, Squ ac 1.0101, Squ o 1, Squ o 1.0101), *Staphylococcus* spp (Sta a FBP, Sta a SEA, Sta a SEB, Sta a SEC, Sta a SED, Sta a SEE, Sta a TSST), *Stachybotrys* spp (Sta c 3, Sta c 3.0101, Sta c Cellulase, Sta c Hemolysin, Sta c SchS34, Sta c Stachyrase A), *Stemphylium* spp (Ste b 1, Ste c 1, Ste v 1), *Stolephorus* spp (Sto i 1), *Struthio* spp (Str c 1, Str c 2, Str c 3), *Streptococcus* spp (Str dy Streptokinase),

*Streptomyces* spp (Str g Pronase), *Streptococcus* spp (Str pn PspC), *Strongylocentrotus* spp (Str pu 18kD, Str pu Vitellogenin), *Streptococcus* spp (Str py SPEA, Str py SPEC, Str py Streptokinase), *Strongyloides* spp (Str st 45kD), *Streptomyces* spp (Str v PAT), *Styela* spp (Sty p 1), *Suidasia* spp (Sui m 1, Sui m 13, Sui m 2, Sui m 3, Sui m 5, Sui m 5.01, Sui m 5.02, Sui m 5.03, Sui m 6, Sui m 7, Sui m 8, Sui m 9), *Sus* spp (Sus s ACTH, Sus s ALA, Sus s Amylase, Sus s BLG, Sus s Casein, Sus s Casein alphaS1, Sus s Casein alphaS2, Sus s Casein beta, Sus s Casein kappa, Sus s Gelatin, Sus s HG, Sus s Insulin, Sus s Lipase, Sus s Pepsin, Sus s Phosvitin, Sus s PRVB, Sus s PSA, Sus s TCTP), *Syntelopodeuma* spp (Syn y 7, Syn y 7.0101), *Syringa* spp (Syr v 1, Syr v 1.0101, Syr v 1.0102, Syr v 1.0103, Syr v 2, Syr v 3, Syr v 3.0101), *Tabanus* spp (Tab y 1, Tab y 1.0101, Tab y 2, Tab y 2.0101, Tab y 5, Tab y 5.0101), *Tadorna* spp (Tad ra 1), *Talaromyces* spp (Tal st 22, Tal st 3, Tal st 8), *Taraxacum* spp (Tar o 18kD), *Taxodium* spp (Tax d 2), *Tegenaria* spp (Teg d Hemocyanin), *Teladorsagia* spp (Tel ci 3), *Thaumetopoea* spp (Tha p 1, Tha p 1.0101, Tha p 2, Tha p 2.0101), *Theragra* spp (The c 1), *Thermomyces* spp (The I Lipase, The sp Lipase, The sp Xylanase), *Thunnus* spp (Thu a 1, Thu a 1.0101, Thu a Collagen, Thu al 1, Thu at 1, Thu o 1, Thu o Collagen), *Thuja* spp (Thu oc 3, Thu p 1), *Thunnus* spp (Thu t 1, Thu to 1), *Thyrsites* spp (Thy at 1), *Thyrophygus* spp (Thy y 7, Thy y 7.0101), *Todarodes* spp (Tod p 1, Tod p 1.0101, Tod p 1.0102), *Toxoptera* spp (Tox c 7, Tox c 7.0101), *Toxocara* spp (Tox ca TES120, Tox ca TES26, Tox ca TES30), *Toxoplasma* spp (Tox g HSP70), *Trachypenaeus* spp (Tra c 1), *Trachinotus* spp (Tra ca 1), *Trachurus* spp (Tra j 1, Tra j Gelatin, Tra tr Gelatin), *Triticum* spp (Tri a 1, Tri a 10kD, Tri a 12, Tri a 12.0101, Tri a 12.0102, Tri a 12.0103, Tri a 12.0104, Tri a 13, Tri a 14, Tri a 14.0101, Tri a 14.0201, Tri a 15, Tri a 15.0101, Tri a 18, Tri a 18.0101, Tri a 19, Tri a 19.0101, Tri a 2, In a 21, Tri a 21.0101, Tri a 23kd, Tri a 25, Tri a 25.0101, Tri a 26, Tri a 26.0101, Tri a 27, Tri a 27.0101, Tri a 28, Tri a 28.0101, Tri a 29, Tri a 29.0101, Tri a 29.0201, Tri a 3, Tri a 30, Tri a 30.0101, Tri a 31, Tri a 31.0101, Tri a 32, Tri a 32.0101, Tri a 33, Tri a 33.0101, Tri a 34, Tri a 34.0101, Tri a 35, Tri a 35.0101, Tri a 36, Tri a 36.0101, Tri a 37, Tri a 37.0101, Tri a 4, Tri a 4.0101, Tri a 4.0201, Tri a 5, Tri a 7, Tri a aA_SI, Tri a alpha_Gliadin, Tri a bA, Tri a Bd36K, Tri a beta_Gliadin, Tri a Chitinase, Tri a CM16, Tri a DH, Tri a Endochitinase, Tri a gamma_Gliadin, Tri a Germin, Tri a Gliadin, Tri a GST, Tri a LMW Glu, Tri a LMW-GS B16, Tri a LMW-GS P42, Tri a LMW-GS P73, Tri a LTP2, Tri a omega2_Gliadin, Tri a Peroxidase, Tri a Peroxidase 1, Tri a SPI, Tri a TLP, Tri a Tritin, Tri a XI), *Tritirachium* spp (Tri al Proteinase K), *Tribolium* spp (Tri ca 17, Tri ca 17.0101, Tri ca 7, Tri ca 7.0101), *Trichostrongylus* spp (Tri co 3, Tri co 3.0101), *Trichophyton* spp (Tri eq 4), *Trigonella* spp (Tri fg 1, Tri fg 2, Tri fg 3, Tri fg 4), *Trichosanthes* spp (Tri k RIP), *Trichiurus* spp (Tri le 1), *Triticum* spp (Tri m Peroxidase), *Trichophyton* spp (Tri me 2, Tri me 4), *Trisetum* spp (Tri p 1, Tri p 5), *Trichinella* spp (Tri ps 3, Tri ps 3.0101), *Trichophyton* spp (Tri r 2, Tri r 2.0101, Tri r 4, Tri r 4.0101), *Trichoderma* spp (Tri rs Cellulase), *Triticum* spp (Tri s 14), *Trichophyton* spp (Tri sc 2, Tri sc 4, Tri so 2), *Trichinella* spp (Tri sp 3, Tri sp 3.0101, Tri sp 3.0102, Tri sp 3.0103, Tri sp 3.0104, Tri sp 3.0105, Tri sp 3.0106), *Trichophyton* spp (Tri t 1, Tri t 1.0101, Tri t 4, Tri t 4.0101), *Triticum* spp (Tri td 14, Tri td aA_TI), *Trichoderma* spp (Tri v Cellulase), *Trichophyton* spp (Tri ve 4), *Triatoma* spp (Tria p 1, Tria p 1.0101), *Triplochiton* spp (Trip s 1), *Turbo* spp (Tur c 1, Tur c PM), *Tyrophagus* spp (Tyr p 1, Tyr p 10, Tyr p 10.0101, Tyr p 10.0102, Tyr p 13, Tyr p 13.0101, Tyr p2, Tyr p 2.0101, Tyr p 24, Tyr p 24.0101, Tyr p 3, Tyr p 3.0101, Tyr p 4, Tyr p 5, Tyr p 5.01, Tyr p 5.02, Tyr p 5.03, Tyr p 7, Tyr p alpha Tubulin), *Ulocladium* spp (Ulo a 1, Ulo at 1, Ulo b 1, Ulo c 1, Ulo co 1, Ulo cu 1, Ulo mu 1, Ulo ob 1, Ulo se 1, Ulo su 1, Ulo to 1), *Uncia* spp (Unc u 1), Urophycis spp (Uro to 1), *Vaccinium* spp (Vac m 3), *Varroa* spp (Var j 13kD), Venerupis spp (Ven ph 1, Ven ph 1.0101), *Vespula* spp (Ves f 1, Ves f 2, Ves f 5, Ves f 5.0101, Ves g 1, Ves g 2, Ves g 5, Ves g 5.0101, Ves m 1, Ves m 1.0101, Ves m 2, Ves m 2.0101, Ves m 5, Ves m 5.0101, Ves m MLT, Ves p 1, Ves p 2, Ves p 5, Ves p 5.0101, Ves s 1, Ves s 1.0101, Ves s 2, Ves s 5, Ves s 5.0101, Ves v 1, Ves v 1.0101, Ves v 2, Ves v 2.0101, Ves v 2.0201, Ves v 3, Ves v 3.0101, Ves v 5, Ves v 5.0101, Ves v 5-Pol a 5, Ves vi 5, Ves vi 5.0101), *Vespa* spp (Vesp c 1, Vesp c 1.0101, Vesp c 2, Vesp c 5, Vesp c 5.0101, Vesp c 5.0102, Vesp m 1, Vesp m 1.0101, Vesp m 5, Vesp m 5.0101, Vesp ma 1, Vesp ma 2, Vesp ma 5, Vesp ma MLT, Vesp v MLT), *Vigna* spp (Vig r 1, Vig r 1.0101, Vig r 17kD, Vig r 5, Vig r 8S Globulin, Vig r Albumin, Vig r beta-Conglycinin), *Vitis* spp (Vit v 1, Vit v 1.0101, Vit v 4, Vit v 5, Vit v Glucanase, Vit v TLP), *Xiphias* spp (Xip g 1, Xip g 1.0101, Xip g 25kD), *Zea* spp (Zea m 1, Zea m 1.0101, Zea m 11, Zea m 12, Zea m 12.0101, Zea m 12.0102, Zea m 12.0103, Zea m 12.0104, Zea m 12.0105, Zea m 13, Zea m 14, Zea m 14.0101, Zea m 14.0102, Zea m 2, Zea m 20S, Zea m 22, Zea m 25, Zea m 25.0101, Zea m 27kD Zein, Zea m 3, Zea m 4, Zea m 5, Zea m 50kD Zein, Zea m 7, Zea m Chitinase, Zea m G1, Zea m G2, Zea m PAO, Zea m Zml 3), *Zeus* spp (Zeu fa 1), *Ziziphus* spp (Ziz m 1, Ziz m 1.0101), *Zoarces* spp (Zoa a ISP III), *Zygophyllum* spp (Zyg f 2)

In this context the terms in brackets indicate the particular preferred allergenic antigens (allergens) from the particular source.

Most preferably the allergenic antigen is preferably derived from a source (e.g. a plant (e.g. grass or a tree), a natural product (e.g. milk, nuts etc.), a fungal source (e.g. *Aspergillus*) or a bacterial source or from an animal source or animal poison (e.g. cat, dog, venom of bees etc.), preferably selected from the list consisting of grass pollen (e.g. pollen of rye), tree pollen (e.g. pollen of hazel, birch, alder, ash), flower pollen, herb pollen (e.g. pollen of mugwort), dust mite (e.g. Der f 1, Der p 1, Eur m 1, Der m 1 Der f 2, Der p 2, Eur m 2, Tyr p 2, Lep d 2), mold (e.g. allergens of *Acremonium, Aspergillus, Cladosporium, Fusarium, Mucor, Penicillium, Rhizopus, Stachybotrys, Trichoderma*, or *Alternaria*), animals (e.g Fel d1, Fel d 2, Fel d3, or Fel d4 of cats), food (e.g. allergens of fish (e.g. bass, cod, flounder), seafood (e.g. crab, lobster, shrimps), egg, wheat, nuts (e.g. peanuts, almonds, cashews, walnuts), soya, milk, etc.) or insect venom (e.g. allergens from the venom of wasps, bees, hornets, ants, mosquitos, or ticks).

Autoimmune self-antigens, i.e. antigens associated with autoimmune disease or autoantigens, may be associated with an autoimmune disease affecting at least one or more of the following organ systems: the circulatory system, the digestive system, the endocrine system, the excretory system, the immune system, the integumentary system, the muscular system, the nervous system, the reproductive system, the respiratory system, the skeletal system, preferably with the cardiovascular system, the neuroendocrine system, the musculoskeletal system or gastrointestinal system. Therein the circulatory system is the organ system which enables pumping and channeling blood to and from the body and lungs with heart, blood and blood vessels. The digestive system enables digestion and processing food with salivary glands, esophagus, stomach, liver, gallbladder, pancreas, intestines, colon, rectum and anus. The endocrine system enables communication within the body using hormones made by endocrine glands such as the hypothalamus, pituitary or pituitary gland, pineal body or pineal gland, thyroid gland, parathyroid gland and adrenal glands. The excretory system comprises kidneys, ureters, bladder and urethra and is involved in fluid balance, electrolyte balance and excretion of urine. The immune system comprises structures involved in the transfer of lymph between tissues and the blood stream, the lymph and the nodes and vessels which may be responsible for transport of cellular and humoral components of the immune system. It is responsible for defending against disease-causing agents and comprises amongst others leukocytes, tonsils, adenoids, *thymus* and spleen. The integumentary system comprises skin, hair and nails. The muscular system enables movement with muscles together with the skeletal system which comprises bones, cartilage, ligaments and tendons and provides structural support. The nervous system is responsible for collecting, transferring and processing information and comprises the brain, spinal cord and nerves. The reproductive system comprises the sex organs, such as ovaries, fallopian tubes, uterus, vagina, mammary glands, testes, vas deferens, seminal vesicles, prostate and penis. The respiratory system comprises the organs used for breathing, the pharynx, larynx, trachea, bronchi, lungs and diaphragm and acts together with the circulation system.

Autoimmune self-antigens (antigens associated with autoimmune disease or autoantigens) are selected from autoantigens associated with autoimmune diseases selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barré syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, borrelia arthritis), Méniere's disease (Morbus Méniere); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis nodosa (periarteiitis nodosa), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis).

These and other proteins acting as autoimmune self-antigens are understood to be therapeutic, as they are meant to treat the subject, in particular a mammal, more particularly a human being, by vaccinating with a self-antigen which is expressed by the mammal, e.g. the human, itself and which triggers an undesired immune response, which is not raised in a healthy subject. Accordingly, such proteins acting as self-antigens are typically of mammalian, in particular human origin.

Particularly preferred in this context are autoimmune self-antigens (autoantigens) selected from:
  myelin basic protein (MBP), proteolipid protein (PLP), and myelin oligodendrocyte glycoprotein (MOG), in each case associated with multiple sclerosis (MS);
  CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;
  interphotoreceptor retinoid-binding protein (IRBP) associated with autoimmune uveitis;
  acetylcholine receptor AchR, and insulin-like growth factor-1 receptor (IGF-1R), in each case associated with Myasthenia gravis;
  M-protein from beta-hemolytic streptocci (pseudo-autoantigen) associated with Rheumatic Fever;
  Macrophage migration inhibitory factor associated with Arthritis;
  Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjögren's syndrome;
  Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;
oxLDL, beta(2)GPI, HSP60/65, and oxLDL/beta(2)GPI, in each case associated with Atherosclerosis;
cardiac beta(1)-adrenergic receptor associated with idiopathic dilated cardiomyopathy (DCM);
histidyl-tRNA synthetase (HisRS) associated with myositis;
topoisomerase I associated with *scleroderma* disease.

Furthermore, in other embodiments said autoimmune self-antigen is associated with the respective autoimmune disease, like e.g. IL-17, heat shock proteins, and/or any idiotype pathogenic T cell or chemokine receptor which is expressed by immune cells involved in the autoimmune response in said autoimmune disease (such as any autoimmune diseases described herein).

The coding region of the inventive nucleic acid according to the first aspect of the present invention may occur as a mono-, di-, or even multicistronic nucleic acid, i.e. a nucleic acid which carries the coding sequences of one, two or more proteins or peptides. Such coding sequences in di-, or even multicistronic nucleic acids may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive nucleic acid sequence comprises a coding region, encoding a peptide or protein which comprises an allergenic antigen or an autoimmune self-antigen or a fragment, variant or derivative thereof. Preferably, the encoded allergenic antigen or auto-immune self-antigen is no histone protein. In the context of the present invention such a histone protein is typically a strongly alkaline protein found in eukaryotic cell nuclei, which package and order the DNA into structural units called nucleosomes. Histone proteins are the chief protein components of chromatin, act as spools around which DNA winds, and play a role in gene regulation. Without histones, the unwound DNA in chromosomes would be very long (a length to width ratio of more than 10 million to one in human DNA). For example, each human cell has about 1.8 meters of DNA, but wound on the histones it has about 90 millimeters of chromatin, which, when duplicated and condensed during mitosis, result in about 120 micrometers of chromosomes. More preferably, in the context of the present invention such a histone protein is typically defined as a highly conserved protein selected from one of the following five major classes of histones: H1/H5, H2A, H2B, H3, and H4", preferably selected from mammalian histone, more preferably from human histones or histone proteins. Such histones or histone proteins are typically organised into two super-classes defined as core histones, comprising histones H2A, H2B, H3 and H4, and linker histones, comprising histones H1 and H5.

In this context, linker histones, preferably excluded from the scope of protection of the pending invention, preferably mammalian linker histones, more preferably human linker histones, are typically selected from H1, including H1F, particularly including H1F0, H1FNT, H1FOO, H1FX, and H1H1, particularly including HIST1H1A, HIST1H1B, HIST1H1C, HIST1H1 D, HIST1H1E, HIST1H1T; and Furthermore, core histones, preferably excluded from the scope of protection of the pending invention, preferably mammalian core histones, more preferably human core histones, are typically selected from H2A, including H2AF, particularly including H2AFB1, H2AFB2, H2AFB3, H2AFJ, H2AFV, H2AFX, H2AFY, H2AFY2, H2AFZ, and H2A1, particularly including HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, and H2A2, particularly including HIST2H2AA3, HIST2H2AC; H2B, including H2BF, particularly including H2BFM, H2BFO, H2BFS, H2BFWT H2B1, particularly including HIST1H2BA, HIST1H2BB, HIST1H2BC, HIST1H2BD, HIST1H2BE, H1ST1H2BF, HIST1H2BG, HIST1H2BH, HIST1H2BI, HIST1H2BJ, HIST1H2BK, HIST1H2BL, HIST1H2BM, HIST1H2BN, HIST1H2BO, and H2B2, particularly including HIST2H2BE; H3, including H3A1, particularly including HIST1H3A, HIST1H3B, HIST1H3C, HIST1H3D, HIST1H3E, HIST1H3F, HIST1H3G, HIST1H3H, HIST1H3I, HIST1H3J, and H3A2, particularly including HIST2H3C, and H3A3, particularly including HIST3H3; H4, including H41, particularly including HIST1H4A, HIST1H4B, HIST1H4C, HIST1H4D, HIST1H4E, HIST1H4F, HIST1H4G, HIST1H4H, HIST1H4J, HIST1H4J, HIST1H4K, HIST1H4L, and H44, particularly including HIST4H4, and H5.

According to the first aspect of the present invention, the inventive nucleic acid sequence comprises a coding region, encoding a peptide or protein which comprises an allergenic antigen or an autoimmune self-antigen or a fragment, variant or derivative thereof. Preferably, the encoded allergenic antigen or auto-immune self-antigen is no reporter protein (e.g. Luciferase, Green Fluorescent Protein (GFP), Enhanced Green Fluorescent Protein (EGFP), β-Galactosidase) and no marker or selection protein (e.g. alpha-Globin, Galactokinase and Xanthine:guanine phosphoribosyl transferase (GPT)). Preferably, the nucleic acid sequence of the invention does not contain a (bacterial) antibiotics resistance gene, in particular not a neo gene sequence (Neomycin resistance gene) or CAT gene sequence (chloramphenicol acetyl transferase, chloramphenicol resistance gene).

The inventive nucleic acid as define above, comprises or codes for a) a coding region, encoding a peptide or protein which comprises an allergenic antigen or an autoimmune self-antigen or a fragment, variant or derivative thereof; b) at least one histone stem-loop, and c) a poly(A) sequence or polyadenylation signal; preferably for increasing the expression of said encoded peptide or protein, wherein the encoded peptide or protein is preferably no histone protein, no reporter protein and/or no marker or selection protein, as defined above. The elements b) to c) of the inventive nucleic acid may occur in the inventive nucleic acid in any order, i.e. the elements a), b) and c) may occur in the order a), b) and c) or a), c) and b) from 5' to 3' direction in the inventive nucleic acid sequence, wherein further elements as described herein, may also be contained, such as a 5'-CAP structure, a poly(C) sequence, stabilization sequences, IRES sequences, etc. Each of the elements a) to c) of the inventive nucleic acid, particularly a) in di- or multicistronic constructs and/or each of the elements b) and c), more preferably element b) may also be repeated at least once, preferably twice or more in the inventive nucleic acid. As an example, the inventive nucleic acid may show its sequence elements a), b) and optionally c) in e.g. the following order:
5'-coding region-histone stem-loop-poly(A) sequence-3'; or
5'-coding region-histone stem-loop-polyadenylation signal-3'; or
5'-coding region-poly(A) sequence-histone stem-loop-3'; or
5'-coding region-polyadenylation signal-histone stem-loop-3'; or
5'-coding region-coding region-histone stem-loop-polyadenylation signal-3'; or 5'-coding region-histone stem-loop-histone stem-loop-poly (A) sequence-3'; or 5'-coding region-histone stem-loop-histone stem-loop-polyadenylation signal-3'; etc.

In this context it is particularly preferred that the inventive nucleic acid sequence comprises or codes for a) a coding region, encoding a peptide or protein which comprises an allergenic antigen or an autoimmune self-antigen or fragment, variant or derivative thereof; b) at least one histone stem-loop, and c) a poly(A) sequence or polyadenylation sequence; preferably for increasing the expression level of said encoded peptide or protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

In a further preferred embodiment of the first aspect the inventive nucleic acid sequence as defined herein may also occur in the form of a modified nucleic acid.

In this context, the inventive nucleic acid sequence as defined herein may be modified to provide a "stabilized nucleic acid", preferably a stabilized RNA, more preferably an RNA that is essentially resistant to in vivo degradation (e.g. by an exo- or endo-nuclease). A stabilized nucleic acid may e.g. be obtained by modification of the G/C content of the coding region of the inventive nucleic acid sequence, by introduction of nucleotide analogues (e.g. nucleotides with backbone modifications, sugar modifications or base modifications) or by introduction of stabilization sequences in the 3'- and/or 5'-untranslated region of the inventive nucleic acid sequence.

As mentioned above, the inventive nucleic acid sequence as defined herein may contain nucleotide analogues/modifications e.g. backbone modifications, sugar modifications or base modifications. A backbone modification in connection with the present invention is a modification in which phosphates of the backbone of the nucleotides contained in inventive nucleic acid sequence as defined herein are chemically modified. A sugar modification in connection with the present invention is a chemical modification of the sugar of the nucleotides of the inventive nucleic acid sequence as defined herein. Furthermore, a base modification in connection with the present invention is a chemical modification of the base moiety of the nucleotides of the nucleic acid molecule of the inventive nucleic acid sequence. In this context nucleotide analogues or modifications are preferably selected from nucleotide analogues which are applicable for transcription and/or translation.

In a particular preferred embodiment of the first aspect of the present invention the herein defined nucleotide analogues/modifications are selected from base modifications which additionally increase the expression of the encoded protein and which are preferably selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to a further embodiment, the inventive nucleic acid sequence as defined herein can contain a lipid modification. Such a lipid-modified nucleic acid typically comprises a nucleic acid as defined herein. Such a lipid-modified nucleic acid molecule of the inventive nucleic acid sequence as defined herein typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule. In this context it is particularly preferred that the lipid modification is present at the terminal ends of a linear inventive nucleic acid sequence.

According to another preferred embodiment of the first aspect of the invention, the inventive nucleic acid sequence as defined herein, particularly if provided as an (m)RNA, can therefore be stabilized against degradation by RNases by the addition of a so-called "5' CAP" structure.

According to a further preferred embodiment of the first aspect of the invention, the inventive nucleic acid sequence as defined herein can be modified by a sequence of at least 10 cytidines, preferably at least 20 cytidines, more preferably at least 30 cytidines (so-called "poly(C) sequence"). Particularly, the inventive nucleic acid sequence may contain or code for a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. This poly(C) sequence is preferably located 3' of the coding region comprised in the inventive nucleic acid according to the first aspect of the present invention.

In a particularly preferred embodiment of the present invention, the G/C content of the coding region, encoding at least one peptide or protein which comprises an allergenic antigen or an autoimmune self-antigen or a fragment, variant or derivative thereof of the inventive nucleic acid sequence as defined herein, is modified, particularly increased, compared to the G/C content of its particular wild type coding region, i.e. the unmodified coding region. The encoded amino acid sequence of the coding region is preferably not modified compared to the coded amino acid sequence of the particular wild type coding region.

The modification of the G/C-content of the coding region of the inventive nucleic acid sequence as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid sequence as defined herein, there are various possibilities for modification of the nucleic acid sequence, e.g. the coding region, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the coding region of the inventive nucleic acid sequence as defined herein, compared to its particular wild type coding region (i.e. the original sequence). Thus, for example, all codons for Thr occurring in the wild type sequence can be modified to ACC (or ACG).

In the above context, codons present in mRNA are shown. Therefore uridine present in an mRNA may also be present as thymidine in the respective DNA coding for the particular mRNA.

Preferably, the G/C content of the coding region of the inventive nucleic acid sequence as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein which comprises an allergenic antigen or an autoimmune self-antigen or a fragment, variant or derivative thereof are substituted, thereby increasing the G/C content of said coding region.

In this context, it is particularly preferable to increase the G/C content of the coding region of the inventive nucleic acid sequence as defined herein, to the maximum (i.e. 100% of the substitutable codons), compared to the wild type coding region.

According to the invention, a further preferred modification of the coding region encoding at least one peptide or protein which comprises an allergenic antigen or an autoimmune self-antigen or a fragment, variant or derivative thereof of the inventive nucleic acid sequence as defined herein, is based on the finding that the translation efficiency is also determined by a different frequency in the occurrence of tRNAs in cells. Thus, if so-called "rare codons" are present in the coding region of the inventive nucleic acid sequence as defined herein, to an increased extent, the corresponding modified nucleic acid sequence is translated to a significantly poorer degree than in the case where codons coding for relatively "frequent" tRNAs are present.

In this context the coding region of the inventive nucleic acid sequence is preferably modified compared to the corresponding wild type coding region such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the coding region of the inventive nucleic acid sequence as defined herein, is modified such that codons for which frequently occurring tRNAs are available are inserted. In other words, according to the invention, by this modification all codons of the wild type coding region which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the coding region of the inventive nucleic acid sequence as defined herein, with the "frequent" codons without modifying the amino acid sequence of the peptide or protein encoded by the coding region of the nucleic acid sequence. This preferred embodiment allows provision of a particularly efficiently translated and stabilized (modified) inventive nucleic acid sequence as defined herein.

According to another preferred embodiment of the first aspect of the invention, the inventive nucleic acid sequence as defined herein, preferably has additionally at least one 5' and/or 3' stabilizing sequence. These stabilizing sequences in the 5' and/or 3' untranslated regions have the effect of increasing the half-life of the nucleic acid, particularly of the mRNA in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid. Another example of a stabilizing sequence has the general formula $(C/U)CCAN_xCCC(U/A)Py_xUC(C/U)CC$ (SEQ ID NO: 55), which is contained in the 3'-UTRs of the very stable RNAs which code for (alpha-)globin, type(I)-collagen, 15-lipoxygenase or for tyrosine hydroxylase (cf. Holcik et al, Proc. Natl. Acad. Sci. USA 1997, 94: 2410 to 2414). Such stabilizing sequences can of course be used individually or in combination with one another and also in combination with other stabilizing sequences known to a person skilled in the art. In this context it is particularly preferred that the 3' UTR sequence of the alpha globin gene is located 3' of the coding region encoding at least one peptide or protein which comprises an allergenic antigen or an autoimmune self-antigen or a fragment, variant or derivative thereof comprised in the inventive nucleic acid sequence according to the first aspect of the present invention.

Substitutions, additions or eliminations of bases are preferably carried out with the inventive nucleic acid sequence as defined herein, using a DNA matrix for preparation of the nucleic acid sequence by techniques of the well-known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001).

Any of the above modifications may be applied to the inventive nucleic acid sequence as defined herein and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

Nucleic acid sequences used according to the present invention as defined herein may be prepared using any method known in the art, including synthetic methods such as e.g. solid phase synthesis, as well as in vitro methods, such as in vitro transcription reactions or in vivo reactions, such as in vivo propagation of DNA plasmids in bacteria.

In such a process, for preparation of the inventive nucleic acid sequence as defined herein, especially if the nucleic acid is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

The inventive nucleic acid sequence as defined herein as well as proteins or peptides as encoded by this nucleic acid sequence may comprise fragments or variants of those sequences. Such fragments or variants may typically comprise a sequence having a sequence identity with one of the above mentioned nucleic acids, or with one of the proteins or peptides or sequences, if encoded by the inventive nucleic acid sequence, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

"Fragments" of proteins or peptides in the context of the present invention (e.g. as encoded by the inventive nucleic acid sequence as defined herein) may comprise a sequence of a protein or peptide as defined herein, which is, with regard to its amino acid sequence (or its encoded nucleic acid molecule), N-terminally, C-terminally and/or intrasequentially truncated/shortened compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'-, 3'- and/or intrasequentially truncated7shortened compared to the nucleic acid molecule of the original (native) nucleic acid molecule. A sequence identity with respect to such a fragment as defined herein may therefore preferably refer to the entire nucleic acid as defined herein and the preferred sequence identity level typically is as indicated herein. Fragments have the same biological function or specific activity or at least retain an activity of the natural full length protein of at least 50%, more preferably at least 70%, even more preferably at least 90% (measured in an appropriate functional assay, e.g. an assay assessing the immune reaction, e.g. the TH1 and/TH2 reaction by e.g. detecting the secretion and/or expression of cytokines indicating the strength of the immune response) as compared to the full-length native wt peptide or protein, e.g. its specific antigenic or therapeutic property. Accordingly, in a preferred embodiment, the "fragment" is a portion of the full-length (naturally occurring) wt allergenic or self-antigenic protein, which exerts therapeutic properties as indicated herein, e.g. for vaccination.

Fragments of proteins or peptides in the context of the present invention (e.g. as encoded by the inventive nucleic acid sequence as defined herein) may furthermore comprise a sequence of a protein or peptide as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides as defined herein may comprise at least one epitope of those proteins or peptides. Furthermore also domains of a protein, like the extracellular domain, the intracellular domain or the transmembrane domain and shortened or truncated versions of a protein may be understood to comprise/correspond to a fragment of a protein.

Fragments of proteins or peptides as defined herein (e.g. as encoded by the inventive nucleic acid sequence as defined herein) may also comprise epitopes of those proteins or peptides. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

"Variants" of proteins or peptides as defined in the context of the present invention may be encoded by the inventive nucleic acid sequence as defined herein. Thereby, a protein or peptide may be generated, having an amino acid sequence which differs from the original sequence in one or more (2, 3, 4, 5, 6, 7 or more) mutation(s), such as one or more substituted, inserted and/or deleted amino acid(s). The preferred level of sequence identity of "variants" in view of the full-length natural wt protein sequence typically is as indicated herein. Preferably, variants have the same biological function or specific activity or at least retain an activity of the natural full length protein of at least 50%, more preferably at least 70%, even more preferably at least 90% (measured in an appropriate functional assay, e.g. an assay assessing the immune reaction, e.g. the TH1 and/TH2 reaction by e.g. detecting the secretion and/or expression of cytokines indicating the strength of the immune response) as compared to the full-length native peptide or protein, e.g. its specific antigenic of therapeutic property. Accordingly, in a preferred embodiment, the "variant" is a variant of an allergenic or self-antigenic protein, which exerts therapeutic properties, e.g. as a vaccine, to the extent as indicated herein.

"Variants" of proteins or peptides as defined in the context of the present invention (e.g. as encoded by a nucleic acid as defined herein) may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by the inventive nucleic acid sequence as defined herein, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by the inventive nucleic acid sequence as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The inventive nucleic acid sequence as defined herein may encode derivatives of a peptide or protein. Such a derivative of a peptide or protein is a molecule that is derived from another molecule, such as said peptide or protein. A "derivative" typically contains the full-length sequence of the natural wt peptide or protein and additional sequence features, e.g. at the N- or at the C-terminus, which may exhibit an additional function to the natural full-length peptide/protein. Again such derivatives have the same biological function or specific activity or at least retain an activity of the natural wt full-length protein of at least 50%, more preferably at least 70%, even more preferably at least 90% (measured in an appropriate functional assay, see above, e.g. an assay measuring the immune reaction) as compared to the full-length native wt peptide or protein, e.g. its specific allergenic/self-antigenic therapeutic property. Thereby, a "derivative" of a peptide or protein also encompasses (chimeric) fusion peptides/proteins comprising a peptide or protein used in the present invention or a natural wt full-length protein (or variant/fragment thereof) fused to a distinct peptide/protein awarding e.g. two or more biological functions to the fusion peptide/protein. For example, the fusion may comprise a label, such as, for example, an epitope, e.g., a FLAG epitope or a V5 epitope or an HA epitope. For example, the epitope is a FLAG epitope. Such a tag is useful for, for example, purifying the fusion protein.

In this context, a "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide. Analogously, a "variant" of a nucleic acid sequence or, particularly, a fragment, may have at least 70%, 75%, 80%, 85%, 90%, 95%, 98% or 99% nucleotide identity over a stretch of 10, 20, 30, 50, 75 or 100 nucleotide of such nucleic acid sequence; typically, however, referring to the naturally occurring wt full-length sequences. In case of "fragments" typically, sequence identity is determined for the fragment over the length (of the fragment) on the portion of the full-length protein (reflecting the same length as the fragment), which exhibits the highest level of sequence identity.

In a further preferred embodiment of the first aspect of the present invention the inventive nucleic acid sequence is associated with a vehicle, transfection or complexation agent for increasing the transfection efficiency and/or the immunostimulatory properties of the inventive nucleic acid sequence. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

In this context it is particularly preferred that the inventive nucleic acid is complexed at least partially with a cationic or polycationic compound, preferably cationic proteins or peptides. Partially means that only a part of the inventive nucleic acid is complexed with a cationic or polycationic compound and that the rest of the inventive nucleic acid is in uncomplexed form ("free"). Preferably the ratio of complexed nucleic acid to:free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

It is preferred that the nucleic acid sequence of the invention is provided in either naked form or complexed, e.g. by polycationic compounds of whatever chemical structure, preferably polycationic (poly)peptides or synthetic polycationic compounds. Preferably, the nucleic acid sequence is not provided together with a packaging cell.

In a further aspect the invention provides for a composition or kit or kit of parts comprising a plurality or more than one, preferably 2 to 10, more preferably 2 to 5, most preferably 2 to 4 of the inventive nucleic acid sequences as defined herein. These inventive compositions comprise more than one inventive nucleic acid sequences, preferably encoding different peptides or proteins which comprise preferably different allergenic antigens or auto-immune self-antigens or fragments, variants or derivatives thereof.

According to a further aspect, the present invention also provides a method for increasing the expression of an encoded peptide or protein comprising the steps, e.g. a) providing the inventive nucleic acid sequence as defined herein or the inventive composition comprising a plurality (which means typically more than 1, 2, 3, 4, 5, 6 or more than 10 nucleic acids, e.g. 2 to 10, preferably 2 to 5 nucleic acids) of inventive nucleic acid sequences as defined herein, b) applying or administering the inventive nucleic acid sequence as defined herein or the inventive composition comprising a plurality of inventive nucleic acid sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of allergies or autoimmune diseases, preferably as defined herein.

In this context in vitro is defined herein as transfection or transduction of the inventive nucleic acid as defined herein or of the inventive composition comprising a plurality of inventive nucleic acid sequences as defined herein into cells in culture outside of an organism; in vivo is defined herein as transfection or transduction of the inventive nucleic acid or of the inventive composition comprising a plurality of inventive nucleic acid sequences (which means typically more than 1, 2, 3, 4, 5, 6 or more than 10 nucleic acids, e.g. 2 to 10, preferably 2 to 5 nucleic acids) into cells by application of the inventive nucleic acid or of the inventive composition to the whole organism or individual and ex vivo is defined herein as transfection or transduction of the inventive nucleic acid or of the inventive composition comprising a plurality of inventive nucleic acid sequences into cells outside of an organism or individual and subsequent application of the transfected cells to the organism or individual.

Likewise, according to another aspect, the present invention also provides the use of the inventive nucleic acid sequence as defined herein or of the inventive composition comprising a plurality of inventive nucleic acid sequences as defined herein, preferably for diagnostic or therapeutic purposes, for increasing the expression of an encoded peptide or protein, e.g. by applying or administering the inventive nucleic acid sequence as defined herein or of the inventive composition comprising a plurality of inventive nucleic acid sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of allergies or autoimmune diseases, preferably as defined herein.

In yet another aspect the present invention also relates to an inventive expression system comprising an inventive nucleic acid sequence or expression vector or plasmid according to the first aspect of the present invention. In this context the expression system may be a cell-free expression system (e.g. an in vitro transcription/translation system), a cellular expression system (e.g. mammalian cells like CHO cells, insect cells, yeast cells, bacterial cells like *E. coli*) or organisms used for expression of peptides or proteins (e.g. plants or animals like cows).

Additionally, according to another aspect, the present invention also relates to the use of the inventive nucleic acid as defined herein or of the inventive composition comprising a plurality of inventive nucleic acid sequences as defined herein for the preparation of a pharmaceutical composition for increasing the expression of an encoded peptide or protein, e.g. for treating allergies or autoimmune diseases, preferably as defined herein, e.g. applying or administering the inventive nucleic acid as defined herein or of the inventive composition comprising a plurality of inventive nucleic acid sequences as defined herein to a cell (e.g. an expression host cell or a somatic cell), a tissue or an organism, preferably in naked form or complexed form or as a pharmaceutical composition or vaccine as described herein, more preferably using any of the administration modes as described herein.

Accordingly, in a particular preferred aspect, the present invention also provides a pharmaceutical composition, comprising an inventive nucleic acid as defined herein or an inventive composition comprising a plurality of inventive nucleic acid sequences as defined herein and optionally a pharmaceutically acceptable carrier and/or vehicle.

As a first ingredient, the inventive pharmaceutical composition comprises at least one inventive nucleic acid as defined herein.

As a second ingredient the inventive pharmaceutical composition may optional comprise at least one additional pharmaceutically active component. A pharmaceutically active component in this connection is a compound that has a therapeutic effect to heal, ameliorate or prevent a particular indication or disease as mentioned herein, preferably allergies or autoimmune diseases. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive nucleic acid sequence as vehicle, transfection or complexation agent.

The inventive pharmaceutical composition can additionally contain one or more auxiliary substances in order to increase its immunogenicity or immunostimulatory capacity, if desired. A synergistic action of the inventive nucleic acid sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

The inventive pharmaceutical composition as defined herein may also be administered orally in any orally acceptable dosage form including, but not limited to, capsules, tablets, aqueous suspensions or solutions.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs.

For topical applications, the inventive pharmaceutical composition may be formulated in a suitable ointment, containing the inventive nucleic acid as defined herein suspended or dissolved in one or more carriers.

The inventive pharmaceutical composition typically comprises a "safe and effective amount" of the components of the inventive pharmaceutical composition, particularly of the inventive nucleic acid sequence(s) as defined herein. As used herein, a "safe and effective amount" means an amount of the inventive nucleic acid sequence(s) as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive nucleic acid sequence as defined herein or the inventive composition comprising a plurality of inventive nucleic acid sequences as defined herein) may be provided or used as a vaccine. Typically, such a vaccine is as defined above for pharmaceutical compositions. Additionally, such a vaccine typically contains the inventive nucleic acid as defined herein or the inventive composition comprising a plurality of inventive nucleic acid sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

The present invention furthermore provides several applications and uses of the inventive nucleic acid sequence as defined herein, of the inventive composition comprising a plurality of inventive nucleic acid sequences as defined herein, of the inventive pharmaceutical composition, of the inventive vaccine, all comprising the inventive nucleic acid sequence as defined herein or of kits comprising same.

According to one specific aspect, the present invention is directed to the first medical use of the inventive nucleic acid sequence as defined herein or of the inventive composition comprising a plurality of inventive nucleic acid sequences as defined herein as a medicament, preferably as a vaccine particularly in the treatment of allergies or autoimmune diseases.

According to another aspect, the present invention is directed to the second medical use of the inventive nucleic acid sequence as defined herein or of the inventive composition comprising a plurality of inventive nucleic acid sequences as defined herein, for the treatment allergies our autoimmune diseases as defined herein, preferably to the use of the inventive nucleic acid sequence as defined herein, of the inventive composition comprising a plurality of inventive nucleic acid sequences as defined herein, of a pharmaceutical composition or vaccine comprising same or of kits comprising same for the preparation of a medicament for the prophylaxis, treatment and/or amelioration of allergies or autoimmune diseases as defined herein. Preferably, the pharmaceutical composition or a vaccine is used or to be administered to a patient in need thereof for this purpose.

Preferably, diseases as mentioned herein are selected from allergies which preferably include e.g. pollen allergy (allergy against grass pollen, tree pollen (e.g. pollen of hazel, birch, alder, ash), flower pollen, herb pollen (e.g. pollen of mugwort)), dust mite allergy, mold allergy (e.g. allergy against *Acremonium, Aspergillus, Cladosporium, Fusarium, Mucor, Penicillium, Rhizopus, Stachybotrys, Trichoderma,* or *Alternaria*), pet allergy (allergy against animals; e.g against cats, dogs, horses), food allergy (e.g. allergy against fish (e.g. bass, cod, flounder), seafood (e.g. crab, lobster, shrimps), egg, wheat, nuts (e.g. peanuts, almonds, cashews, walnuts), soya, milk, etc.) or insect bite allergy (allergy against insect venom, e.g. venom of wasps, bees, hornets, ants, mosquitos, or ticks).

According to another specific embodiment, diseases as defined herein comprise autoimmune diseases as defined in the following. autoimmune diseases are preferably selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barré syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, borrelia arthritis), Ménierè's disease (Morbus Ménierè); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus-vulgaris, bullous pemphigoid, scar forming pemphigoid; polyarteriitis nodosa (periarteiitis nodosa), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis)

In a further preferred aspect, the inventive nucleic acid sequence as defined herein or the inventive composition comprising a plurality of inventive nucleic acid sequences as defined herein may be used for the preparation of a pharmaceutical composition or a vaccine, particularly for purposes as defined herein.

The inventive pharmaceutical composition or vaccine may furthermore be used for the treatment of a disease or a disorder, preferably of allergies or autoimmune diseases as defined herein.

According to a final aspect, the present invention also provides kits, particularly kits of parts. Such kits, particularly kits of parts, typically comprise as components alone or in combination with further components as defined herein at least one inventive nucleic acid sequence as defined herein, the inventive pharmaceutical composition or vaccine comprising the inventive nucleic acid sequence. The at least one inventive nucleic acid sequence as defined herein, optionally in combination with further components as defined herein, whereby the at least one nucleic acid of the invention is provided separately (first part of the kit) from at least one other part of the kit comprising one or more other components. The inventive pharmaceutical composition and/or the inventive vaccine may e.g. occur in one or different parts of the kit. As an example, e.g. at least one part of the kit may comprise at least one inventive nucleic acid sequence as defined herein, and at least one further part of the kit at least one other component as defined herein, e.g. at least one other part of the kit may comprise at least one pharmaceutical composition or vaccine or a part thereof, e.g. at least one part of the kit may comprise the inventive nucleic acid sequence as defined herein, at least one further part of the kit at least one other component as defined herein, at least one further part of the kit at least one component of the inventive pharmaceutical composition or vaccine or the inventive pharmaceutical composition or vaccine as a whole, and at least one further part of the kit e.g. at least one pharmaceutical carrier or vehicle, etc. In case the kit or kit of parts comprises a plurality of inventive nucleic acid sequences, one component of the kit can comprise only one, several or all inventive nucleic acid sequences comprised in the kit. In an alternative embodiment every/each inventive nucleic acid sequence may be comprised in a different/separate component of the kit such that each component forms a part of the kit. Also, more than one nucleic acid may be comprised in a first component as part of the kit, whereas one or more other (second, third etc.) components (providing one or more other parts of the kit) may either contain one or more than one inventive nucleic acids, which may be identical or partially identical or different from the first component. The kit or kit of parts may furthermore contain technical instructions with information on the administration and dosage of the inventive nucleic acid sequence, the inventive pharmaceutical composition or the inventive vaccine or of any of its components or parts, e.g. if the kit is prepared as a kit of parts.

Taken together, the invention provides a nucleic acid sequence comprising or coding for
a) a coding region, encoding at least one peptide or protein;
b) at least one histone stem-loop, and
c) a poly(A) sequence or a polyadenylation signal;
wherein said protein or peptide antigen is an allergenic antigen or a fragment, variant or derivative of said allergenic antigen, or an autoimmune self-antigen associated with an autoimmune disease.

Preferably, the invention provides a provides a nucleic acid sequence comprising or coding for
a) a coding region, encoding at least one peptide or protein;
b) at least one histone stem-loop, and
c) a poly(A) sequence or a polyadenylation signal;
wherein said protein or peptide antigen is an allergenic antigen or a fragment, variant or derivative of said allergenic antigen, or an autoimmune self-antigen associated with an autoimmune disease, wherein the autoimmune disease is associated with at least one organ system, particularly with the circulatory system, the digestive system, the endocrine system, the excretory system, the immune system, the integumentary system, the muscular system, the nervous system, the reproductive system, the respiratory system, the skeletal system, preferably with the cardiovascular system, the neuroendocrine system, the musculoskeletal system or gastrointestinal system.

Preferably, the invention provides a nucleic acid sequence comprising or coding for
a) a coding region, encoding at least one peptide or protein;
b) at least one histone stem-loop, and
c) a poly(A) sequence or a polyadenylation signal;
wherein said protein or peptide antigen is an allergenic antigen or a fragment, variant or derivative of said allergenic antigen, or an autoimmune self-antigen associated with an autoimmune disease, preferably wherein said protein or peptide antigen is an autoimmune self-antigen associated with an autoimmune disease selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barré syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, borrelia arthritis), Ménierè's disease (Morbus Ménierè); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis nodosa (periarteiitis nodosa), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis), or a fragment, variant or derivative of said autoimmune self-antigen.

Preferably, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said protein or peptide antigen is an allergenic antigen or a fragment, variant or derivative of said allergenic antigen, or an autoimmune self-antigen associated with an autoimmune disease, preferably wherein the said protein or peptide antigen is an autoimmune self-antigen associated with an autoimmune disease, particularly an self-antigen selected from
  myelin basic protein (MBP), proteolipid protein (PLP), and myelin oligodendrocyte glycoprotein (MOG), in each case associated with multiple sclerosis (MS);
  CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;
  interphotoreceptor retinoid-binding protein (IRBP) associated with autoimmune uveitis;
  acetylcholine receptor AchR, and insulin-like growth factor-1 receptor (IGF-1R), in each case associated with Myasthenia gravis;
  M-protein from beta-hemolytic streptocci (pseudo-autoantigen) associated with Rheumatic Fever;
  Macrophage migration inhibitory factor associated with Arthritis;
  Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjögren's syndrome;
  Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;
  oxLDL, beta(2)GPI, HSP60/65, and oxLDL/beta(2)GPI, in each case associated with Atherosclerosis;
  cardiac beta(1)-adrenergic receptor associated with idiopathic dilated cardiomyopathy (DCM);
  histidyl-tRNA synthetase (HisRS) associated with myositis;
  topoisomerase I associated with scleroderma disease.

Preferably, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said protein or peptide antigen is an allergenic antigen or a fragment, variant or derivative of said allergenic antigen, or an autoimmune self-antigen associated with an autoimmune disease, preferably, wherein said protein or peptide antigen is an allergenic antigen derived from a source selected from the list consisting of: grass pollen, tree pollen, flower pollen, herb pollen, dust mite, mold, animals, food, and insect venom, or a fragment, variant or derivative of said allergenic antigen.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

FIGURES

The following Figures are intended to illustrate the invention further and shall not be construed to limit the present invention thereto.

FIG. 1: shows the histone stem-loop consensus sequence generated from metazoan and protozoan stem loop sequences (as reported by Dávila López, M., & Samuelsson, T. (2008), RNA (New York, N.Y.), 14(1), 1-10. doi:10.1261/rna.782308). 4001 histone stem-loop sequences from metazoa and protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 2: shows the histone stem-loop consensus sequence generated from protozoan stem loop sequences (as reported by Dávila López, M., & Samuelsson, T. (2008), RNA (New York, N.Y.), 14(1), 1-10. doi:10.1261/rna.782308). 131 histone stem-loop sequences from protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 3: shows the histone stem-loop consensus sequence generated from metazoan stem loop sequences (as reported by Dávila López, M., & Samuelsson, T. (2008), RNA (New York, N.Y.), 14(1), 1-10. doi:10.1261/rna.782308). 3870 histone stem-loop sequences from metazoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 4: shows the histone stem-loop consensus sequence generated from vertebrate stem loop sequences (as reported by Dávila López, M., & Samuelsson, T. (2008), RNA (New York, N.Y.), 14(1), 1-10. doi:10.1261/rna.782308). 1333 histone stem-loop sequences from vertebrates were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 5: shows the histone stem-loop consensus sequence generated from human (Homo sapiens) stem loop sequences (as reported by Dávila López, M., & Samuelsson, T. (2008), RNA (New York, N.Y.), 14(1), 1-10. doi:10.1261/rna.782308). 84 histone stem-loop sequences from humans were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIGS. 6 to 19: show mRNAs from in vitro transcription. Given are the designation and the sequence of mRNAs obtained by in vitro transcription. The following abbreviations are used:

ppLuc (GC): GC-enriched mRNA sequence coding for Photinus pyralis luciferase
ag: 3' untranslated region (UTR) of the alpha globin gene
A64: poly(A)-sequence with 64 adenylates
A120: poly(A)-sequence with 120 adenylates
histoneSL: histone stem-loop
aCPSL: stem loop which has been selected from a library for its specific binding of the αCP-2KL protein
PolioCL: 5' clover leaf from Polio virus genomic RNA
G30: poly(G) sequence with 30 guanylates
U30: poly(U) sequence with 30 uridylates
SL: unspecific/artificial stem-loop
N32: unspecific sequence of 32 nucleotides
MmMOG (wt): wild type mRNA sequence encoding murine myelin-oligodendroglialprotein (MOG)
Within the sequences, the following elements are highlighted: coding region (ORF) (capital letters), ag (bold), histoneSL (underlined), further distinct sequences tested (italic).

FIG. 6: shows the mRNA sequence of ppLuc(GC)-ag (SEQ ID NO: 43). By linearization of the original vector at the restriction site immediately following the alpha-globin 3'-UTR (ag), mRNA is obtained lacking a poly(A) sequence.

FIG. 7: shows the mRNA sequence of ppLuc(GC)-ag-A64 (SEQ ID NO: 44). By linearization of the original vector at the restriction site immediately following the A64 poly(A)-sequence, mRNA is obtained ending with an A64 poly(A) sequence.

FIG. 8: shows the mRNA sequence of ppLuc(GC)-ag-histoneSL (SEQ ID NO: 45). The A64 poly(A) sequence was replaced by a histoneSL. The histone stem-loop sequence used in the examples was obtained from Cakmakci et al. (2008). Molecular and Cellular Biology, 28(3), 1182-1194.

FIG. 9: shows the mRNA sequence of ppLuc(GC)-ag-A64-histoneSL (SEQ ID NO: 46).
The histoneSL was appended 3' of A64 poly(A).

FIG. 10: shows the mRNA sequence of ppLuc(GC)-ag-A120 (SEQ ID NO: 47). The A64 poly(A) sequence was replaced by an A120 poly(A) sequence.

FIG. 11: shows the mRNA sequence of ppLuc(GC)-ag-A64-ag (SEQ ID NO: 48). A second alpha-globin 3'-UTR was appended 3' of A64 poly(A).

FIG. 12: shows the mRNA sequence of ppLuc(GC)-ag-A64-aCPSL (SEQ ID NO: 49).
A stem loop was appended 3' of A64 poly(A). The stem loop has been selected from a library for its specific binding of the αCP-2KL protein (Thisted et at, (2001), The Journal of Biological Chemistry, 276(20), 17484-17496). αCP-2KL is an isoform of αCP-2, the most strongly expressed αCP protein (alpha-globin mRNA poly(C) binding protein) (Makeyev et at, (2000), Genomics, 67(3), 301-316), a group of RNA binding proteins, which bind to the alpha-globin 3'-UTR (Chkheidze et at, (1999), Molecular and Cellular Biology, 19(7), 4572-4581).

FIG. 13: shows the mRNA sequence of ppLuc(GC)-ag-A64-PolioCL (SEQ ID NO: 50).

The 5' clover leaf from Polio virus genomic RNA was appended 3' of A64 poly(A).

FIG. 14: shows the mRNA sequence of ppLuc(GC)-ag-A64-G30 (SEQ ID NO: 51) A stretch of 30 guanylates was appended 3' of A64 poly(A).

FIG. 15: shows the mRNA sequence of ppLuc(GC)-ag-A64-U30 (SEQ ID NO: 52) A stretch of 30 uridylates was appended 3' of A64 poly(A).

FIG. 16: shows the mRNA sequence of ppLuc(GC)-ag-A64-SL (SEQ ID NO: 53) A stem loop was appended 3' of A64 poly(A). The upper part of the stem and the loop were taken from (Babendure et at, (2006), RNA (New York, N.Y.), 12(5), 851-861). The stem loop consists of a 17 base pair long, CG-rich stem and a 6 base long loop.

FIG. 17: shows ppLuc(GC)-ag-A64-N32 (SEQ ID NO: 54)

By linearization of the original vector at an alternative restriction site, mRNA is obtained with 32 additional nucleotides following poly(A).

FIG. 18: shows the mRNA sequence of MmMOG(wt)-ag-A64-C30 (SEQ ID NO: 55)

FIG. 19: shows the mRNA sequence of MmMOG(wt)-ag-A64-C30-histoneSL (SEQ ID NO: 56)

FIG. 20: shows that the combination of poly(A) and histoneSL increases protein expression from mRNA in a synergistic manner.

The effect of poly(A) sequence, histoneSL, and the combination of poly(A) and histoneSL on luciferase expression from mRNA was examined. Therefore different mRNAs were electroporated into HeLa cells. Luciferase levels were measured at 6, 24, and 48 hours after transfection. Little luciferase is expressed from mRNA having neither poly(A) sequence nor histoneSL. Both a poly(A) sequence or the histoneSL increase the luciferase level. Strikingly however, the combination of poly(A) and histoneSL further strongly increases the luciferase level, manifold above the level observed with either of the individual elements, thus acting synergistically. Data are graphed as mean RLU±SD (relative light units±standard deviation) for triplicate transfections. Specific RLU are summarized in Example 10.2.

Figure 21:
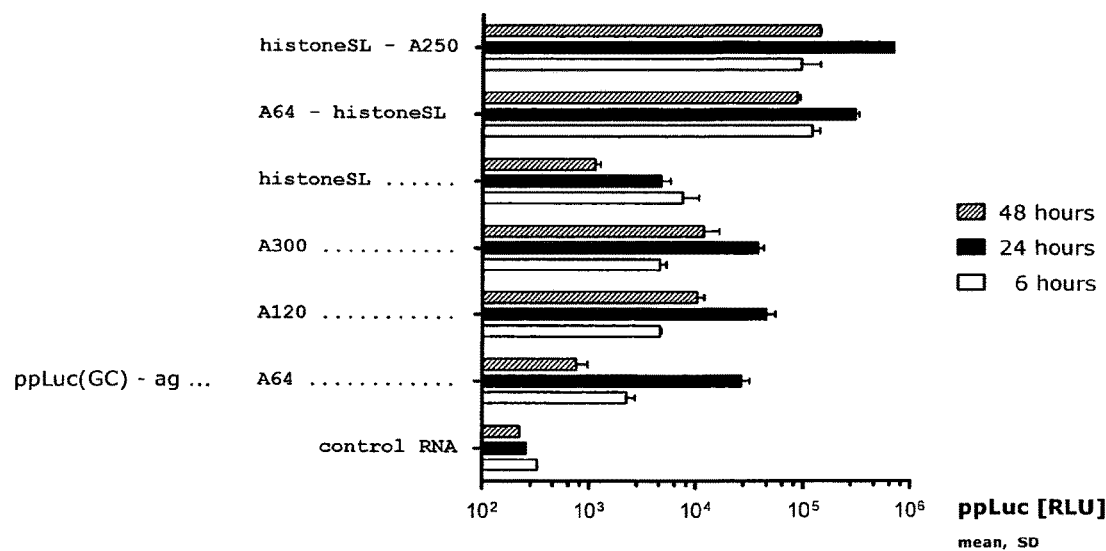

FIG. 21: shows that the combination of poly(A) and histoneSL increases protein expression from mRNA irrespective of their order.

The effect of poly(A) sequence, histoneSL, the combination of poly(A) and histoneSL, and their order on luciferase expression from mRNA was examined. Therefore different mRNAs were lipofected into HeLa cells. Luciferase levels were measured at 6, 24, and 48 hours after the start of transfection. Both an A64 poly(A) sequence or the histoneSL give rise to comparable luciferase levels. Increasing the length of the poly(A) sequence from A64 to A120 or to A300 increases the luciferase level moderately. In contrast, the combination of poly(A) and histoneSL increases the luciferase level much further than lengthening of the poly(A) sequence. The combination of poly(A) and histoneSL acts synergistically as it increases the luciferase level manifold above the level observed with either of the individual elements. The synergistic effect of the combination of poly(A) and histoneSL is seen irrespective of the order of poly(A) and histoneSL and irrespective of the length of poly(A) with A64-histoneSL or histoneSL-A250 mRNA. Data are graphed as mean RLU±SD for triplicate transfections. Specific RLU are summarized in Example 10.3.

Figure 22:
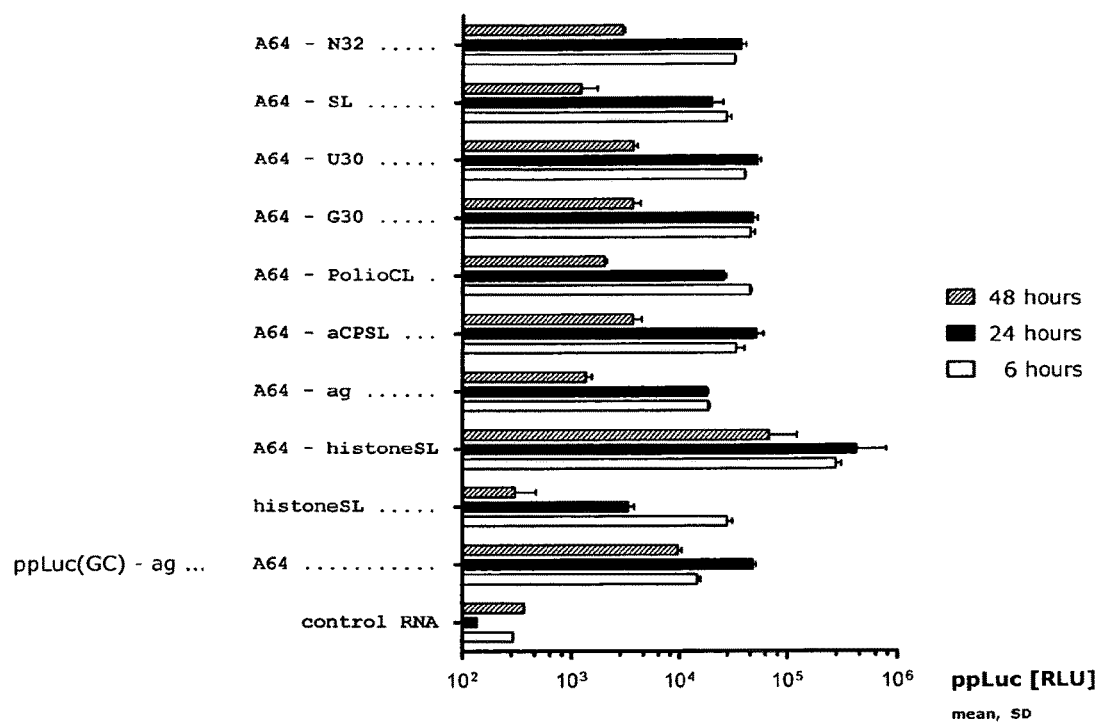

FIG. 22: shows that the rise in protein expression by the combination of poly(A) and histoneSL is specific.

The effect of combining poly(A) and histoneSL or poly(A) and alternative sequences on luciferase expression from mRNA was examined. Therefore different mRNAs were electroporated into HeLa cells. Luciferase levels were measured at 6, 24, and 48 hours after transfection. Both a poly(A) sequence or the histoneSL give rise to comparable luciferase levels. The combination of poly(A) and histoneSL strongly increases the luciferase level, manifold above the level observed with either of the individual elements, thus acting synergistically. In contrast, combining poly(A) with any of the other sequences is without effect on the luciferase level compared to mRNA containing only a poly(A) sequence. Thus, the combination of poly(A) and histoneSL acts specifically and synergistically. Data are graphed as mean RLU±SD for triplicate transfections. Specific RLU are summarized in Example 10.4.

Figure 23:
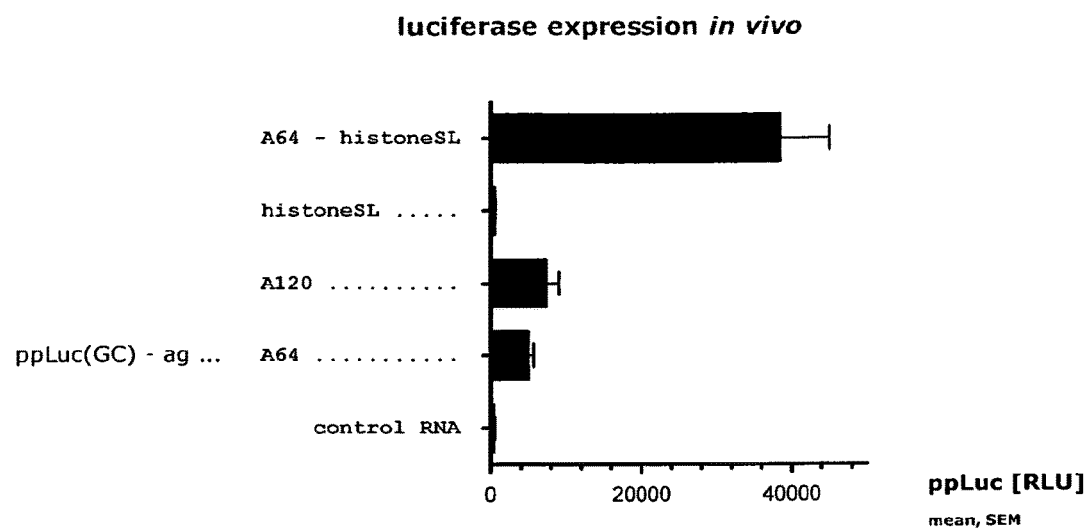

FIG. 23: shows that the combination of poly(A) and histoneSL increases protein expression from mRNA in a synergistic manner in vivo.

The effect of poly(A) sequence, histoneSL, and the combination of poly(A) and histoneSL on luciferase expression from mRNA in vivo was examined. Therefore different mRNAs were injected intradermally into mice. Mice were sacrificed 16 hours after injection and Luciferase levels at the injection sites were measured. Luciferase is expressed from mRNA having either a histoneSL or a poly(A) sequence. Strikingly however, the combination of poly(A) and histoneSL strongly increases the luciferase level, manifold above the level observed with either of the individual elements, thus acting synergistically. Data are graphed as mean RLU±SEM (relative light units±standard error of mean). Specific RLU are summarized in Example 10.5.

EXAMPLES

The following Examples are intended to illustrate the invention further and shall not be construed to limit the present invention thereto.

1. Generation of Histone-Stem-Loop Consensus Sequences

Prior to the experiments, histone stem-loop consensus sequences were determined on the basis of metazoan and protozoan histone stem-loop sequences. Sequences were taken from the supplement provided by Lopez et al. (Dávila López, M., & Samuelsson, T. (2008), RNA (New York, N.Y.), 14(1), 1-10. doi:10.1261/rna.782308), who identified a large number of natural histone stem-loop sequences by searching genomic sequences and expressed sequence tags. First, all sequences from metazoa and protozoa (4001 sequences), or all sequences from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. In addition, more restrictive consensus sequences were also obtained, increasingly emphasizing conserved nucleotides 2. Preparation of DNA-Templates A vector for in vitro transcription was constructed containing a T7 promoter followed by a GC-enriched sequence coding for *Photinus pyralis* luciferase (ppLuc (GC)), the center part of the 3' untranslated region (UTR) of alpha-globin (ag), and a poly(A) sequence. The poly(A) sequence was immediately followed by a restriction site used for linearization of the vector before in vitro transcription in order to obtain mRNA ending in an A64 poly(A) sequence. mRNA obtained from this vector accordingly by in vitro transcription is designated as "ppLuc(GC)-ag-A64".

Linearization of this vector at alternative restriction sites before in vitro transcription allowed to obtain mRNA either extended by additional nucleotides 3' of A64 or lacking A64. In addition, the original vector was modified to include alternative sequences. In summary, the following mRNAs were obtained from these vectors by in vitro transcription (mRNA sequences are given in FIGS. 6 to 17):

ppLuc(GC)-ag (SEQ ID NO: 43)
ppLuc(GC)-ag-A64 (SEQ ID NO: 44)
ppLuc(GC)-ag-histoneSL (SEQ ID NO: 45)
ppLuc(GC)-ag-A64-histoneSL (SEQ ID NO: 46)
ppLuc(GC)-ag-A120 (SEQ ID NO: 47)
ppLuc(GC)-ag-A64-ag (SEQ ID NO: 48)
ppLuc(GC)-ag-A64-aCPSL (SEQ ID NO: 49)
ppLuc(GC)-ag-A64-PolioCL (SEQ ID NO: 50)
ppLuc(GC)-ag-A64-G30 (SEQ ID NO: 51)
ppLuc(GC)-ag-A64-U30 (SEQ ID NO: 52)
ppLuc(GC)-ag-A64-SL (SEQ ID NO: 53)
ppLuc(GC)-ag-A64-N32 (SEQ ID NO: 54)

Furthermore DNA plasmid sequences coding for the autoimmune self-antigen MOG were prepared accordingly as described above.

In summary, the following mRNAs were obtained from these vectors by in vitro transcription (mRNA sequences are given in FIGS. 18 to 19):
MmMOG(wt)-ag-A64-C30 (SEQ ID NO: 55)
MmMOG(wt)-ag-A64-C30-histoneSL (SEQ ID NO: 56)

3. In Vitro Transcription

The DNA-template according to Example 2 was linearized and transcribed in vitro using T7-Polymerase. The DNA-template was then digested by DNase-treatment. All mRNA-transcripts contained a 5'-CAP structure obtained by adding an excess of N7-Methyl-Guanosine-5'-Triphosphate-5'-Guanosine to the transcription reaction. mRNA thus obtained was purified and resuspended in water.

4. Enzymatic Adenylation of mRNA

Two mRNAs were enzymatically adenylated:
ppLuc(GC)-ag-A64 and ppLuc(GC)-ag-histoneSL.

To this end, RNA was incubated with *E. coli* Poly(A)-polymerase and ATP (Poly(A) Polymerase Tailing Kit, Epicentre, Madison, USA) following the manufacturer's instructions. mRNA with extended poly(A) sequence was purified and resuspended in water. The length of the poly(A) sequence was determined via agarose gel electrophoresis. Starting mRNAs were extended by approximately 250 adenylates, the mRNAs obtained are designated as
ppLuc(GC)-ag-A300 and ppLuc(GC)-ag-histoneSL-A250, respectively.

5. Luciferase Expression by mRNA Electroporation

HeLa cells were trypsinized and washed in opti-MEM. $1 \times 10^5$ cells in 200 µl of opti-MEM each were electroporated with 0.5 µg of ppLuc-encoding mRNA. As a control, mRNA not coding for ppLuc was electroporated separately. Electroporated cells were seeded in 24-well plates in 1 ml of RPMI 1640 medium. 6, 24, or 48 hours after transfection, medium was aspirated and cells were lysed in 200 µl of lysis buffer (25 mM Tris, pH 7.5 (HCl), 2 mM EDTA, 10% glycerol, 1% Triton X-100, 2 mM DTT, 1 mM PMSF). Lysates were stored at −20° C. until ppLuc activity was measured.

6. Luciferase Expression by mRNA Lipofection

HeLa cells were seeded in 96 well plates at a density of $2 \times 10^4$ cells per well. The following day, cells were washed in opti-MEM and then transfected with 0.25 µg of Lipofectin-complexed ppLuc-encoding mRNA in 150 µl of opti-MEM. As a control, mRNA not coding for ppLuc was lipofected separately. In some wells, opti-MEM was aspirated and cells were lysed in 200 µl of lysis buffer 6 hours after the start of transfection. In the remaining wells, opti-MEM was exchanged for RPMI 1640 medium at that time. In these wells, medium was aspirated and cells were lysed in 200 µl of lysis buffer 24 or 48 hours after the start of transfection. Lysates were stored at −20° C. until ppLuc activity was measured.

7. Luciferase Measurement ppLuc activity was measured as relative light units (RLU) in a BioTek SynergyHT plate reader at 5 seconds measuring time using 50 µl of lysate and 200 µl of luciferin buffer (25 mM Glycylglycin, pH 7.8 (NaOH), 15 mM $MgSO_4$, 2 mM ATP, 75 µM luciferin). Specific RLU were calculated by subtracting RLU of the control RNA from total RLU.

8. Luciferase Expression by Intradermal mRNA Injection (Luciferase Expression In Vivo)

Mice were anaesthetized with a mixture of Rompun and Ketavet. Each ppLuc-encoding mRNA was injected intradermally (0.5 µg of mRNA in 50 µl per injection). As a control, mRNA not coding for ppLuc was injected separately. 16 hours after injection, mice were sacrificed and tissue collected. Tissue samples were flash frozen in liquid nitrogen and lysed in a tissue lyser (Qiagen) in 800 µl of lysis buffer (25 mM Tris, pH 7.5 (HCl), 2 mM EDTA, 10% glycerol, 1% Triton X-100, 2 mM DTT, 1 mM PMSF). Subsequently samples were centrifuged at 13500 rpm at 4° C. for 10 minutes. Lysates were stored at −80° C. until ppLuc activity was measured (see 7. luciferase measurement).

9. Experimental Autoimmune Encephalomyelitis (EAE):

Among autoimmune diseases a particular prominent example is multiple sclerosis (MS). MS is one of the most frequently occurring neurological diseases in young adults and affects about 1 million people worldwide. It is commonly accepted that MS is triggered by an autoimmune reaction against myelin components (e.g. myelin basic protein (MBP), proteolipidprotein (PLP), myelin-oligodendroglialprotein (MOG), etc.), of the human body, wherein a combination of genetic predisposition and environmental factors is assumed to be involved in the onset of MS. A frequently investigated model for multiple sclerosis is the mouse model of experimental autoimmune encephalomyelitis (EAE). EAE is triggered in C57BL/6 mice at day 0 by administration of recombinant MOG protein and an adjuvant cocktail. The cocktail contains recombinant MOG protein and CFA, the administration is carried out via injection with complete Freund's adjuvans. A sensibilization is achieved by administration of Pertussis toxin. The mice are dazed with KetaminNetranquil prior to administration.

In order to weaken the symptoms of disease, mice are vaccinated with the mRNAs according to SEQ ID NOs: 55 and 56 after triggering EAE in the mouse model. Therefore, mRNAs encoding MOG (the construct according to SEQ ID NOs: 55 and 56) are administered via injection in two cycles with one week difference between both cycles. In each of those cycles four injections are carried out (on days 1, 2, 3, 4, 15, 16, 17 and 18), i.e., in each cycle administration is carried out at four subsequent days per week. The mRNAs according to SEQ ID NOs: 55 and 56 are formulated with protamine and administered in a concentration of 10 µg per ear per injection (intradermally).

The mice and the progression of the disease is monitored over the whole time period in regular intervals. The progression of the disease is determined upon following EAE score, which uses the extent of paralysis as a measure for progression of disease:

| | |
|---|---|
| 0 | no symptoms; |
| 0.5 | end of tail paresis; |
| 1 | complete tail paresis; |
| 2 | weak distal paresis; |
| 2.5 | body reflexes restricted upon paresis; |
| 3 | medium paresis, abdominal muscles involved; |
| 3.5 | paresis of hind legs, belly touches the ground; |
| 4 | paraplegia or tetraparesis; |
| 4.5 | tetraplegia or tetraparesis + incontinence; |
| 5 | moribund. |

10 Results 10.1 Histone Stem-Loop Sequences:

In order to characterize histone stem-loop sequences, sequences from metazoa and protozoa (4001 sequences), or from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. Within the consensus sequence of metazoa and protozoa combined, 3 nucleotides are conserved, a T/U in the loop and a G and a C in the stem, forming a base pair. Structurally, typically a 6 base-pair stem and a loop of 4 nucleotides is formed. However, deviating structures are common: Of 84 human histone stem-loops, two contain a stem of only 5 nucleotides comprising 4 base-pairs and one mismatch.

Another human histone stem-loop contains a stem of only 5 base-pairs. Four more human histone stem-loops contain a 6 nucleotide long stem, but include one mismatch at three different positions, respectively. Furthermore, four human histone stem-loops contain one wobble base-pair at two different positions, respectively. Concerning the loop, a length of 4 nucleotides seems not to be strictly required, as a loop of 5 nucleotides has been identified in *D. discoideum*.

In addition to the consensus sequences representing all nucleotides present in the sequences analyzed, more restrictive consensus sequences were also obtained, increasingly emphasizing conserved nucleotides. In summary, the following sequences were obtained:

(Cons): represents all nucleotides present
(99%): represents at least 99% of all nucleotides present
(95%): represents at least 95% of all nucleotides present
(90%): represents at least 90% of all nucleotides present The results of the analysis of histone stem-loop sequences are summarized in the following Tables 1 to 5 (see also FIGS. 1 to 5):

TABLE 1

Metazoan and protozoan histone stem-loop consensus sequence: (based on an alignment of 4001 metazoan and protozoan histone stem-loop sequences) (see also FIG. 1)

| | < | < | < | < | < | < | • | • | • | • | • | > |
|---|---|---|---|---|---|---|---|---|---|---|---|---|---|---|---|
| # A | 2224 | 1586 | 3075 | 2872 | 1284 | 184 | 0 | 13 | 12 | 9 | 1 | 47 | 59 | 0 | 675 | 3818 |
| # T | 172 | 188 | 47 | 205 | 19 | 6 | 0 | 569 | 1620 | 199 | 3947 | 3830 | 3704 | 4001 | 182 | 1 |
| # C | 1557 | 2211 | 875 | 918 | 2675 | 270 | 0 | 3394 | 2342 | 3783 | 51 | 119 | 227 | 0 | 3140 | 7 |
| # G | 25 | 16 | 4 | 6 | 23 | 3541 | 4001 | 25 | 27 | 10 | 2 | 5 | 11 | 0 | 4 | 175 |
| Cons | N* | N* | N | N | N | N | G | N | N | N | N | N | N | T | N | N |
| 99% | H* | H* | H | H | V | V | G | Y | Y | Y | Y | H | H | T | H | R |
| 95% | M* | H* | M | H | M | S | G | Y | Y | Y | T | T | Y | T | M | A |
| 90% | M* | M* | M | M | M | S | G | Y | Y | C | T | T | T | T | M | A |

| | > | > | > | > | > | | | | | | |
|---|---|---|---|---|---|---|---|---|---|---|---|
| # A | 195 | 1596 | 523 | 0 | 14 | 3727 | 61 | 771 | 2012 | 2499 |
| # T | 21 | 15 | 11 | 0 | 179 | 8 | 64 | 557 | 201 | 690 |
| # C | 50 | 31 | 16 | 4001 | 3543 | 154 | 3870 | 2636 | 1744 | 674 |
| # G | 3735 | 2359 | 3451 | 0 | 265 | 112 | 4 | 37 | 43 | 138 |

TABLE 1-continued

Metazoan and protozoan histone stem-loop consensus sequence: (based on an alignment of 4001 metazoan and protozoan histone stem-loop sequences) (see also FIG. 1)

| Cons | N | N | N | C | N | N | N | N* | N* | N* |
|---|---|---|---|---|---|---|---|---|---|---|
| 99% | V | V | R | C | B | V | H | H* | N* | N* |
| 95% | R | R | R | C | S | M | C | H* | H* | H* |
| 90% | G | R | R | C | S | A | C | H* | M* | H* |

TABLE 2

Protozoan histone stem-loop consensus sequence: (based on an alignment of 131 protozoan histone stem-loop sequences) (see also FIG. 2)

|   | < | < | < | < | < | < | • | • | • | • | > | > | > | > | > | > |   |   |   |   |   |   |   |
|---|---|---|---|---|---|---|---|---|---|---|---|---|---|---|---|---|---|---|---|---|---|---|---|
| # A | 52 | 32 | 71 | 82 | 76 | 13 | 0 | 12 | 12 | 9 | 1 | 46 | 3 | 0 | 75 | 82 | 53 | 79 | 20 | 0 | 4 | 94 | 17 | 35 | 74 | 56 |
| # T | 20 | 32 | 37 | 21 | 8 | 3 | 0 | 21 | 85 | 58 | 86 | 70 | 65 | 131 | 28 | 1 | 17 | 13 | 10 | 0 | 15 | 7 | 31 | 32 | 20 | 28 |
| # C | 45 | 59 | 20 | 25 | 38 | 0 | 0 | 86 | 8 | 54 | 42 | 13 | 58 | 0 | 27 | 2 | 6 | 31 | 10 | 131 | 112 | 5 | 82 | 58 | 30 | 40 |
| # G | 14 | 8 | 3 | 3 | 9 | 115 | 131 | 12 | 26 | 10 | 2 | 2 | 5 | 0 | 1 | 46 | 55 | 8 | 91 | 0 | 0 | 25 | 1 | 6 | 7 | 7 |
| Cons | N* | N* | N | N | N | D | G | N | N | N | N | N | T | N | N | N | N | N | C | H | N | N | N* | N* | N* |   |
| 99% | N* | N* | N | N | D | G | N | N | B | N | N | T | H | V | N | N | N | C | H | N | H | N* | N* | N* |   |   |
| 95% | N* | N* | H | H | N | R | G | N | N | Y | H | B | T | H | R | D | N | N | C | Y | D | H | H* | N* | N* |   |
| 90% | N* | H* | H | H | V | R | G | N | D | B | Y | H | Y | T | H | R | D | H | N | C | Y | R | H | H* | H* |   |

TABLE 3

Metazoan histone stem-loop consensus sequence: (based on an alignment of 3870 (including 1333 vertebrate sequences) metazoan histone stem-loop sequences) (see also FIG. 3)

|   | < | < | < | < | < | < | • | • | • | • | > |
|---|---|---|---|---|---|---|---|---|---|---|---|
| # A | 2172 | 1554 | 3004 | 2790 | 1208 | 171 | 0 | 1 | 0 | 0 | 0 | 1 | 56 | 0 | 600 | 3736 |
| # T | 152 | 156 | 10 | 184 | 11 | 3 | 0 | 548 | 1535 | 141 | 3861 | 3760 | 3639 | 3870 | 154 | 0 |
| # C | 1512 | 2152 | 855 | 893 | 2637 | 270 | 0 | 3308 | 2334 | 3729 | 9 | 106 | 169 | 0 | 3113 | 5 |
| # G | 11 | 8 | 1 | 3 | 14 | 3426 | 3870 | 13 | 1 | 0 | 0 | 3 | 6 | 0 | 3 | 129 |
| Cons | N* | N* | N | N | N | N | G | N | B | Y | Y | N | N | T | N | V |
| 99% | H* | H* | M | H | M | V | G | Y | Y | Y | T | Y | H | T | H | R |
| 95% | M* | M* | M | M | M | S | G | V | V | C | T | T | Y | T | M | A |
| 90% | M* | M* | M | M | M | S | G | Y | Y | C | T | T | T | T | M | A |

|   | > | > | > | > | > |
|---|---|---|---|---|---|
| # A | 142 | 1517 | 503 | 0 | 10 | 3633 | 44 | 736 | 1938 | 2443 |
| # T | 4 | 2 | 1 | 0 | 164 | 1 | 33 | 525 | 181 | 662 |
| # C | 44 | 0 | 6 | 3870 | 3431 | 149 | 3788 | 2578 | 1714 | 634 |
| # G | 3680 | 2351 | 3360 | 0 | 265 | 87 | 3 | 31 | 36 | 131 |

TABLE 3-continued

Metazoan histone stem-loop consensus sequence: (based on an alignment of 3870 (including 1333 vertebrate sequences) metazoan histone stem-loop sequences) (see also FIG. 3)

| | Cons | N | D | N | C | N | N | N | N* | N* | N* |
|---|---|---|---|---|---|---|---|---|---|---|---|
| | 99% | V | R | R | C | B | V | M | H* | H* | N* |
| | 95% | G | R | R | C | S | M | C | H* | H* | H* |
| | 90% | G | R | R | C | S | A | C | H* | M* | H* |

TABLE 4

Vertebrate histone stem-loop consensus sequence: (based on an alignment of 1333 vertebrate histone stem-loop sequences) (see also FIG. 4)

| | | | | | | < | < | < | < | < | < | • | • | • | • | > |
|---|---|---|---|---|---|---|---|---|---|---|---|---|---|---|---|---|
| # A | 661 | 146 | 1315 | 1323 | 920 | 8 | 0 | 1 | 0 | 0 | 0 | 1 | 4 | 0 | 441 | 1333 |
| # T | 63 | 121 | 2 | 2 | 6 | 2 | 0 | 39 | 1217 | 2 | 1331 | 1329 | 1207 | 1333 | 30 | 0 |
| # C | 601 | 1062 | 16 | 6 | 403 | 1 | 0 | 1293 | 116 | 1331 | 2 | 0 | 121 | 0 | 862 | 0 |
| # G | 8 | 4 | 0 | 2 | 4 | 1322 | 1333 | 0 | 0 | 0 | 0 | 3 | 1 | 0 | 0 | 0 |
| Cons | N* | N* | H | N | N | N | G | H | Y | Y | V | D | N | T | H | A |
| 99% | H* | H* | M | A | M | G | G | V | Y | C | T | T | V | T | H | A |
| 95% | H* | H* | A | A | M | G | G | C | V | C | T | T | V | T | M | A |
| 90% | M* | M* | A | A | M | G | G | C | T | C | T | T | T | T | M | A |

| | | | > | > | > | > | > | | | | |
|---|---|---|---|---|---|---|---|---|---|---|---|
| # A | | | 0 | 1199 | 21 | 0 | 1 | 1126 | 26 | 81 | 380 | 960 |
| # T | | | 1 | 0 | 1 | 0 | 2 | 1 | 22 | 91 | 91 | 12 |
| # C | | | 2 | 0 | 0 | 1333 | 1328 | 128 | 1284 | 1143 | 834 | 361 |
| # G | | | 1330 | 134 | 1311 | 0 | 2 | 78 | 1 | 18 | 28 | 0 |
| Cons | | | B | R | D | C | N | N | N | N* | N* | H* |
| 99% | | | G | R | R | C | C | V | H | N* | N* | M* |
| 95% | | | G | R | G | C | C | V | C | W | H* | M* |
| 90% | | | G | R | G | C | C | M | C | Y* | M* | M* |

TABLE 5

Homo sapiens histone stem-loop consensus sequence: (based on an alignment of 84 human histone stem-loop sequences) (see also FIG. 5)

| | < | < | < | < | < | < | • | • | • | • | > | > | > | > | > | > | | | | | |
|---|---|---|---|---|---|---|---|---|---|---|---|---|---|---|---|---|---|---|---|---|---|
| # A | 10 | 17 | 84 | 84 | 76 | 1 | 0 | 1 | 0 | 0 | 0 | 1 | 0 | 0 | 12 | 84 | 0 | 65 | 3 | 0 | 0 | 69 | 5 | 0 | 10 | 64 |
| # T | 8 | 6 | 0 | 0 | 2 | 2 | 0 | 1 | 67 | 0 | 84 | 80 | 81 | 84 | 5 | 0 | 0 | 0 | 0 | 0 | 0 | 4 | 25 | 24 | 3 |
| # C | 62 | 61 | 0 | 0 | 6 | 0 | 0 | 82 | 17 | 84 | 0 | 0 | 3 | 0 | 67 | 0 | 1 | 0 | 0 | 0 | 84 | 84 | 5 | 75 | 57 | 44 | 17 |
| # G | 4 | 0 | 0 | 0 | 0 | 81 | 84 | 0 | 0 | 0 | 0 | 3 | 0 | 0 | 0 | 0 | 83 | 19 | 81 | 0 | 0 | 10 | 0 | 2 | 6 | 0 |

TABLE 5-continued

Homo sapiens histone stem-loop consensus sequence: (based on an alignment of 84 human histone stem-loop sequences)
(see also FIG. 5)

|   |    |    | <  | <  | <  | <  | <  | •  | •  | •  | •  | >  | >  | >  | >  | >  | >  |    |    |    |
|---|----|----|----|----|----|----|----|----|----|----|----|----|----|----|----|----|----|----|----|----|
| Cons | N* | H* | A | A | H | D | C | H | Y | C | T | D | Y | T | H | A | S | R | R | C | C | V | H | B* | N* | H* |
| 99% | N* | H* | A | A | H | D | C | H | Y | C | T | D | Y | T | H | A | S | R | R | C | C | V | H | B* | N* | H* |
| 95% | H* | H* | A | A | M | G | G | C | Y | C | T | T | T | T | H | A | G | R | G | C | C | V | M | Y* | N* | M* |
| 90% | H* | M* | A | A | A | G | C | C | Y | C | T | T | T | T | M | A | C | R | C | C | C | R | M | Y* | H* | M* |

Wherein the used abbreviations were defined as followed:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | present or not | Base may be present or not |

10.2 the Combination of Poly(A) and histoneSL Increases Protein Expression from mRNA in a Synergistic Manner.

To investigate the effect of the combination of poly(A) and histoneSL on protein expression from mRNA, mRNAs with different sequences 3' of the alpha-globin 3'-UTR were synthesized: mRNAs either ended just 3' of the 3'-UTR, thus lacking both poly(A) sequence and histoneSL, or contained either an A64 poly(A) sequence or a histoneSL instead, or both A64 poly(A) and histoneSL 3' of the 3'-UTR. Luciferase-encoding mRNAs or control mRNA were electroporated into HeLa cells. Luciferase levels were measured at 6, 24, and 48 hours after transfection (see following Table 6 and FIG. 20).

TABLE 6

| mRNA | RLU at 6 hours | RLU at 24 hours | RLU at 48 hours |
|---|---|---|---|
| ppLuc(GC)-ag-A64-histoneSL | 466553 | 375169 | 70735 |
| ppLuc(GC)-ag-histoneSL | 50947 | 3022 | 84 |
| ppLuc(GC)-ag-A64 | 10471 | 19529 | 4364 |
| ppLuc(GC)-ag | 997 | 217 | 42 |

Little luciferase was expressed from mRNA having neither poly(A) sequence nor histoneSL. Both a poly(A) sequence or the histoneSL increased the luciferase level to a similar extent. Either mRNA gave rise to a luciferase level much higher than did mRNA lacking both poly(A) and histoneSL. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 7).

TABLE 7

|  | A64 | histoneSL | RLU at 6 hours | RLU at 24 hours | RLU at 48 hours |
|---|---|---|---|---|---|
|  | + | + | 466553 | 375169 | 70735 |
|  | − | + | 50947 | 3022 | 84 |
|  | + | − | 10471 | 19529 | 4364 |
| Synergy |  |  | 7.6 | 16.6 | 15.9 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was up to 16.6 times higher than if their effects were purely additive. This result confirms that the combination of poly(A) and histoneSL effects a markedly synergistic increase in protein expression.

10.3 the Combination of Poly(A) and histoneSL Increases Protein Expression from mRNA Irrespective of their Order.

The effect of the combination of poly(A) and histoneSL might depend on the length of the poly(A) sequence and the order of poly(A) and histoneSL. Thus, mRNAs with increasing poly(A) sequence length and mRNA with poly(A) and histoneSL in reversed order were synthesized: Two mRNAs contained 3' of the 3'-UTR either an A120 or an A300 poly(A) sequence. One further mRNA contained 3' of the 3'-UTR first a histoneSL followed by an A250 poly(A) sequence. Luciferase-encoding mRNAs or control mRNA were lipofected into HeLa cells. Luciferase levels were measured at 6, 24, and 48 hours after the start of transfection (see following Table 8 and FIG. 21).

TABLE 8

| mRNA | RLU at 6 hours | RLU at 24 hours | RLU at 48 hours |
|---|---|---|---|
| ppLuc(GC)-ag-histoneSL-A250 | 98472 | 734222 | 146479 |
| ppLuc(GC)-ag-A64-histoneSL | 123674 | 317343 | 89579 |
| ppLuc(GC)-ag-histoneSL | 7291 | 4565 | 916 |

TABLE 8-continued

| mRNA | RLU at 6 hours | RLU at 24 hours | RLU at 48 hours |
|---|---|---|---|
| ppLuc(GC)-ag-A300 | 4357 | 38560 | 11829 |
| ppLuc(GC)-ag-A120 | 4371 | 45929 | 10142 |
| ppLuc(GC)-ag-A64 | 1928 | 26781 | 537 |

Both an A64 poly(A) sequence or the histoneSL gave rise to comparable luciferase levels. In agreement with the previous experiment did the combination of A64 and histoneSL strongly increase the luciferase level, manifold above the level observed with either of the individual elements. The magnitude of the rise in luciferase level due to combining poly(A) and histoneSL in the same mRNA demonstrates that they are acting synergistically. The synergy between A64 and histoneSL was quantified as before based on the luciferase levels of A64-histoneSL, A64, and histoneSL mRNA (see following Table 9). The luciferase level from mRNA combining A64 and histoneSL was up to 61.7 times higher than if the effects of poly(A) and histoneSL were purely additive.

TABLE 9

| | A64 | histoneSL | RLU at 6 hours | RLU at 24 hours | RLU at 48 hours |
|---|---|---|---|---|---|
| | + | + | 123674 | 317343 | 89579 |
| | − | + | 7291 | 4565 | 916 |
| | + | − | 1928 | 26781 | 537 |
| Synergy | | | 13.4 | 10.1 | 61.7 |

In contrast, increasing the length of the poly(A) sequence from A64 to A120 or to A300 increased the luciferase level only moderately (see Table 8 and FIG. 19). mRNA with the longest poly(A) sequence, A300, was also compared to mRNA in which a poly(A) sequence of similar length was combined with the histoneSL, histoneSL-A250. In addition to having a long poly(A) sequence, the order of histoneSL and poly(A) is reversed in this mRNA relative to A64-histoneSL mRNA. The combination of A250 and histoneSL strongly increased the luciferase level, manifold above the level observed with either histoneSL or A300. Again, the synergy between A250 and histoneSL was quantified as before comparing RLU from histoneSL-A250 mRNA to RLU from A300 mRNA plus histoneSL mRNA (see following Table 10). The luciferase level from mRNA combining A250 and histoneSL was up to 17.0 times higher than if the effects of poly(A) and histoneSL were purely additive.

TABLE 10

| | histoneSL | A250/A300 | RLU at 6 hours | RLU at 24 hours | RLU at 48 hours |
|---|---|---|---|---|---|
| | + | + | 98472 | 734222 | 146479 |
| | + | − | 7291 | 4565 | 916 |
| | − | + | 4357 | 38560 | 11829 |
| Synergy | | | 8.5 | 17.0 | 11.5 |

In summary, a highly synergistic effect of the combination of histoneSL and poly(A) on protein expression from mRNA has been demonstrated for substantially different lengths of poly(A) and irrespective of the order of poly(A) and histoneSL.

10.4 the Rise in Protein Expression by the Combination of Poly(A) and histoneSL is specific To investigate whether the effect of the combination of poly(A) and histoneSL on protein expression from mRNA is specific, mRNAs with alternative sequences in combination with poly(A) were synthesized: These mRNAs contained 3' of A64 one of seven distinct sequences, respectively. Luciferase-encoding mRNAs or control mRNA were electroporated into HeLa cells. Luciferase levels were measured at 6, 24, and 48 hours after transfection (see following Table 11 and FIG. 22).

TABLE 11

| mRNA | RLU at 6 hours | RLU at 24 hours | RLU at 48 hours |
|---|---|---|---|
| ppLuc(GC)-ag-A64-N32 | 33501 | 38979 | 2641 |
| ppLuc(GC)-ag-A64-SL | 28176 | 20364 | 874 |
| ppLuc(GC)-ag-A64-U30 | 41632 | 54676 | 3408 |
| ppLuc(GC)-ag-A64-G30 | 46763 | 49210 | 3382 |
| ppLuc(GC)-ag-A64-PolioCL | 46428 | 26090 | 1655 |
| ppLuc(GC)-ag-A64-aCPSL | 34176 | 53090 | 3338 |
| ppLuc(GC)-ag-A64-ag | 18534 | 18194 | 989 |
| ppLuc(GC)-ag-A64-histoneSL | 282677 | 437543 | 69292 |
| ppLuc(GC)-ag-histoneSL | 27597 | 3171 | 0 |
| ppLuc(GC)-ag-A64 | 14339 | 48414 | 9357 |

Both a poly(A) sequence or the histoneSL gave rise to comparable luciferase levels. Again, the combination of poly(A) and histoneSL strongly increased the luciferase level, manifold above the level observed with either of the individual elements, thus acting synergistically. In contrast, combining poly(A) with any of the alternative sequences was without effect on the luciferase level compared to mRNA containing only a poly(A) sequence. Thus, the combination of poly(A) and histoneSL increases protein expression from mRNA in a synergistic manner, and this effect is specific.

10.5 the Combination of Poly(A) and histoneSL Increases Protein Expression from mRNA in a Synergistic Manner In Vivo.

To investigate the effect of the combination of poly(A) and histoneSL on protein expression from mRNA in vivo, Luciferase-encoding mRNAs with different sequences 3' of the alpha-globin 3'-UTR or control mRNA were injected intradermally into mice: mRNAs contained either an A64 poly(A) sequence or a histoneSL instead, or both A64 poly(A) and histoneSL 3' of the 3'-UTR. Luciferase levels were measured at 16 hours after injection (see following Table 12 and FIG. 23).

TABLE 12

| mRNA | RLU at 16 hours |
|---|---|
| ppLuc(GC)-ag-A64-histoneSL | 38081 |
| ppLuc(GC)-ag-histoneSL | 137 |
| ppLuc(GC)-ag-A64 | 4607 |

Luciferase was expressed from mRNA having either a histoneSL or a poly(A) sequence. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 13).

TABLE 13

| A64 | histoneSL | RLU at 16 hours |
|---|---|---|
| + | + | 38081 |
| − | + | 137 |
| + | − | 4607 |
| Synergy | | 8.0 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was 8 times higher than if their effects were purely additive. This result confirms that the combination of poly(A) and histoneSL effects a markedly synergistic increase in protein expression in vivo.

The invention claimed is:

1. A nucleic acid molecule comprising:
   a) a polypeptide coding region, encoding an autoimmune self-antigen, wherein the autoimmune self-antigen is a polypeptide capable of inducing an immune response in a subject and wherein the autoimmune self-antigen is selected from the group consisting of myelin basic protein (MBP), proteolipid protein (PLP), myelin oligodendrocyte glycoprotein (MOG), CD44, preproinsulin, proinsulin, insulin, glutamic acid decaroxylase (GAD65), tyrosine phosphatase-like insulinoma antigen 2 (IA2), zinc transporter (ZnT8), heat shock protein 60 (HSP60), interphotoreceptor retinoid-binding protein (IRBP), acetylcholine receptor AchR, insulin-like growth factor-1 receptor (IGF-1R), m-protein from beta-hemolytic streptocci (pseudo-autoantigen), macrophage migration inhibitory factor, Ro/La RNP complex, alpha-fodrin, islet cell autoantigen, beta-fodrin, islet cell autoantigen, poly(ADP)ribose polymerase (PARP), NuMA, NOR-90, Ro60 autoantigen, p27 antigen, Ro60 autoantigen, a low-density lipoprotein, a Sm antigens of the U-1 small nuclear ribonucleoprotein complex, a RNP ribonucleoproteins, oxLDL, beta(2) GPI, HSP60/65, oxLDL/beta(2)GPI, cardiac beta(1)-adrenergic receptor, histidyl-tRNA synthetase (HisRS), and topoisomerase I;
   b) at least one histone stem-loop, and
   c) a poly(A) sequence or a polyadenylation signal.

2. The nucleic acid molecule of claim 1, wherein the molecule does not comprise a sequence encoding a reporter protein, a marker or selection protein.

3. The nucleic acid molecule of claim 1, wherein the molecule does not comprise sequence encoding a reporter protein, a marker or selection protein.

4. The nucleic acid molecule of claim 1, wherein the nucleic acid is a RNA.

5. The nucleic acid molecule of claim 1, wherein the poly(A) sequence comprises a sequence of about 25 to about 400 adenosine nucleotides.

6. The nucleic acid molecule of claim 1, wherein the polyadenylation signal comprises the consensus sequence NN(U/T)ANA.

7. The nucleic acid molecule of claim 1, wherein at least one guanosine, uridine, adenosine, thymidine, or cytidine position of the nucleic acid molecule is substituted with an analogue of these nucleotides selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, or puromycin-5'-triphosphate, and xanthosine-5'-triphosphate.

8. The nucleic acid sequence molecule of claim 1, wherein the G/C content of the polypeptide coding region is increased compared with the G/C content of the coding region of a wild-type nucleic acid encoding the autoimmune disease antigen or the allergenic antigen.

9. The nucleic acid molecule of claim 4, wherein the RNA comprises a 5' cap structure and a poly(A) sequence of about 25 to about 400 adenosine nucleotides.

10. The nucleic acid molecule of claim 1, wherein the nucleic acid molecule comprises a sequence of at least 10 consecutive cytidines.

11. The nucleic acid molecule of claim 1, wherein the nucleic acid molecule further comprises a stabilizing sequence from the alpha globin 3' UTR, positioned 3' relative to the polypeptide coding region of the nucleic acid molecule.

12. A pharmaceutical composition comprising a nucleic acid molecule of claim 1 and a pharmaceutically acceptable carrier.

13. The pharmaceutical composition of claim 12, further comprising an adjuvant.

14. The pharmaceutical composition of claim 12, wherein the composition further comprises a cationic or polycationic compound in complex with the nucleic acid molecule.

15. The pharmaceutical composition of claim 14, wherein the polycationic polypeptide in complex with the nucleic acid molecule comprise protamine.

* * * * *